United States Patent
Chen

(10) Patent No.: US 11,981,665 B2
(45) Date of Patent: May 14, 2024

(54) SUBSTITUTED PYRIMIDINES, PHARMACEUTICAL COMPOSITIONS AND THERAPEUTIC METHODS THEREOF

(71) Applicant: Zhihong Chen, Lexington, MA (US)

(72) Inventor: Zhihong Chen, Lexington, MA (US)

( * ) Notice: Subject to any disclaimer, the term of this patent is extended or adjusted under 35 U.S.C. 154(b) by 0 days.

(21) Appl. No.: 17/856,761

(22) Filed: Jul. 1, 2022

(65) Prior Publication Data

US 2023/0109688 A1   Apr. 13, 2023

Related U.S. Application Data

(62) Division of application No. 16/639,972, filed as application No. PCT/US2018/048089 on Aug. 27, 2018, now Pat. No. 11,440,904.

(60) Provisional application No. 62/550,803, filed on Aug. 28, 2017.

(51) Int. Cl.
| | | |
|---|---|---|
| *C07D 405/14* | (2006.01) | |
| *C07D 405/12* | (2006.01) | |
| *C07D 473/16* | (2006.01) | |
| *C07D 487/04* | (2006.01) | |
| *C07D 495/04* | (2006.01) | |

(52) U.S. Cl.
CPC ......... *C07D 405/14* (2013.01); *C07D 405/12* (2013.01); *C07D 473/16* (2013.01); *C07D 487/04* (2013.01); *C07D 495/04* (2013.01)

(58) Field of Classification Search
CPC .............. A61K 31/357; A61K 31/381; A61K 31/4188; A61K 31/435; C07D 487/04; C07D 495/04; C07D 405/14; C07D 473/16

See application file for complete search history.

(56) References Cited

FOREIGN PATENT DOCUMENTS

WO   WO2010129053   * 11/2010

* cited by examiner

*Primary Examiner* — Samantha L Shterengarts
*Assistant Examiner* — Karen Cheng
(74) *Attorney, Agent, or Firm* — Milstein Zhang & Wu LLC

(57) ABSTRACT

The invention provide novel pyrimidine derivatives and analogs having inhibitory activities towards certain tyrosine kinases, e.g., Bruton's tyrosine kinase (Btk) and/or Focal adhesion kinase (FAK), extracellular signal-regulated kinase (ERK), pharmaceutical compositions thereof, and methods of treatment, reduction or prevention of certain diseases or conditions mediated by such by tyrosine kinases, e.g., cancers, tumors, fibrosis, inflammatory diseases, autoimmune diseases, diabetes, or immunologically mediated diseases.

16 Claims, 7 Drawing Sheets

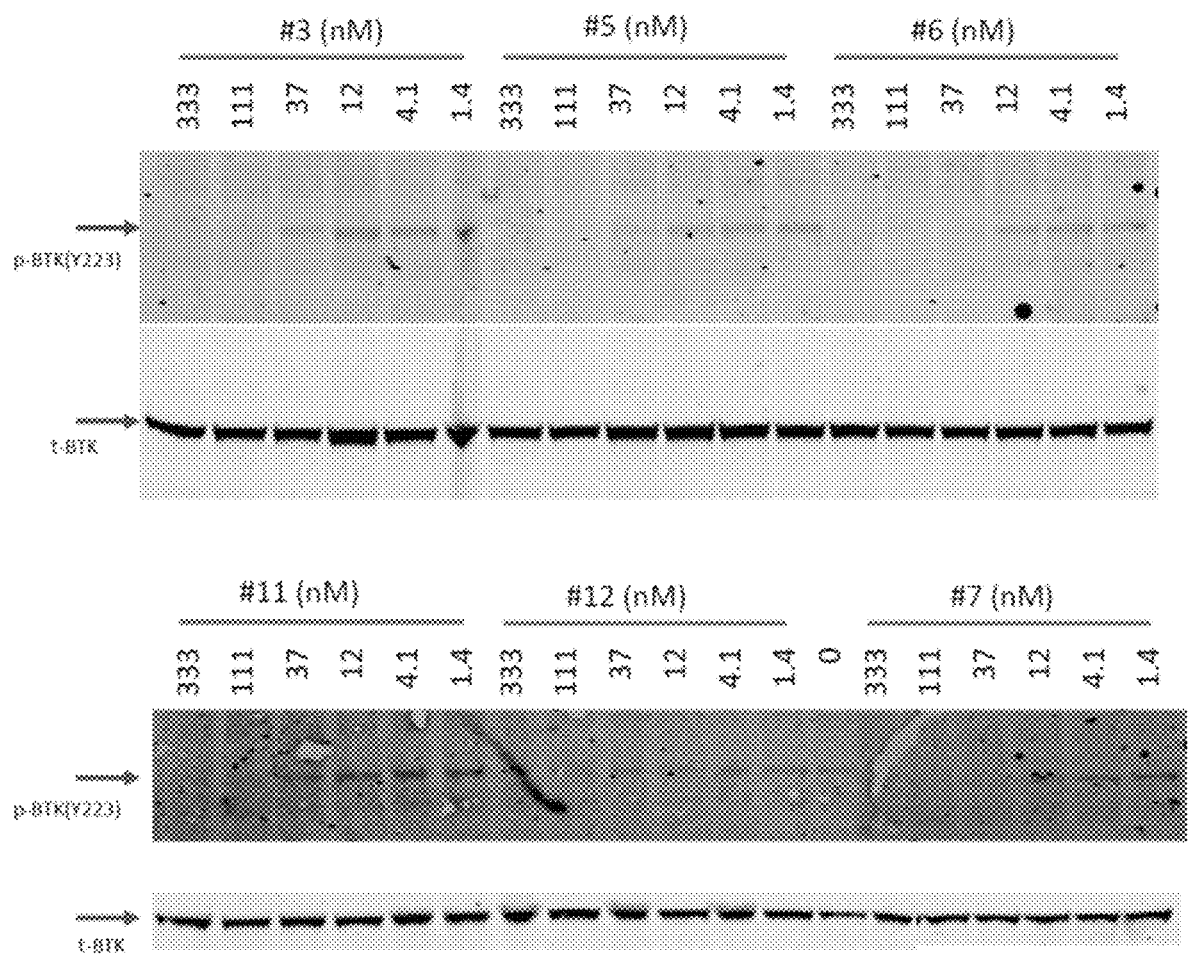
FIG. 1. Western blotting analysis of p-BTK(Y223) in Ramos cells

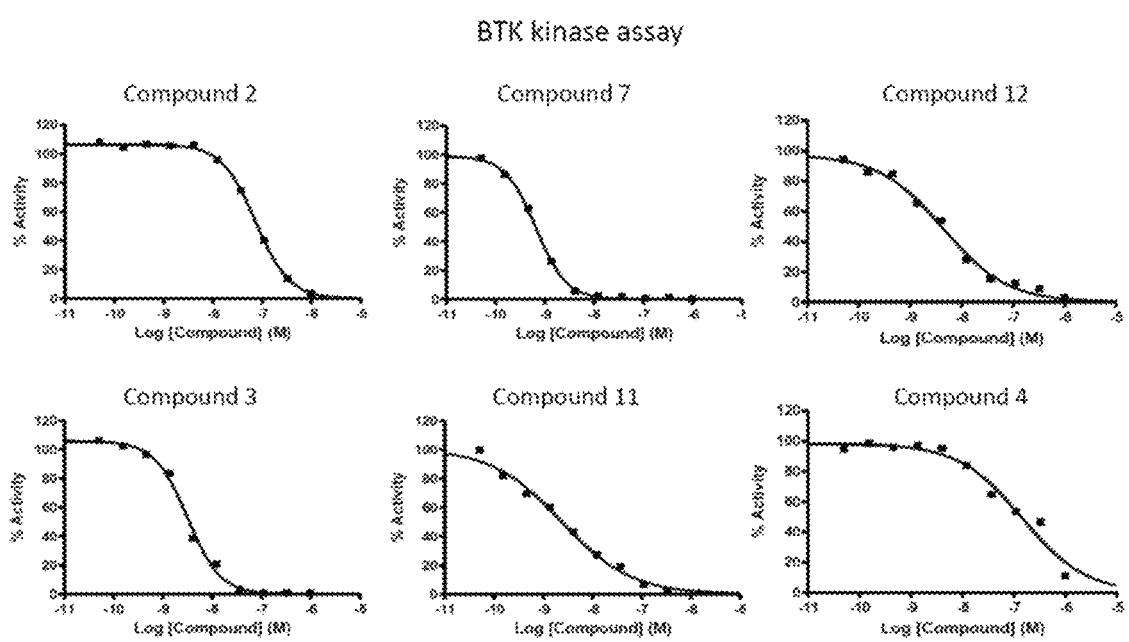
FIG. 2. Exemplary BTK IC$_{50}$ Data

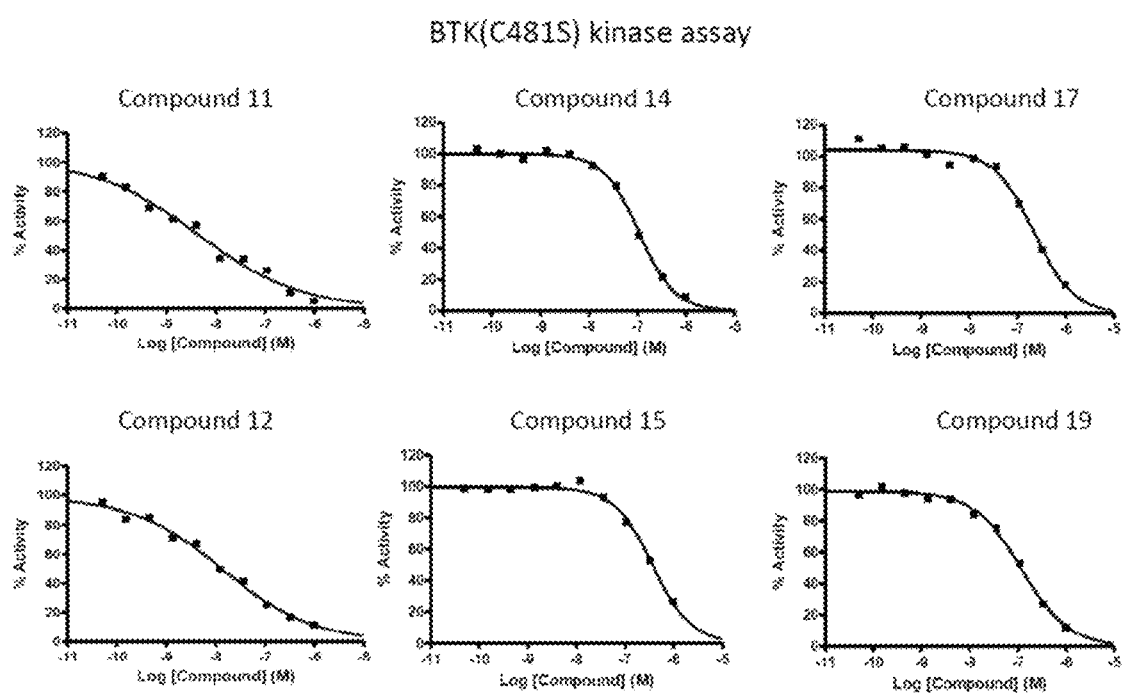
FIG. 3. Exemplary BTK(C481S) IC$_{50}$ Data

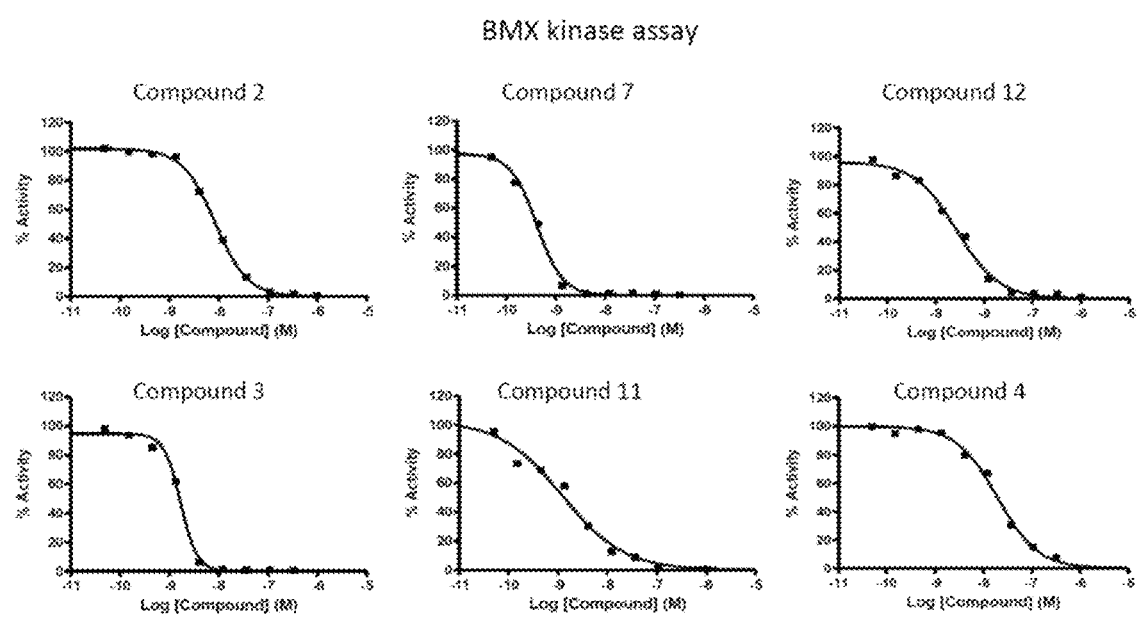
FIG. 4. Exemplary BMX $IC_{50}$ Data

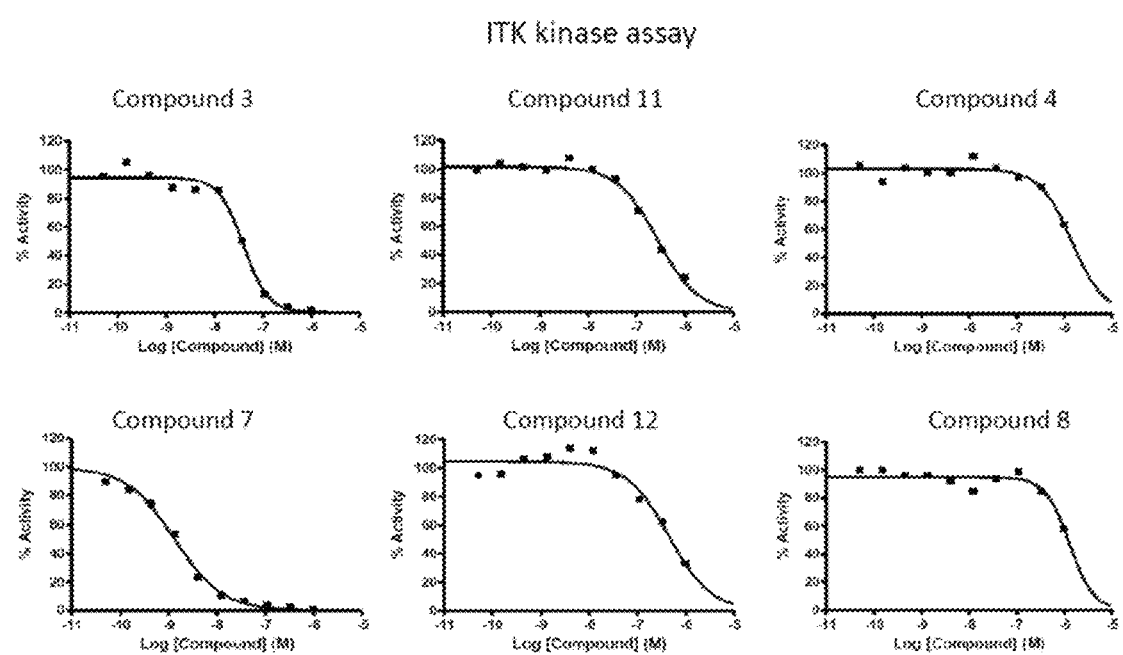
FIG. 5. Exemplary ITK $IC_{50}$ Data

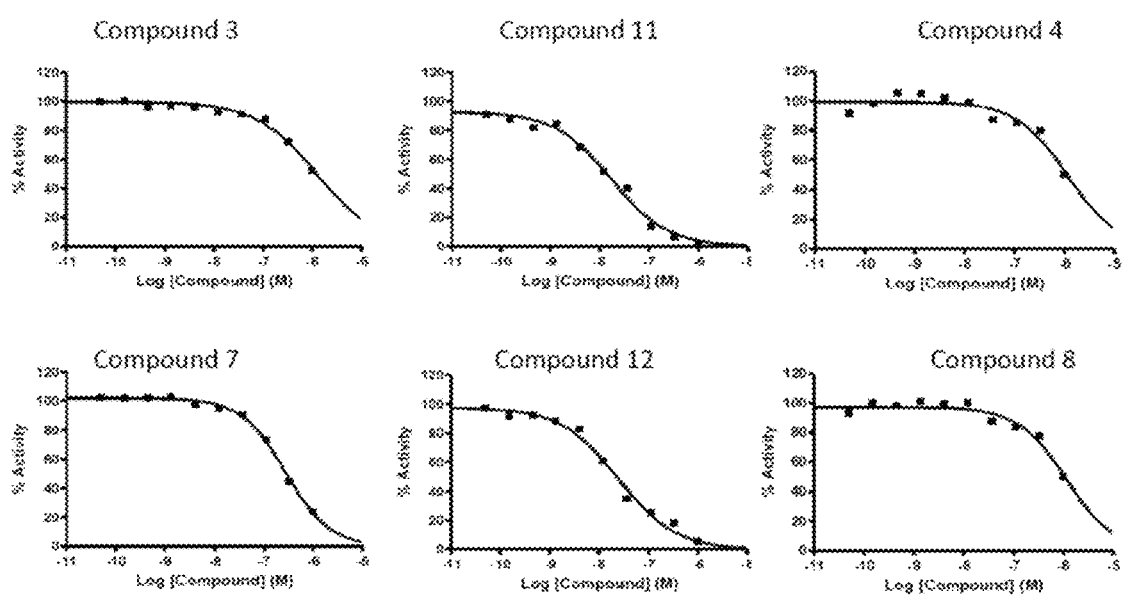
FIG. 6. Exemplary FAK IC$_{50}$ Data

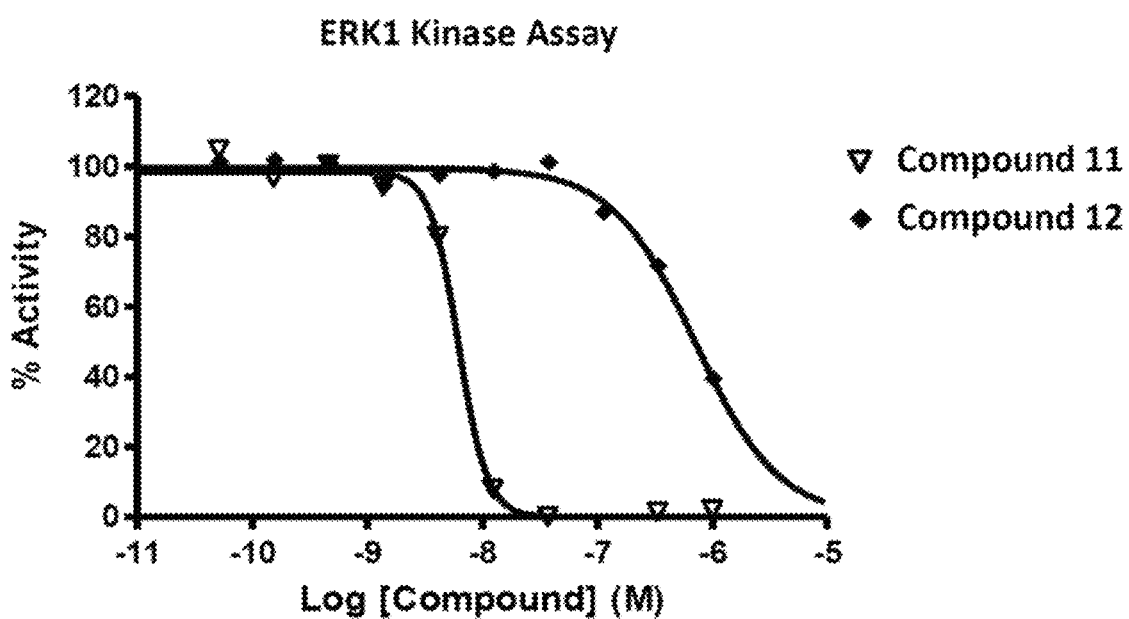
FIG. 7. Exemplary ERK1 $IC_{50}$ Data

SUBSTITUTED PYRIMIDINES, PHARMACEUTICAL COMPOSITIONS AND THERAPEUTIC METHODS THEREOF

PRIORITY CLAIMS AND RELATED PATENT APPLICATIONS

This application is a divisional of and claims the benefit of priority to U.S. application Ser. No. 16/639,972, filed Feb. 18, 2020, which is the U.S. national phase of and claims priority to PCT/US2018/048089, filed Aug. 27, 2018, which claims the benefit of priority to U.S. Provisional Application No. 62/550,803, filed Aug. 28, 2017, the content of each of which is incorporated herein by reference in its entirety.

TECHNICAL FIELD OF THE INVENTION

The invention generally relates to novel compounds and therapeutic uses thereof. More particularly, the invention provide novel pyrimidine derivatives and analogs having inhibitory activities towards certain tyrosine kinases, e.g., Bruton's tyrosine kinase, focal adhesion kinase, and/or extracellular signal-regulated kinase (ERK), pharmaceutical compositions thereof, and methods of treatment, reduction or prevention of certain diseases or conditions mediated by such by tyrosine kinases, e.g., cancers, inflammatory diseases, fibrosis, autoimmune diseases, or immunologically mediated diseases.

BACKGROUND OF THE INVENTION

Cancer is a group of diseases involving abnormal cell growth with the potential to invade or spread to other parts of the body. More than 100 types of cancers are known to affect humans. Over 90 million people had cancer in 2015 with about 14 million new cases occur a year while causing about 15% of human deaths. The most common types of cancer include lung cancer, prostate cancer, colorectal cancer and stomach cancer for men, and breast cancer, colorectal cancer, lung cancer and cervical cancer for women. While many treatment options for cancer exist, including surgery, chemotherapy, radiation therapy, hormonal therapy, targeted therapy and palliative care, cancer remains a top health threat.

Inflammatory disorders are a large group of conditions that underlie a vast variety of human diseases. Being the body's protective response to injury and infection, inflammation is a complex process involving many cell types as well as different components of blood. The inflammatory process works quickly to destroy and eliminate foreign and damaged cells, and to isolate the infected or injured tissues from the rest of the body. Inflammatory disorders arise when inflammation becomes uncontrolled, and causes destruction of healthy tissue. Many inflammatory disorders occur when the immune system mistakenly triggers inflammation in the absence of infection, such as inflammation of the joints in the case of rheumatoid arthritis. Others result from a response to tissue injury or trauma but affect the entire body. Overall, the estimated prevalence of immune-mediated inflammatory diseases in Western society is 5%-7%.

The therapeutics and methods currently available for the management of diseases or disorders such as cancers, tumors, fibrosis, inflammatory diseases, autoimmune diseases, or immunologically mediated diseases are inadequate. There remains an urgent and ongoing need for novel and improved therapeutics to effectively treat such diseases and conditions.

SUMMARY OF THE INVENTION

The invention is based in part on the unexpected discovery of novel pyrimidine derivatives and analogs that exhibit inhibitory activities towards certain tyrosine kinases, e.g., Bruton's tyrosine kinase (BTK) and/or focal adhesion kinase (FAK), and pharmaceutical compositions thereof. The pyrimidine derivatives disclosed herein are shown to effectively inhibit BTK and/or other TEC family non-receptor tyrosine kinases, e.g., bone marrow tyrosine kinase (BMX) or interleukin-2 inducing T-cell kinase (ITK). In addition, certain pyrimidine derivatives effectively inhibit resistant mutant BTK(C481S) and FAK as well as BTK. Furthermore, certain pyrimidine derivatives disclosed herein effectively inhibit resistant mutant BTK(C481S), FAK and extracellular signal-regulated kinase (ERK) as well as BTK.

Also disclosed herein are methods of treatment, reduction or prevention of certain diseases or conditions mediated by such by tyrosine kinases, e.g., BTK, BTK(C481S), FAK, ERK kinases, and/or other TEC family kinases. Such diseases and conditions include cancers, inflammatory diseases, fibrosis, autoimmune diseases, diabetes, or immunologically mediated diseases.

In one aspect, the invention generally relates to a compound having the structural formula of (I):

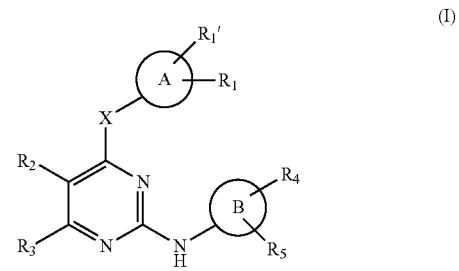

wherein,
X is $NH(CH_2)_n$, O or S, wherein n is 0 or 1;
A is a 5- to 7-membered, aliphatic or aromatic, cyclic or heterocyclic moiety;
B is a 5- to 7-membered, aliphatic or aromatic, cyclic or heterocyclic moiety;
$R_{1'}$ may be absent and each of $R_1$ and $R_{1'}$ (if present) is independently selected from halogen, $C_1$-$C_6$ alkyl, $C_1$-$C_6$ alkoxy, CN, OH, amino, carboxylic amide, sulfonamide and $R_{1x}$, wherein $R_{1x}$ is selected from:

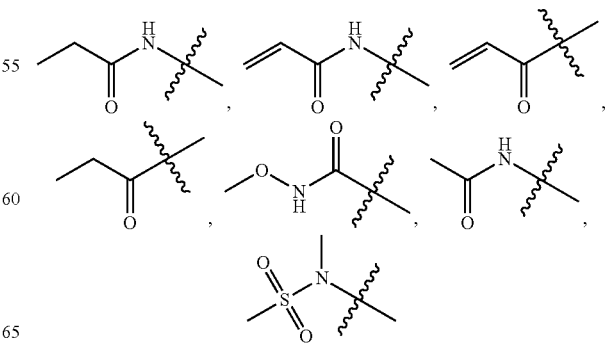

optionally with at least one of $R_1$ and $R_{1'}$ a group comprising an electrophilic moiety, optionally with $R_1$ and $R_{1'}$ jointly form a 4- to 6-membered aliphatic or aromatic cyclic or heterocyclic moiety;

each of $R_2$ and $R_3$ is independently selected from the group consisting of: H, halogen, $C_1$-$C_6$ alkyl, $C_1$-$C_6$ alkoxy, or $R_2$ and $R_3$ jointly form a 5- to 7-membered, aliphatic or aromatic, cyclic or heterocyclic moiety;

each of $R_4$ and $R_5$ is independently selected from H, halogen, $C_1$-$C_6$ alkyl, $C_1$-$C_6$ alkoxy, CN, OH, amino, substituted carboxylic amide, substituted sulfonamide, or $R_4$ and $R_5$ jointly form a 6- to 15-membered aliphatic cyclic or heterocyclic moiety, or a pharmaceutically acceptable form thereof.

In another aspect, the invention generally relates to a pharmaceutical composition comprising an amount of a compound having the structural formula of (I):

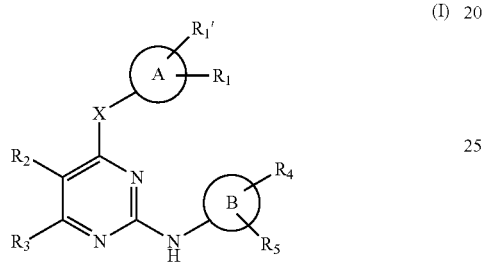

(I)

wherein,

X is $NH(CH_2)_n$, O or S, wherein n is 0 or 1;

A is a 5- to 7-membered, aliphatic or aromatic, cyclic or heterocyclic moiety;

B is a 5- to 7-membered, aliphatic or aromatic, cyclic or heterocyclic moiety;

$R_{1'}$ may be absent and each of $R_1$ and $R_{1'}$ (if present) is independently selected from halogen, $C_1$-$C_6$ alkyl, $C_1$-$C_6$ alkoxy, CN, OH, amino, carboxylic amide, sulfonamide and $R_{1x}$, wherein $R_{1x}$ is selected from:

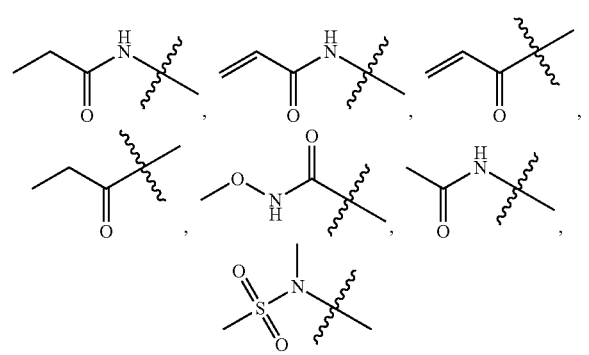

optionally with at least one of $R_1$ and $R_{1'}$ a group comprising an electrophilic moiety, optionally with $R_1$ and $R_{1'}$ jointly form a 4- to 6-membered aliphatic or aromatic cyclic or heterocyclic moiety;

each of $R_2$ and $R_3$ is independently selected from the group consisting of: H, halogen, $C_1$-$C_6$ alkyl, $C_1$-$C_6$ alkoxy, or $R_2$ and $R_3$ jointly form a 5- to 7-membered, aliphatic or aromatic, cyclic or heterocyclic moiety;

each of $R_4$ and $R_5$ is independently selected from H, halogen, $C_1$-$C_6$ alkyl, $C_1$-$C_6$ alkoxy, CN, OH, amino, substituted carboxylic amide, substituted sulfonamide, or $R_4$ and $R_5$ jointly form a 6- to 15-membered aliphatic cyclic or heterocyclic moiety, or a pharmaceutically acceptable form thereof, effective to treat, prevent, or reduce one or more diseases or disorders, in a mammal, including a human, and a pharmaceutically acceptable excipient, carrier, or diluent.

In yet another aspect, the invention generally relates to a unit dosage form comprising a pharmaceutical composition disclosed herein.

In yet another aspect, the invention generally relates to a method for treating, reducing, or preventing a disease or disorder, comprising administering to a subject in need thereof a pharmaceutical composition comprising a compound having the structural formula of (I):

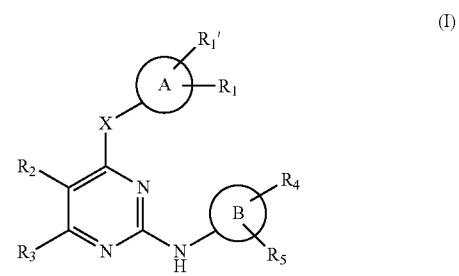

(I)

wherein,

X is $NH(CH_2)_n$, O or S, wherein n is 0 or 1;

A is a 5- to 7-membered, aliphatic or aromatic, cyclic or heterocyclic moiety;

B is a 5- to 7-membered, aliphatic or aromatic, cyclic or heterocyclic moiety;

$R_{1'}$ may be absent and each of $R_1$ and $R_{1'}$ (if present) is independently selected from halogen, $C_1$-$C_6$ alkyl, $C_1$-$C_6$ alkoxy, CN, OH, amino, carboxylic amide, sulfonamide and $R_{1x}$, wherein $R_{1x}$ is selected from:

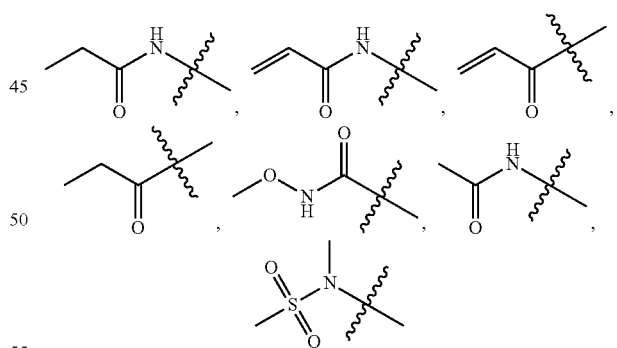

optionally with at least one of $R_1$ and $R_{1'}$ a group comprising an electrophilic moiety, optionally with $R_1$ and $R_{1'}$ jointly form a 4- to 6-membered aliphatic or aromatic cyclic or heterocyclic moiety;

each of $R_2$ and $R_3$ is independently selected from the group consisting of: H, halogen, $C_1$-$C_6$ alkyl, $C_1$-$C_6$ alkoxy, or $R_2$ and $R_3$ jointly form a 5- to 7-membered, aliphatic or aromatic, cyclic or heterocyclic moiety;

each of $R_4$ and $R_5$ is independently selected from H, halogen, $C_1$-$C_6$ alkyl, $C_1$-$C_6$ alkoxy, CN, OH, amino, substituted carboxylic amide, substituted sulfonamide, or $R_4$ and $R_5$ jointly form a 6- to 15-membered aliphatic cyclic or heterocyclic moiety, or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder. The method includes administering to a subject in need thereof a pharmaceutical composition disclosed herein, wherein the disease or disorder is selected from the group consisting of cancer, inflammatory disease, fibrosis, autoimmune disease, or immunologically mediated disease, or a related disease or disorder.

In yet another aspect, the invention generally relates to a method for treating, reducing, or preventing a disease or disorder. The method includes administering to a subject in need thereof a pharmaceutical composition comprising a compound having inhibitory activity to Bruton's tyrosine kinase (BTK) and/or focal adhesion kinase (FAK). In certain embodiments of the method, the compound has the structural formula of (I):

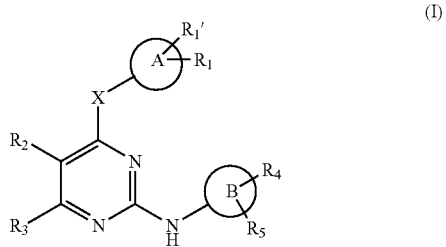

(I)

wherein,

X is $NH(CH_2)_n$, O or S, wherein n is 0 or 1;

A is a 5- to 7-membered, aliphatic or aromatic, cyclic or heterocyclic moiety;

B is a 5- to 7-membered, aliphatic or aromatic, cyclic or heterocyclic moiety;

$R_{1'}$ may be absent and each of $R_1$ and $R_{1'}$ (if present) is independently selected from halogen, $C_1$-$C_6$ alkyl, $C_1$-$C_6$ alkoxy, CN, OH, amino, carboxylic amide, sulfonamide and $R_{1x}$, wherein $R_{1x}$ is selected from:

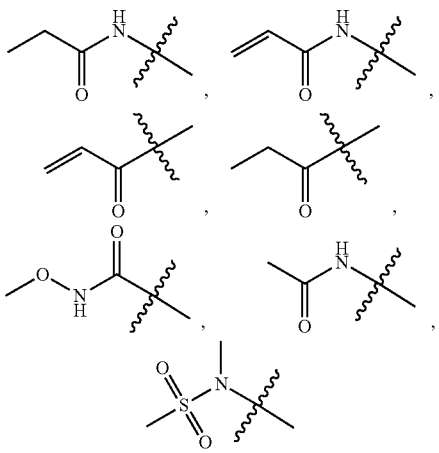

optionally with at least one of $R_1$ and $R_{1'}$ a group comprising an electrophilic moiety, optionally with $R_1$ and $R_{1'}$ jointly form a 4- to 6-membered aliphatic or aromatic cyclic or heterocyclic moiety;

each of $R_2$ and $R_3$ is independently selected from the group consisting of: H, halogen, $C_1$-$C_6$ alkyl, $C_1$-$C_6$ alkoxy, or $R_2$ and $R_3$ jointly form a 5- to 7-membered, aliphatic or aromatic, cyclic or heterocyclic moiety;

each of $R_4$ and $R_5$ is independently selected from H, halogen, $C_1$-$C_6$ alkyl, $C_1$-$C_6$ alkoxy, CN, OH, amino, substituted carboxylic amide, substituted sulfonamide, or $R_4$ and $R_5$ jointly form a 6- to 15-membered aliphatic cyclic or heterocyclic moiety, or a pharmaceutically acceptable form thereof.

In yet another aspect, the invention generally relates to a method for treating, reducing, or preventing a disease or disorder, comprising administering to a subject in need thereof a pharmaceutical composition comprising a compound having the structural formula of:

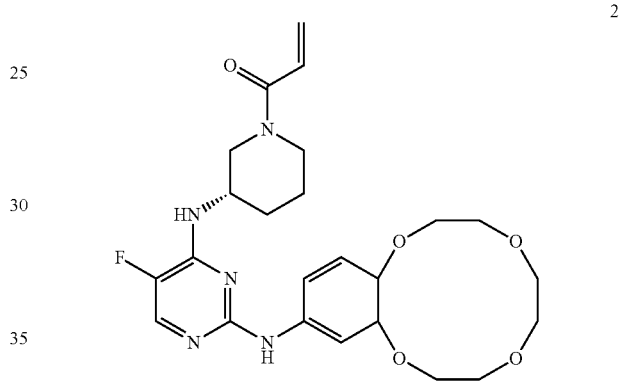

2 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

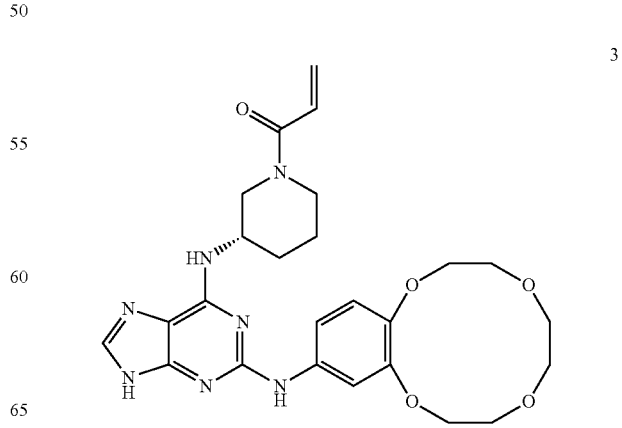

3 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

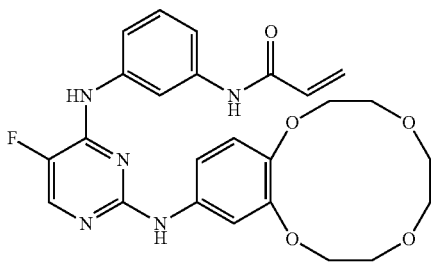

6 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

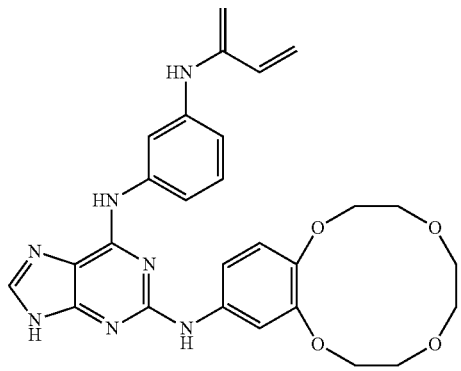

7 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

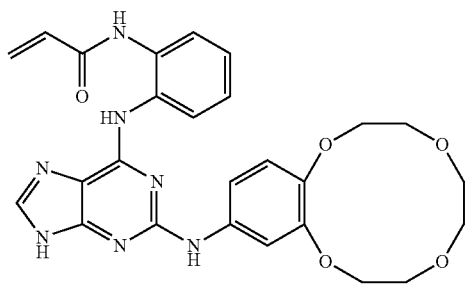

11 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

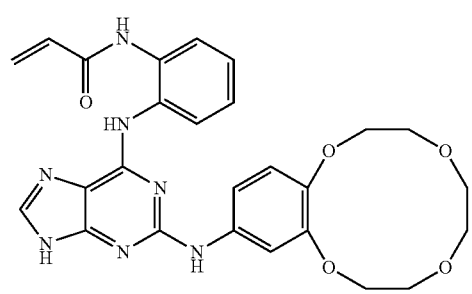

12 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

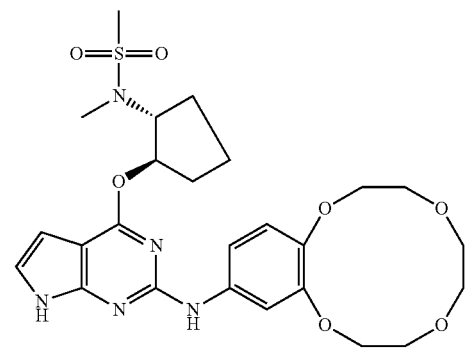

18 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

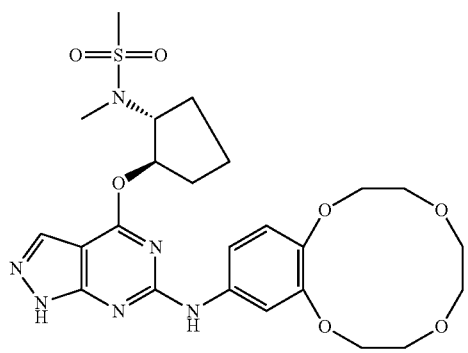

19 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

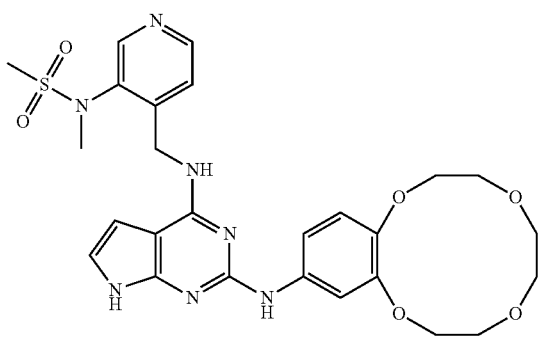

20 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

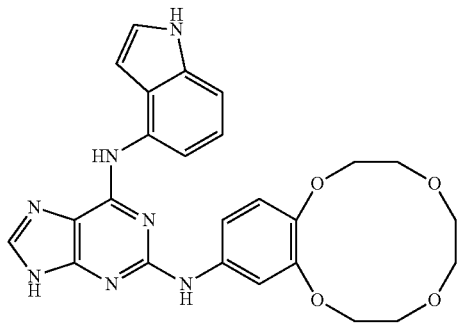

22 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

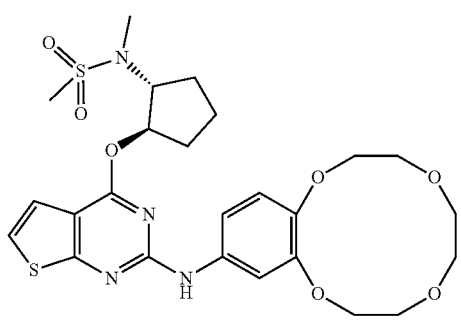

24 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to use of a compound disclosed herein and a pharmaceutically acceptable excipient, carrier, or diluent, in preparation of a medicament for treating a disease or disorder.

BRIEF DESCRIPTION OF THE DRAWINGS

The above and other objects and features of the present invention will become apparent from the following description of the invention, when taken in conjunction with the accompanying drawings, which respectively show:

FIG. 1 shows exemplary Western blotting analysis of p-BTK(Y223) in Ramos cells.
FIG. 2 shows exemplary BTK $IC_{50}$ Data.
FIG. 3 shows exemplary BTK(C481S) $IC_{50}$ Data.
FIG. 4 shows exemplary BMX $IC_{50}$ Data.
FIG. 5 shows exemplary ITK $IC_{50}$ Data.
FIG. 6 shows exemplary FAK $IC_{50}$ Data.
FIG. 7 shows exemplary ERK $IC_{50}$ Data.

DEFINITIONS

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Solvates and polymorphs of the compounds of the invention are also contemplated herein. Solvates of the compounds of the present invention include, for example, hydrates.

Definitions of specific functional groups and chemical terms are described in more detail below. When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo (F, Cl, Br, I), haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$, —OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, —N$(R^a)$C(NR$^a$)N$(R^a)_2$, —N$(R^a)$S(O)$_t$N$(R^a)_2$ (where t is 1 or 2), —P(=O)$(R^a)(R^a)$, or —O—P(=O)(OR$^a)_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "alkoxy" refers to the group —O-alkyl, including from 1 to 10 carbon atoms ($C_{1-10}$) of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-3}$ alkoxy is an alkoxy group that encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$, —OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, —N$(R^a)$C(NR$^a$)N$(R^a)_2$, —N$(R^a)$S(O)$_t$N$(R^a)_2$ (where t is 1 or 2), —P(=O)$(R^a)(R^a)$, or —O—P(=O)(OR$^a)_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., $C_{6-14}$ aromatic or $C_{6-14}$ aryl) that has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —$OR^a$, —$SR^a$, —OC(O)—$R^a$, —N($R^a$)$_2$, —C(O)$R^a$, —C(O)$OR^a$, —OC(O)N($R^a$)$_2$, —C(O)N($R^a$)$_2$, —N($R^a$)C(O)$OR^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)($OR^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "cycloalkyl" and "carbocyclyl" each refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —$OR^a$, —$SR^a$, —OC(O)—$R^a$, —N($R^a$)$_2$, —C(O)$R^a$, —C(O)$OR^a$, —OC(O)N($R^a$)$_2$, —C(O)N($R^a$)$_2$, —N($R^a$)C(O)$OR^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)($OR^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

As used herein, the term "halogen" refers to fluorine (F), chlorine (Cl), bromine (Br), or iodine (I). As used herein, the term "halide" or "halo", means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "heteroalkyl" refers to an alkyl radical, which have one or more skeletal chain atoms selected from an atom other than carbon, e.g., oxygen, nitrogen, sulfur, phosphorus or combinations thereof. A numerical range can be given, e.g., $C_{1-4}$ heteroalkyl, which refers to the chain length in total, which in this example is 4 atoms long. For example, a —$CH_2OCH_2CH_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—$CH_2CH_2OCH_3$), ethoxymethanyl (—$CH_2OCH_2CH_3$), (methoxymethoxy)ethanyl (—CH₂CH₂OCH₂OCH₃), (methoxymethoxy) methanyl (—CH₂OCH₂OCH₃) and (methoxyethoxy)methanyl (—CH₂OCH₂CH₂OCH₃) and the like; amines such as (—CH₂CH₂NHCH₃, —CH₂CH₂N(CH₃)₂, —CH₂NHCH₂CH₃, —CH₂N(CH₂CH₃)(CH₃)) and the like.

As used herein, the term "heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo [h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocyclooctа[d] pyrimidinyl, 5,6,7,8,9,10-hexahydrocyclooctа[d] pyridazinyl, 5,6,7,8,9,10-hexahydrocyclooctа[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5] thieno [2,3-d]pyrimdinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno [2,3-c]pridinyl, and thiophenyl (i.e., thienyl). Unless stated otherwise in the specification, a heteroaryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(Rᵃ)₃, —OW, —SR, —OC(O)—Rᵃ, —N(Rᵃ)₂, —C(O)Rᵃ, —C(O) ORᵃ, —OC(O)N(Rᵃ)₂, —C(O)N(Rᵃ)₂, —N(Rᵃ)C(O)ORᵃ, —N(Rᵃ)C(O)Rᵃ, —N(Rᵃ)C(O)N(Rᵃ)₂, —N(Rᵃ)C(NRᵃ)N (Rᵃ)₂, —N(Rᵃ)S(O)ₜN(Rᵃ)₂ (where t is 1 or 2), —P(=O) (Rᵃ)(Rᵃ), or —O—P(=O)(ORᵃ)₂ where each Rᵃ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the terms "prevent", "preventing", or "prevention" refer to a method for precluding, delaying, averting, or stopping the onset, incidence, severity, or recurrence of a disease or condition. For example, a method is considered to be a prevention if there is a reduction or delay in onset, incidence, severity, or recurrence of a disease or condition or one or more symptoms thereof in a subject susceptible to the disease or condition as compared to a subject not receiving the method. The disclosed method is also considered to be a prevention if there is a reduction or delay in onset, incidence, severity, or recurrence of osteoporosis or one or more symptoms of a disease or condition in a subject susceptible to the disease or condition after receiving the method as compared to the subject's progression prior to receiving treatment. Thus, the reduction or delay in onset, incidence, severity, or recurrence of osteoporosis can be about a 5, 10, 20, 30, 40, 50, 60, 70, 80, 90, 100%, or any amount of reduction in between.

As used herein, a "pharmaceutically acceptable form" of a disclosed compound includes, but is not limited to, pharmaceutically acceptable salts, esters, hydrates, solvates, isomers, prodrugs, and isotopically labeled derivatives thereof. In one embodiment, a "pharmaceutically acceptable form" includes, but is not limited to, pharmaceutically acceptable salts, esters, prodrugs and isotopically labeled derivatives thereof. In some embodiments, a "pharmaceutically acceptable form" includes, but is not limited to, pharmaceutically acceptable isomers and stereoisomers, prodrugs and isotopically labeled derivatives thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoroacetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high performance liquid chromatography.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the term "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that is formulated for administration by inhalation will differ from a low dosage of the same agent formulated for oral administration.

As used herein, the term "high dosage" is meant at least 5% (e.g., at least 10%, 20%, 50%, 100%, 200%, or even 300%) more than the highest standard recommended dosage of a particular compound for treatment of any human disease or condition.

As used herein, the term "prodrug" (or "pro-drug") refers to a pharmacological derivative of a parent drug molecule that requires biotransformation, either spontaneous or enzymatic, within the organism to release the active drug. Such prodrugs are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form.

Prodrug forms often offer advantages of solubility, tissue compatibility, or delayed release in the mammalian organism. (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif, 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability. As such, those of skill in the art will appreciate that certain of the presently disclosed compounds having free amino, arnido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds having a carbonate, carbamate, amide or alkyl ester moiety covalently bonded to any of the above substiruents disclosed herein.

DETAILED DESCRIPTION OF THE INVENTION

The invention provides novel pyrimidine derivatives and analogs that exhibit inhibitory activities towards certain tyrosine kinases, e.g., Bruton's tyrosine kinase (BTK) and/or focal adhesion kinase (FAK), pharmaceutical compositions thereof. Also disclosed herein are methods of treatment, reduction or prevention of certain diseases or conditions mediated by such by tyrosine kinases, e.g., BTK, BTK (C481S), FAK, ERK kinases, and/or other TEC family kinases. Such diseases and conditions include cancers, inflammatory diseases, fibrosis, diabetes, autoimmune diseases, or immunologically mediated diseases.

Tyrosine kinases play an important role in the regulation of various cell processes such as cell proliferation and cell survival. Certain tyrosine kinases are known to become activated by mutation or are abnormally expressed in many human cancers. Selective inhibition of particular tyrosine kinases is useful in the treatment of human diseases such as cancer. The epidermal growth factor receptor (EGFR), for example, is found mutated and/or overexpressed in certain human cancers, such as lung cancer. Several EGFR inhibitors have been approved for treatment of cancers with mutated and/or overexpressed EGFR.

Focal Adhesion Kinase

Focal adhesion kinase (FAK) is a tyrosine kinase that integrates signals from integrins and growth factor receptors, and regulates diverse cellular functions, including adhesion, spreading, migration, invasion, polarity, proliferation, and survival. Studies have shown that FAK is required for tumor initiation and progression, such as in skin tumor and mammary tumor. Overexpression of FAK has been reported in many human tumors (e.g., breast, colon, pancreatic and prostate cancers). FAK is regulated and activated by phosphorylation, particularly on tyrosine residue Y397. In addition, phosphorylated FAK(Y397) is increased in certain tumors, e.g., pancreatic cancer, compared to normal tissues. (McLean et al. 2005 *Nat Rev Cancer* 5(7):505-15; Frame et al. 2010 *Nat Rev Mol Cell Biol.* 11(11):802-14; McLean et al. 2004 *Genes Dev.* 18(24):2998-3003; Lahlou et al. 2007 *Proc Natl Acad Sci USA.* 104(51):20302-7; Owens et al. 1995 *Cancer Res.* 55(13):2752-5; Figel et al. 2011 *Anticancer Agents Med Chem.* 11(7):607-16; Jiang et al. 2016 *Nat Med.* 22(8):851-60.)

Studies have shown that inhibition of FAK by RNAi or a dominant negative FAK induce loss of adhesion and cell death in human cancer cells, e.g. breast, melanoma, and ovarian cancer cells. Inhibition of FAK by shRNA inhibits lung metastasis and increases survival in mouse model. Furthermore, loss of FAK catalytic activity reduces growth of v-Src tumors in mice. (Beviglia et al. 2003 *Biochem J.* 373(Pt 1):201-10; Smith et al. 2005 *Melanoma Res.* 15(5):357-62; Haider et al. 2005 *Clin Cancer Res.* 11(24 Pt 1):8829-36; Mitra et al. 2006 *Oncogene.* 25(32):4429-40.)

Many of FAK's functions in cancer are linked to its role in signaling downstream of integrins and growth factor receptors at the plasma membrane. FAK can localize to the nucleus, and nuclear FAK regulates transcription of inflammatory cytokines and chemokines promoting an immunosuppressive, pro-tumorigenic microenvironment. Suppressing FAK activity may be therapeutically beneficial by triggering immune-mediated tumor regression. (Lim et al. 2008 *Mol Cell.* 29(1):9-22; Serrels et al. 2015 *Cell* 163(1):160-73; Sulzmaier et al. 2014 *Nature Reviews Cancer* 14, 598-610.)

Reported studies have implicated FAK as a central mediator of fibrogenesis. FAK is activated after cutaneous injury. Fibroblast-specific FAK knockout mice have substantially less inflammation and fibrosis than control mice, indicating that FAK plays an important role in fibrosis. Inhibition of FAK resulted in marked abrogation of bleomycin-induced lung fibrosis in mice. FAK is a promising target for therapeutic approaches to fibrotic diseases such as pulmonary fibrosis. (Wong et al. 2011 *Nat Med.* 18(1):148-52; Lagares et al. 2012 *Arthritis Rheum.* 64(5):1653-64; Kinoshita et al. 2013 *Am J Respir Cell Mol Biol.* 49(4):536-43.)

Thus, strong evidence point to FAK as a regulator of adhesion, apoptosis, inhibition of cell growth, migration, angiogenesis, fibrosis, and/or immuno-suppression. Inhibition of FAK activities can be useful for the treatment of FAK related diseases, such as cancer and fibrosis. Currently, there is no FDA approved FAK inhibitors available to treat patients.

Bruton's Tyrosine Kinase

BTK is a kinase encoded by the BTK gene. BTK plays a crucial role in B-cell development and survival, e.g., B-cell activation and B-cell signaling pathway, which links the B-cell receptor (BCR) stimuli to the downstream response in cells. Aberrant B-cell proliferation and differentiation may cause lymphoma, including acute or chronic lymphoid leukemia. (Rawlings 1999 *Clin Immunol.* 91(3):243-53; Khan 2001 *Immunol Res.* 23(2-3):147-56; Hendriks et al. 2014 *Nat Rev Cancer* 14(4):219-32.)

Inhibition of BTK can be a therapeutic approach to treat B-cell mediated diseases, such as B-cell lymphomas and leukemias.

In addition, it has been reported that BTK-dependent immune cell crosstalk drives pancreatic cancer. BTK, as a key B cell and macrophage kinase, regulates T cell-dependent immune responses. Treatment of PDAC-bearing mice with the BTK inhibitor Ibrutinib reprogrammed macrophages toward a TH1 phenotype and suppressed PDAC growth, indicating that BTK signaling mediates PDAC immunosuppression. Pharmacological inhibition of BTK in PDAC can reactivate adaptive immune responses, presenting a new therapeutic modality for this devastating tumor type. (Gunderson et al. 2016 Cancer Discov. 6(3):270-85.)

Effective BTK inhibitors may be useful in the treatment of cancer and rheumatoid arthritis, allergy and asthma. Studies have also shown that BTK signaling is involved in multiple inflammatory, autoimmune diseases and immunity mediated diseases. (Corneth et al. 2016 *Curr Top Microbiol Immunol.* 393:67-105.)

Other TEC family of kinases also play an important role in T-cell activation. ITK is a member of the Tec family tyrosine kinases involved in T-cell receptor signaling, play important roles in T-cell activation and development. ITK inhibitors could be useful in the treatment of diseases such as allergic asthma and atopic dermatitis. (Lucas et al. 2003 *Immunol Rev.* 191:119-38; Schwartzberg et al. 2005 *Nat Rev Immunol.* 5(4):284-95; August et al. 2012 *Int Rev Immunol.* 31(2):155-65.)

Additionally, BMK inhibitors may be useful as anticancer agents. BMX has been shown to be highly expressed in cancer cells, promotes cell proliferation and tumorigenicity, and deletion of BMX inhibits tumor growth (Zhuang et al. 2014 *J Exp Clin Cancer Res.* 33:25; Li et al. 2017 *Oncotarget.* 8(30):49238-49252; Holopainen et al. 2012 *Cancer Res.* 72(14):3512-21.)

Since the TEC family kinases, such as BTK, ITK, BMX, play a critical role in the activation of B-cells and/or T-cells, which are implicated in the pathogenesis of inflammatory diseases, autoimmune diseases, and immunologically mediated diseases, effective inhibition of these kinases provide a promising therapeutic approach to treatment of such diseases.

Ibrutinib, a small molecule BTK inhibitor, has been approved for treatment of a variety of B cell lymphoma and leukemia. However, as data with ibrutinib's use in cancer treatment matures, concerns regarding adverse events and drug resistance have emerged. (Kaur et al. 2017 *Ann Hematol.* 96(7):1175-1184; Furman et al. 2014 *N Engl J Med.* 370(24):2352-4.)

Ibrutinib has been shown to also target EGFR wild type (wt) present in normal cells, which may cause serious side effects such as skin rashes, diarrhea and weight loss. Such side effects have limited ibrutinib's clinical application.

It has now been unexpectedly discovered, as disclosed herein, that certain pyrimidine derivatives can effectively inhibit BTK and/or other TEC family non-receptor tyrosine kinases, e.g., bone marrow tyrosine kinase (BMX) or interleukin-2 inducing T-cell kinase (ITK). In addition, certain pyrimidine derivatives effectively inhibit resistant mutant BTK(C481S) and FAK as well as BTK. Furthermore, certain pyrimidine derivatives effectively inhibit resistant mutant BTK(C481S), FAK, and ERK as well as BTK.

In one aspect, the invention generally relates to a compound having the structural formula of (I):

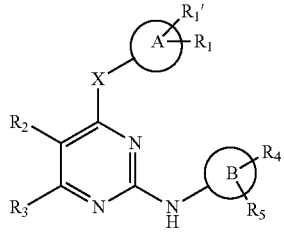

(I)

wherein,

X is $NH(CH_2)_n$, O or S, wherein n is 0 or 1;

A is a 5- to 7-membered, aliphatic or aromatic, cyclic or heterocyclic moiety;

B is a 5- to 7-membered, aliphatic or aromatic, cyclic or heterocyclic moiety;

$R_{1'}$ may be absent and each of $R_1$ and $R_{1'}$ (if present) is independently selected from halogen, $C_1$-$C_6$ alkyl, $C_1$-$C_6$ alkoxy, CN, OH, amino, carboxylic amide, sulfonamide and $R_{1x}$, wherein $R_{1x}$ is selected from:

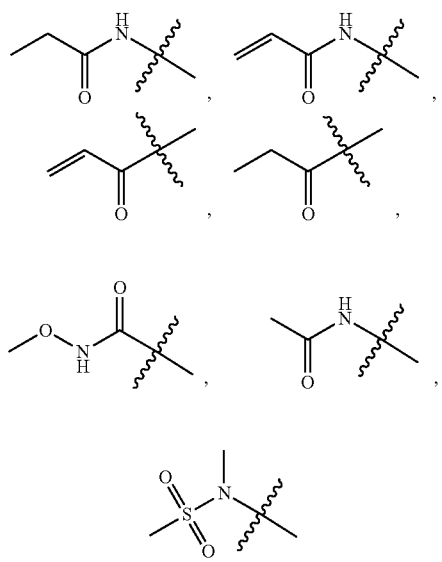

optionally with at least one of $R_1$ and $R_{1'}$ a group comprising an electrophilic moiety, optionally with $R_1$ and $R_{1'}$ jointly form a 4- to 6-membered aliphatic or aromatic cyclic or heterocyclic moiety;

each of $R_2$ and $R_3$ is independently selected from the group consisting of: H, halogen, $C_1$-$C_6$ alkyl, $C_1$-$C_6$ alkoxy, or $R_2$ and $R_3$ jointly form a 5- to 7-membered, aliphatic or aromatic, cyclic or heterocyclic moiety;

each of $R_4$ and $R_5$ is independently selected from H, halogen, $C_1$-$C_6$ alkyl, $C_1$-$C_6$ alkoxy, CN, OH, amino, substituted carboxylic amide, substituted sulfonamide, or $R_4$ and $R_5$ jointly form a 6- to 15-membered aliphatic cyclic or heterocyclic moiety, or a pharmaceutically acceptable form thereof.

In certain embodiments, the compound has the structural formula

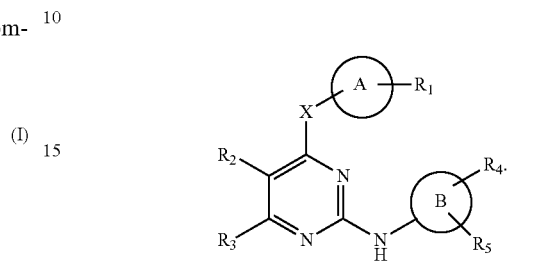

In certain embodiments of structural formula (I), $R_2$ and $R_3$ jointly form a 5-membered ring, having the structural formula (II):

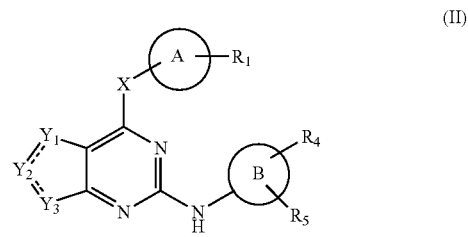

(II)

wherein $Y_1$ is selected from CH, $CH_2$, N, NH, O or S;

$Y_2$ is selected from CH, $CH_2$, N, NH, O or S;

$Y_3$ is selected from CH, $CH_2$, N, NH, O or S; and the bond between $Y_1$ and $Y_2$ may be a double or single bond; the bond between $Y_2$ and $Y_3$ may be double or single bond; provided that at least one $Y_1$, $Y_2$ and $Y_3$ is CH or $CH_2$; and at least one of the bond between $Y_1$ and $Y_2$ and the bond between $Y_2$ and $Y_3$ is a single bond.

In certain embodiments of structural formula (I), B is a six-membered aryl group and the compound has the structural formula of (III):

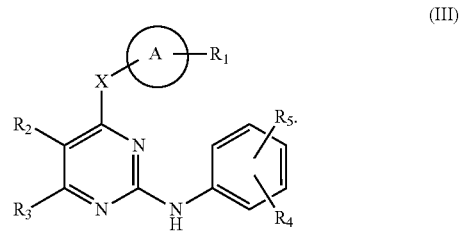

(III)

In certain embodiments of structural formula (III), $R_4$ and $R_5$ are at meta- and para-positions, respectively, having the structural formula (IV):

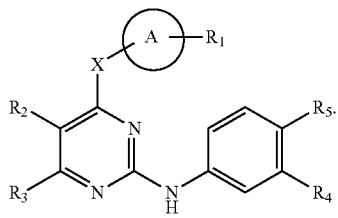
(IV)

In certain embodiments of structural formula (III) or (IV), $R_4$ and $R_5$ jointly form a 6- to 15-membered aliphatic, cyclic or heterocyclic moiety.

In certain embodiments, $R_4$ and $R_5$ jointly form a 12-membered aliphatic heterocyclic moiety.

In certain embodiments, the compound has the following structural formula:

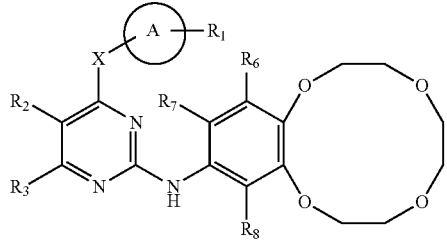
(V)

wherein each of $R_6$, $R_7$ and $R_8$ is independently selected from H, halogen, $C_1$-$C_6$ alkyl, and $C_1$-$C_6$ alkoxy groups.

In certain embodiments, each of $R_5$, $R_7$ and $R_8$ is H and the compound has the structural formula of (V-a):

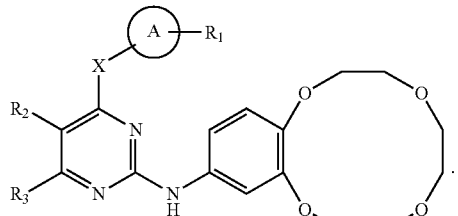
(V-a)

In certain embodiments of structural formula (V), $R_2$ and $R_3$ jointly form a 5-membered heterocyclic aryl moiety, having the structural formula of (VI):

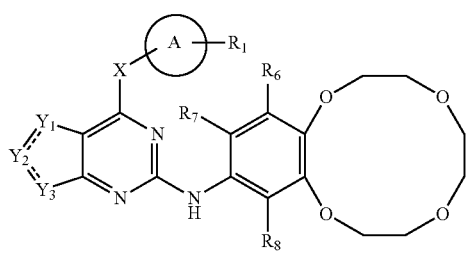
(VI)

wherein
$Y_1$ is selected from CH, $CH_2$, N, NH, O or S;
$Y_2$ is selected from CH, $CH_2$, N, NH, O or S;
$Y_3$ is selected from CH, $CH_2$, N, NH, O or S;
the bond between $Y_1$ and $Y_2$ may be a double or single bond; the bond between $Y_2$ and $Y_3$ may be double or single bond; provided that
at least one $Y_1$, $Y_2$ and $Y_3$ is CH or $CH_2$; and
at least one of the bond between $Y_1$ and $Y_2$ and the bond between $Y_2$ and $Y_3$ is a single bond.

In certain embodiments, each of $R_6$, $R_7$ and $R_8$ is H and the compound has the structural formula of (VI-a):

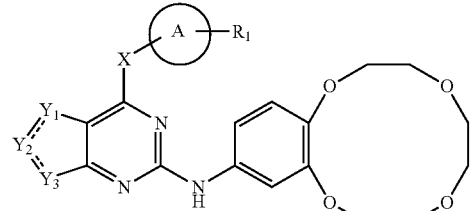
(VI-a)

In certain embodiments, A is a 6-membered aryl moiety, having the structural formula of (VII):

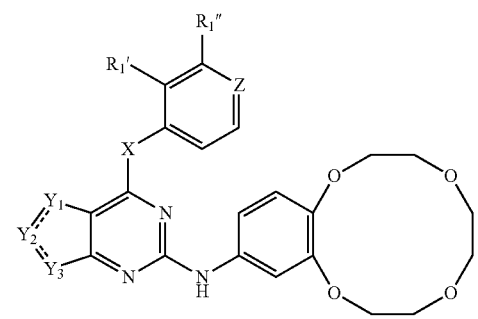
(VII)

wherein
Z is CH or N; and
each of $R_1'$ and $R_1''$ is independently selected from H, halogen, $C_1$-$C_6$ alkyl, OH, or a group comprising an electrophilic moiety, provided that at least one of $R_1'$ and $R_1''$ is a group comprises an electrophilic moiety.

In certain embodiments of structural formula (VII), Z is CH.

In certain embodiments of structural formula (VII), Z is N.

In certain embodiments, A is a 6-membered aliphatic cyclic or heterocyclic moiety, having the structural formula of (VIII):

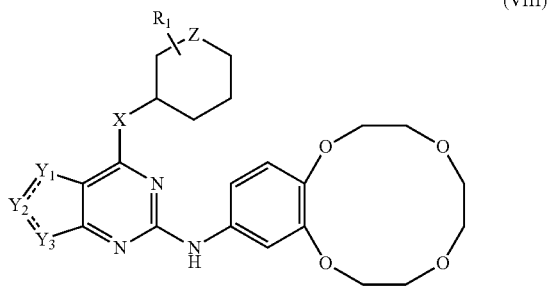

(VIII)

wherein Z is CH or N.

In certain embodiments of structural formula (VIII), Z is CH.

In certain embodiments of structural formula (VIII), Z is N.

In certain embodiments, A is a 5-membered aliphatic cyclic moiety, having the structural formula of (IX):

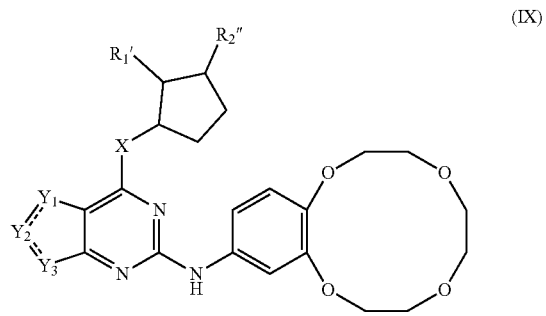

(IX)

each of $R_1'$ and $R_2''$ is independently selected from H, halogen, $C_1$-$C_6$ alkyl, OH, or a group comprising an electrophilic moiety, provided that at least one of $R_1'$ and $R_2'$ is a group comprises an electrophilic moiety.

In certain embodiments of the above compounds, the bond between $Y_1$ and $Y_2$ is a double bond. In certain embodiments of the above compounds, the bond between $Y_1$ and $Y_2$ is a single bond.

In certain embodiments of the above compounds, the bond between $Y_2$ and $Y_3$ is a double bond. In certain embodiments of the above compounds, the bond between $Y_2$ and $Y_3$ is a single bond.

In certain embodiments of the above compounds, $Y_1$ is N; $Y_2$ is CH; and $Y_3$ is NH.

In certain embodiments of the above compounds, $Y_1$ is CH; $Y_2$ is N; and $Y_3$ is NH.

In certain embodiments of the above compounds, $Y_1$ is CH; $Y_2$ is CH; and $Y_3$ is NH.

In certain embodiments of the above compounds, $Y_1$ is CH; $Y_2$ is CH; and $Y_3$ is O or S.

In certain embodiments of the above compounds, X is NH.

In certain embodiments of the above compounds, X is O.

In certain embodiments of the above compounds, X is S.

In certain embodiments of the above compounds, the electrophilic or nucleophilic moiety is an acrylamide ($CH_2$=CH—C(=O)—NH—). In certain embodiments of the above compounds, the electrophilic or nucleophilic moiety is —N—S(=O)$_2$—CH=CH$_2$, —N—C(=O)—CH=CH—CH$_3$, or —N—S(=O)$_2$—CH=CH—CH$_3$.

In certain embodiments, a disclosed compound form irreversible or covalent bonding with a target kinase.

In certain embodiments, a disclosed compound form reversible or non-covalent bonding with a target kinase.

Exemplary compounds of the invention include, but not limited to, those listed in Table 1 below:

TABLE 1

Exemplary Compounds

TABLE 1-continued
Exemplary Compounds
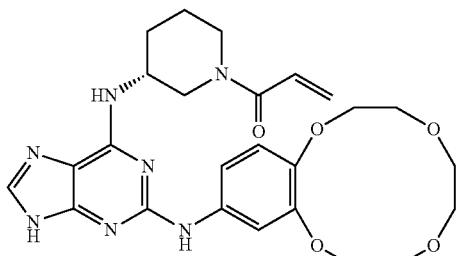
Compound-3
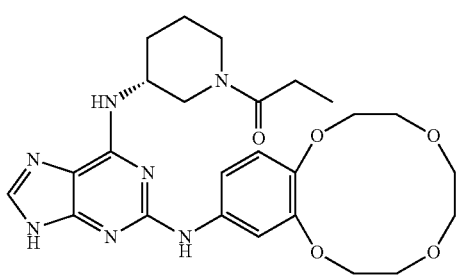 [SMILES: CCC(=O)N1CCC[C@@H](Nc2nc(Nc3ccc4c(c3)OCCOCCOCCO4)nc3[nH]cnc23)C1]
Compound-4
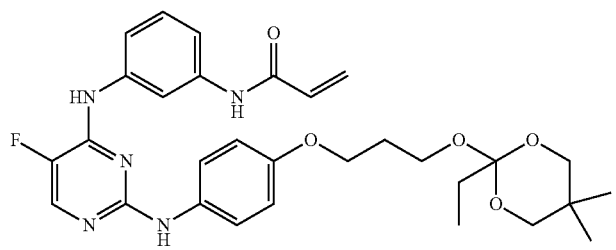 [SMILES: C=CC(=O)Nc1cccc(Nc2nc(Nc3ccc(OCCCOC4(CC)OCC(C)(C)CO4)cc3)ncc2F)c1]
Compound-5
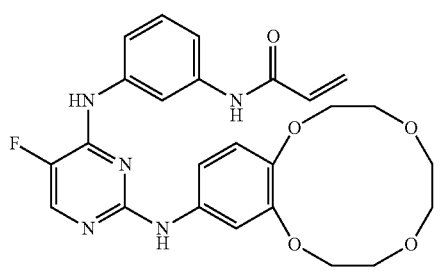 [SMILES: C=CC(=O)Nc1cccc(Nc2nc(Nc3ccc4c(c3)OCCOCCOCCO4)ncc2F)c1]
Compound-6
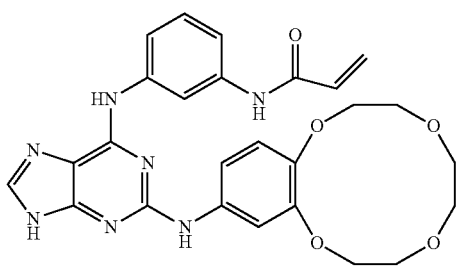 [SMILES: C=CC(=O)Nc1cccc(Nc2nc(Nc3ccc4c(c3)OCCOCCOCCO4)nc3[nH]cnc23)c1]
Compound-7

TABLE 1-continued
Exemplary Compounds
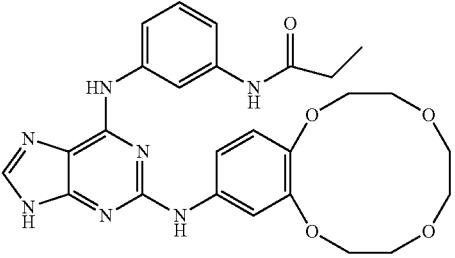 [SMILES: CCC(=O)Nc1cccc(Nc2nc(Nc3ccc4c(c3)OCCOCCOCCO4)nc3[nH]cnc23)c1]
Compound-8
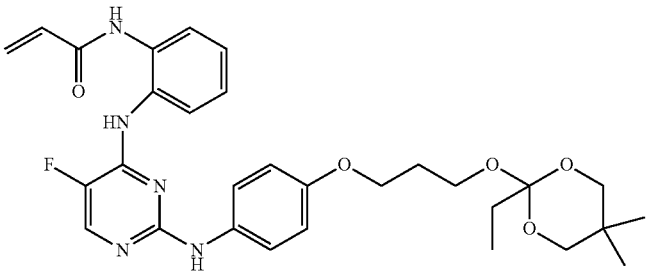 [SMILES: C=CC(=O)Nc1ccccc1Nc1nc(Nc2ccc(OCCCOC3(CC)OCC(C)(C)CO3)cc2)ncc1F]
Compound-9
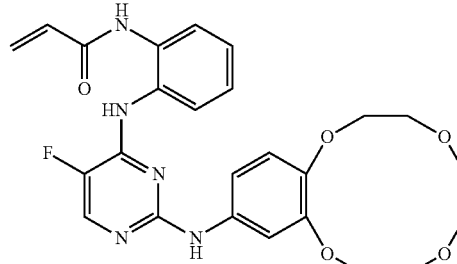
Compound-10
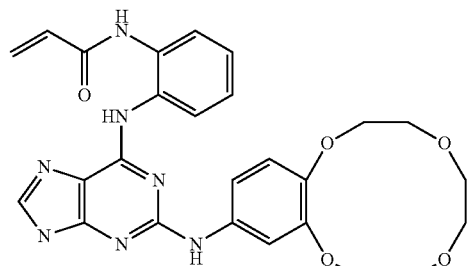
Compound-11
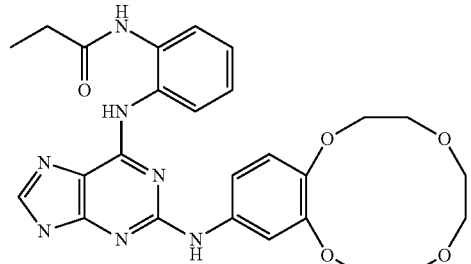
Compound-12

TABLE 1-continued
Exemplary Compounds
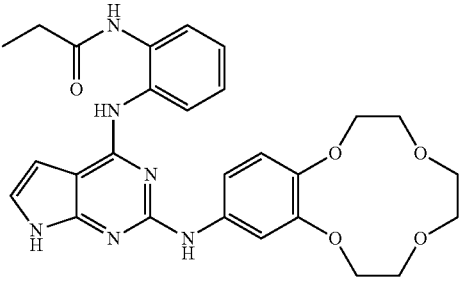 [SMILES: CCC(=O)Nc1ccccc1Nc1nc(Nc2ccc3c(c2)OCCOCCOCCO3)nc2[nH]ccc12]
Compound-13
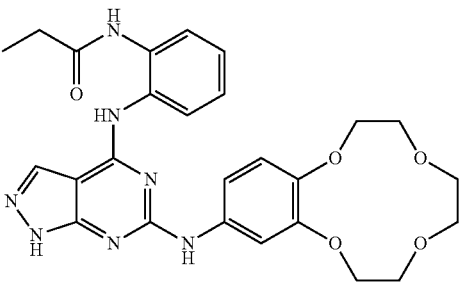 [SMILES: CCC(=O)Nc1ccccc1Nc1nc(Nc2ccc3c(c2)OCCOCCOCCO3)nc2[nH]ncc12]
Compound-14
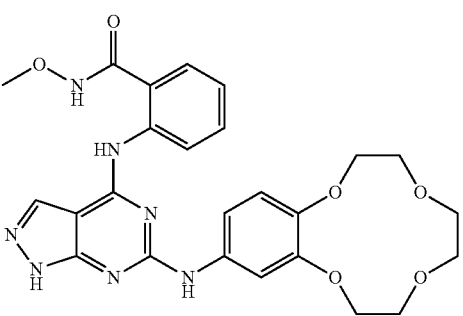 [SMILES: CONC(=O)c1ccccc1Nc1nc(Nc2ccc3c(c2)OCCOCCOCCO3)nc2[nH]ncc12]
Compound-15
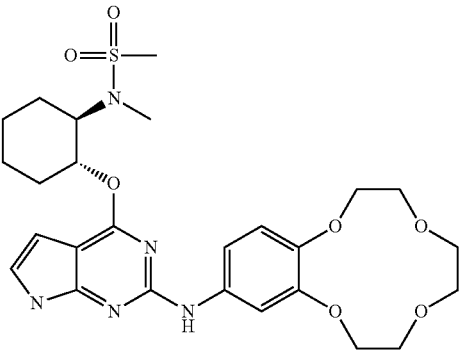 [SMILES: CN([C@@H]1CCCC[C@H]1Oc1nc(Nc2ccc3c(c2)OCCOCCOCCO3)nc2[nH]ccc12)S(C)(=O)=O]
Compound-16
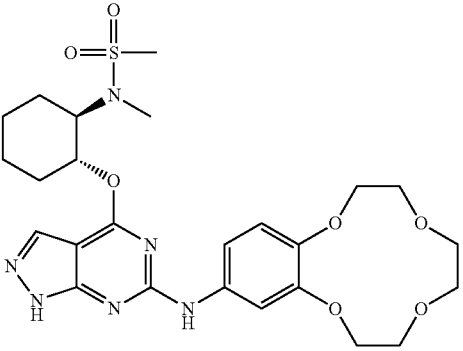 [SMILES: CN([C@@H]1CCCC[C@H]1Oc1nc(Nc2ccc3c(c2)OCCOCCOCCO3)nc2[nH]ncc12)S(C)(=O)=O]
Compound-17

TABLE 1-continued
Exemplary Compounds
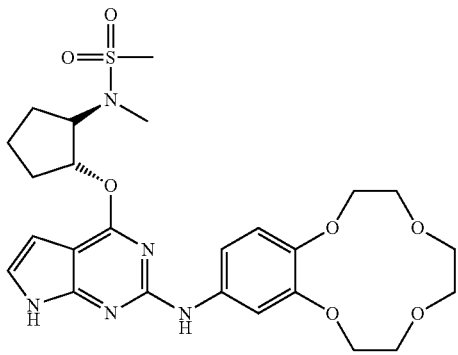
Compound-18
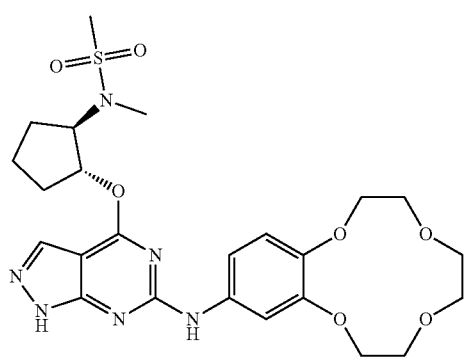 [SMILES: CN([C@@H]1CCC[C@H]1Oc1nc(Nc2ccc3c(c2)OCCOCCOCCO3)nc2[nH]ncc12)S(C)(=O)=O]
Compound-19
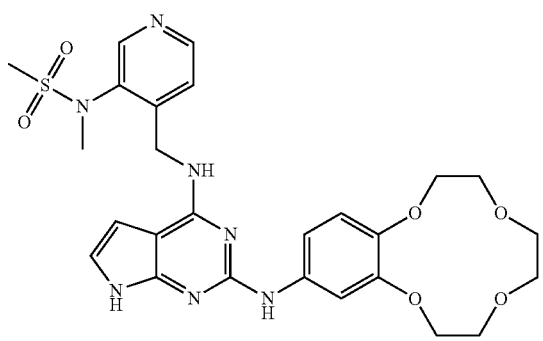 [SMILES: CN(c1cnccc1CNc1nc(Nc2ccc3c(c2)OCCOCCOCCO3)nc2[nH]ccc12)S(C)(=O)=O]
Compound-20
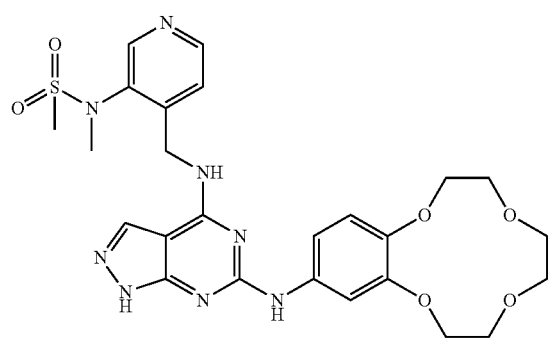 [SMILES: CN(c1cnccc1CNc1nc(Nc2ccc3c(c2)OCCOCCOCCO3)nc2[nH]ncc12)S(C)(=O)=O]
Compound-21

TABLE 1-continued
Exemplary Compounds
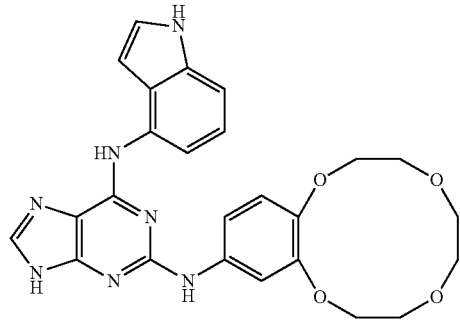 [SMILES: c1cc(Nc2nc(Nc3ccc4c(c3)OCCOCCOCCO4)nc3[nH]cnc23)c2cc[nH]c2c1]
Compound-22
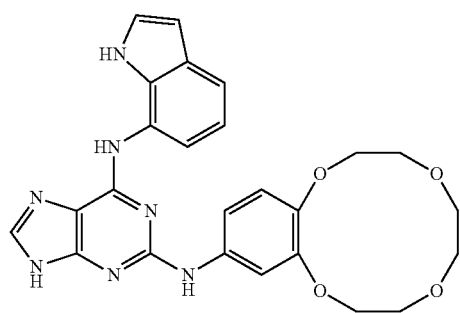 [SMILES: c1cc(Nc2nc(Nc3ccc4c(c3)OCCOCCOCCO4)nc3[nH]cnc23)c2[nH]ccc2c1]
Compound-23
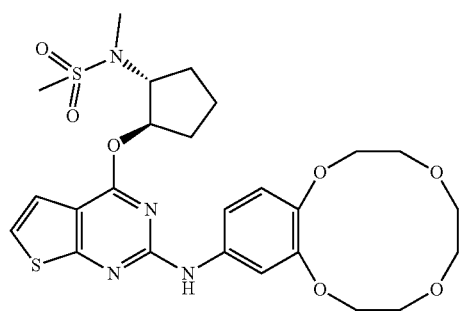 [SMILES: CN([C@@H]1CCC[C@H]1Oc1nc(Nc2ccc3c(c2)OCCOCCOCCO3)nc2sccc12)S(C)(=O)=O]
Compound-24
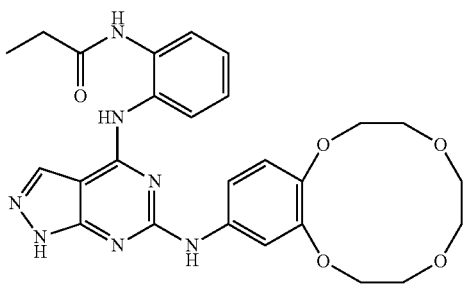 [SMILES: CCC(=O)Nc1ccccc1Nc1nc(Nc2ccc3c(c2)OCCOCCOCCO3)nc2[nH]ncc12]
Compound-26
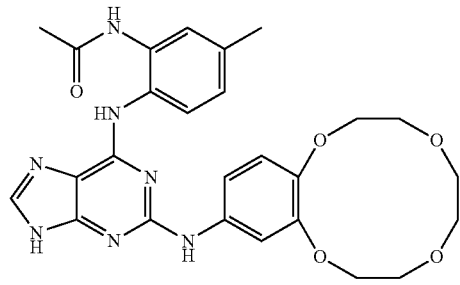 [SMILES: CC(=O)Nc1cc(C)ccc1Nc1nc(Nc2ccc3c(c2)OCCOCCOCCO3)nc2[nH]cnc12]
Compound-27

TABLE 1-continued
Exemplary Compounds
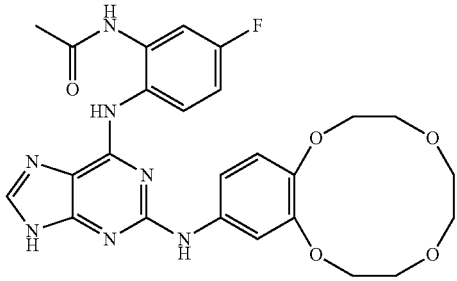 [SMILES: CC(=O)Nc1cc(F)ccc1Nc1nc(Nc2ccc3c(c2)OCCOCCOCCO3)nc2[nH]cnc12]
Compound-28
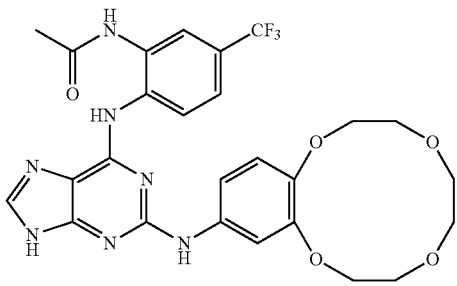 [SMILES: CC(=O)Nc1cc(C(F)(F)F)ccc1Nc1nc(Nc2ccc3c(c2)OCCOCCOCCO3)nc2[nH]cnc12]
Compound-29
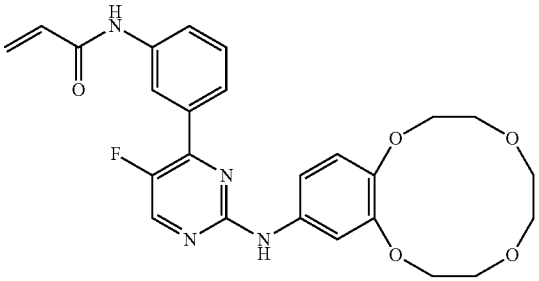 [SMILES: C=CC(=O)Nc1cccc(-c2nc(Nc3ccc4c(c3)OCCOCCOCCO4)ncc2F)c1]
Compound-30
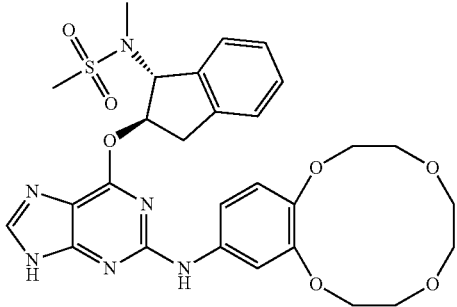 [SMILES: CN([C@@H]1c2ccccc2C[C@H]1Oc1nc(Nc2ccc3c(c2)OCCOCCOCCO3)nc2[nH]cnc12)S(C)(=O)=O]
Compound-31
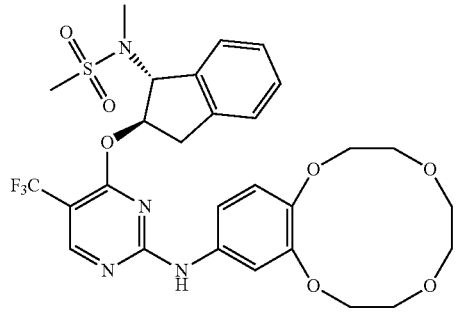 [SMILES: CN([C@@H]1c2ccccc2C[C@H]1Oc1nc(Nc2ccc3c(c2)OCCOCCOCCO3)ncc1C(F)(F)F)S(C)(=O)=O]
Compound-32

In certain embodiments, the compound has structural formula of:

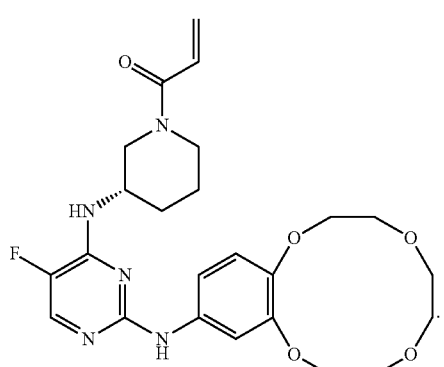

2

In certain embodiments, the compound has structural formula of:

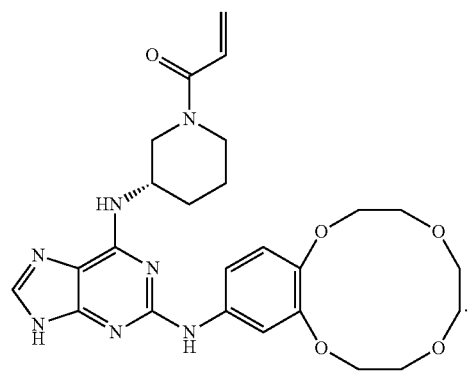

3

In certain embodiments, the compound has structural formula of:

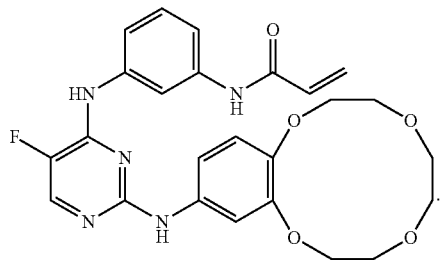

6

In certain embodiments, the compound has structural formula of:

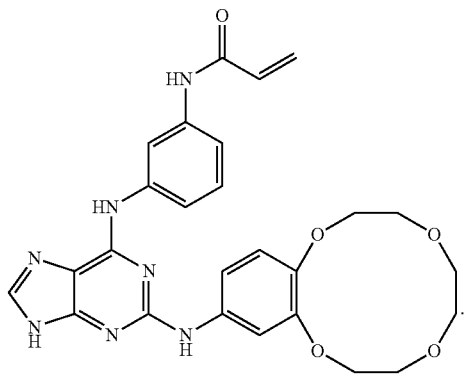

5

7

In certain embodiments, the compound has structural formula of:

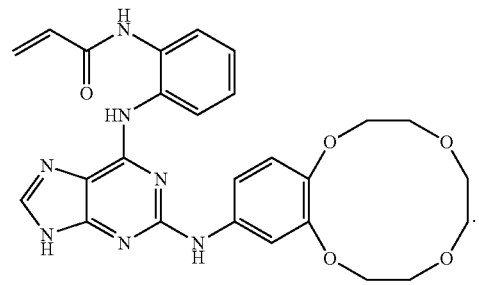

11

In certain embodiments, the compound as structural formula of:

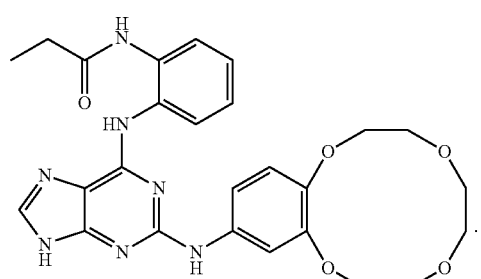

12

In certain embodiments, the compound has structural formula of:

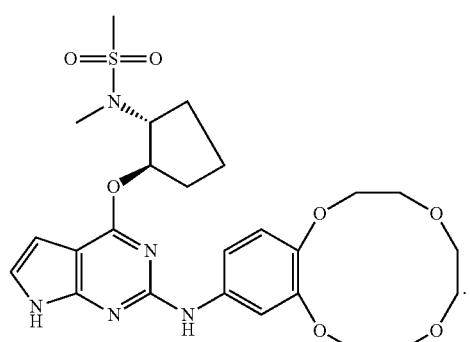

18

In certain embodiments, the compound has structural formula of:

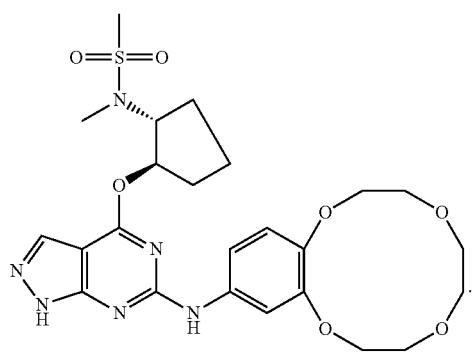

19

In certain embodiments, the compound has structural formula of:

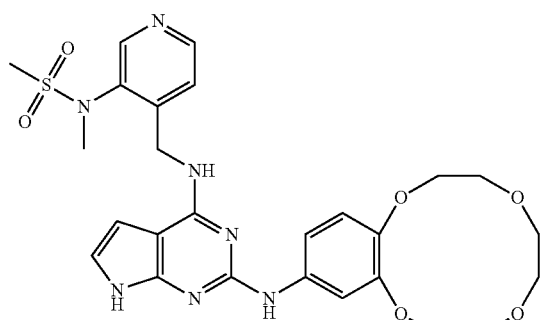

20

In certain embodiments, the compound has structural formula of:

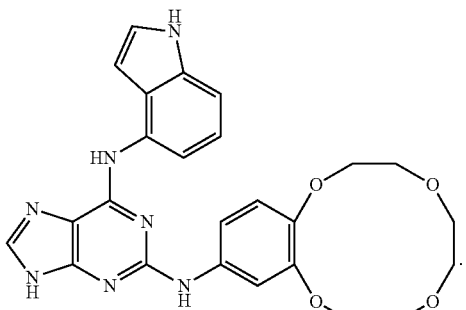

22

In certain embodiments, the compound has structural formula of:

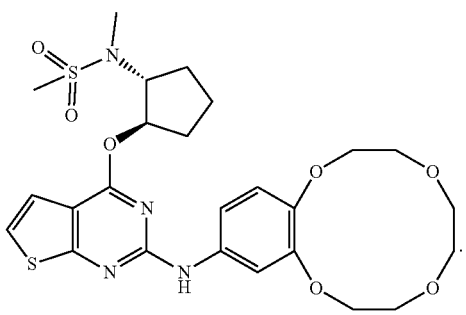

24

In certain embodiments, the compound has structural formula of:

Compound-26

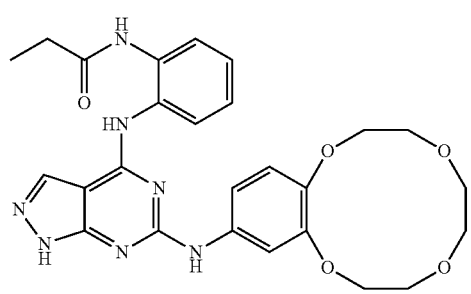

In certain embodiments, the compound has structural formula of:

Compound-27

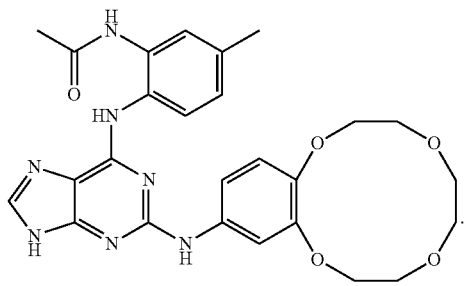

In certain embodiments, the compound has structural formula of:

Compound-28

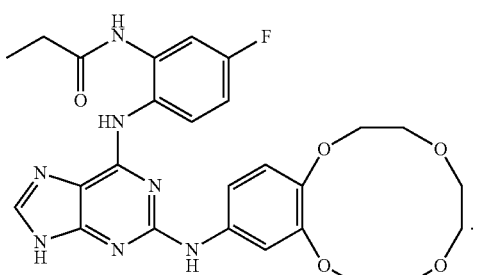

In certain embodiments, the compound has structural formula of:

Compound-29

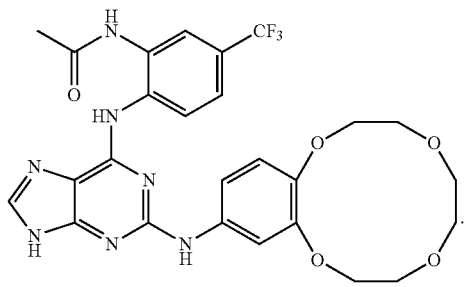

In certain embodiments, the compound has structural formula of:

Compound-30

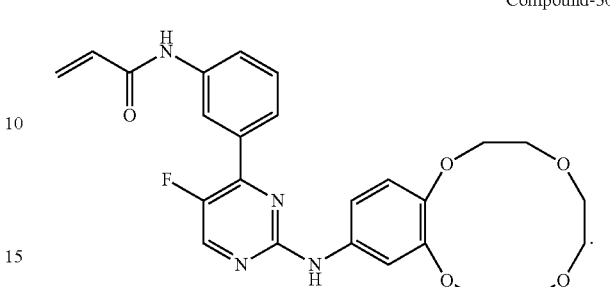

In certain embodiments, the compound has structural formula of:

Compound-31

In certain embodiments, the compound has structural formula of:

Compound-32

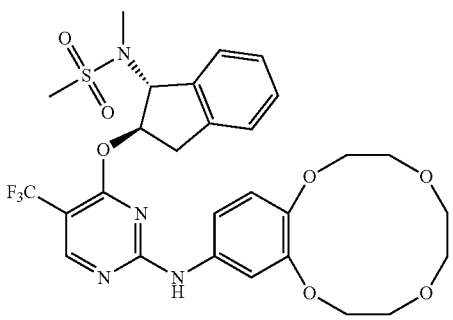

In another aspect, the invention generally relates to a pharmaceutical composition comprising an amount of a compound having the structural formula of (I):

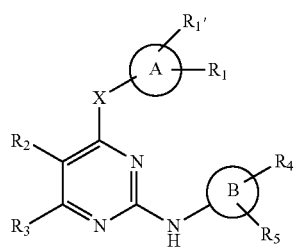

(I)

wherein,
X is $NH(CH_2)_n$, O or S, wherein n is 0 or 1;
A is a 5- to 7-membered, aliphatic or aromatic, cyclic or heterocyclic moiety;
B is a 5- to 7-membered, aliphatic or aromatic, cyclic or heterocyclic moiety;
$R_{1'}$ may be absent and each of $R_1$ and $R_{1'}$ (if present) is independently selected from halogen, $C_1$-$C_6$ alkyl, $C_1$-$C_6$ alkoxy, CN, OH, amino, carboxylic amide, sulfonamide and $R_{1x}$, wherein $R_{1x}$ is selected from:

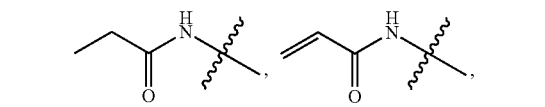

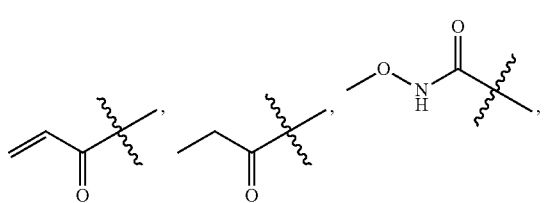

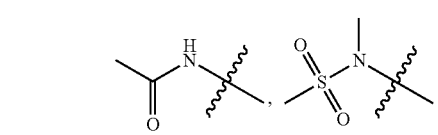

optionally with at least one of $R_1$ and $R_{1'}$ a group comprising an electrophilic moiety, optionally with $R_1$ and $R_{1'}$ jointly form a 4- to 6-membered aliphatic or aromatic cyclic or heterocyclic moiety
each of $R_2$ and $R_3$ is independently selected from the group consisting of: H, halogen, $C_1$-$C_6$ alkyl, $C_1$-$C_6$ alkoxy, or $R_2$ and $R_3$ jointly form a 5- to 7-membered, aliphatic or aromatic, cyclic or heterocyclic moiety;
each of $R_4$ and $R_5$ is independently selected from H, halogen, $C_1$-$C_6$ alkyl, $C_1$-$C_6$ alkoxy, CN, OH, amino, substituted carboxylic amide, substituted sulfonamide, or $R_4$ and $R_5$ jointly form a 6- to 15-membered aliphatic cyclic or heterocyclic moiety,
or a pharmaceutically acceptable form thereof, effective to treat, prevent, or reduce one or more diseases or disorders, in a mammal, including a human, and a pharmaceutically acceptable excipient, carrier, or diluent.

In certain embodiments, the pharmaceutical composition is effective for treating, preventing, or reducing cancer, or a related disease or disorder.

In certain embodiments, the pharmaceutical composition is effective for treating, preventing, or reducing an inflammatory disease, or a related disease or disorder.

In certain embodiments, the pharmaceutical composition is effective for treating, preventing, or reducing fibrosis, or a related disease or disorder.

In certain embodiments, the pharmaceutical composition is effective for treating, preventing, or reducing an autoimmune disease, or a related disease or disorder.

In certain embodiments, the pharmaceutical composition is effective for treating, preventing, or reducing an immunologically mediated disease, or a related disease or disorder.

The pharmaceutical composition of the invention encompasses a pharmaceutical composition comprising any compound of the invention.

In certain embodiments of the pharmaceutical composition, the compound has the structural formula of:

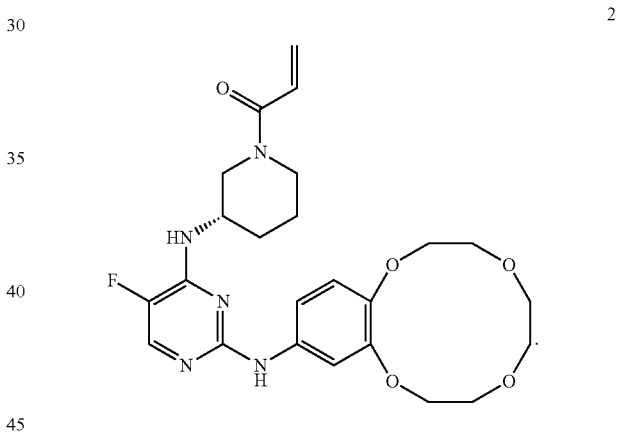

2

In certain embodiments of the pharmaceutical composition, the compound has the structural formula of:

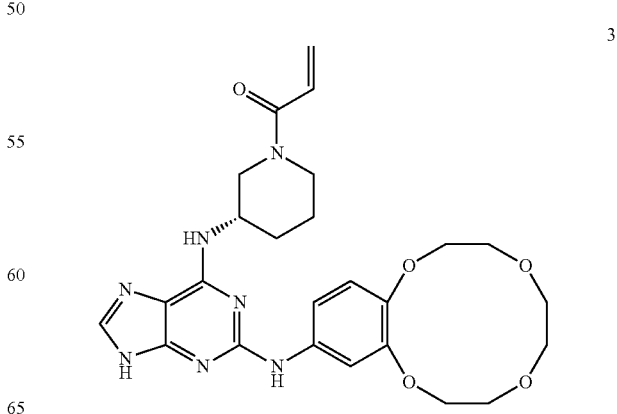

3

In certain embodiments of the pharmaceutical composition, the compound has the structural formula of:

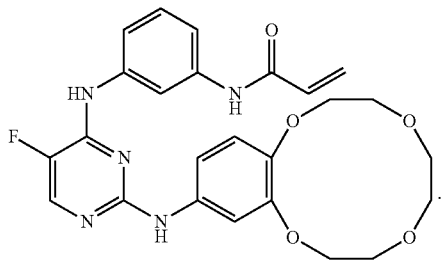

6

In certain embodiments of the pharmaceutical composition, the compound has the structural formula of:

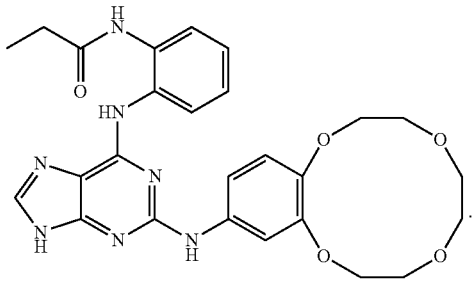

12

In certain embodiments of the pharmaceutical composition, the compound has the structural formula of:

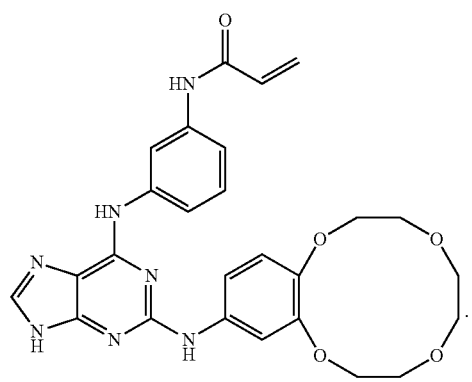

7

In certain embodiments of the pharmaceutical composition, the compound has the structural formula of:

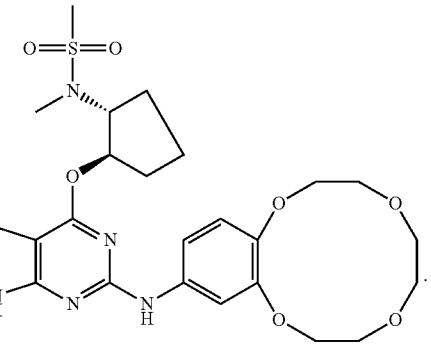

18

In certain embodiments of the pharmaceutical composition, the compound has the structural formula of:

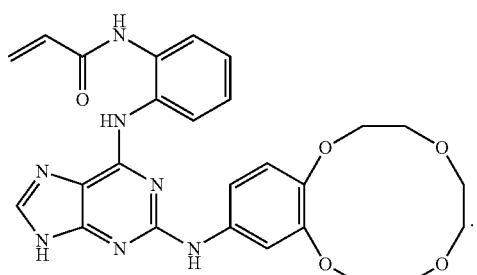

11

In certain embodiments of the pharmaceutical composition, the compound has the structural formula of:

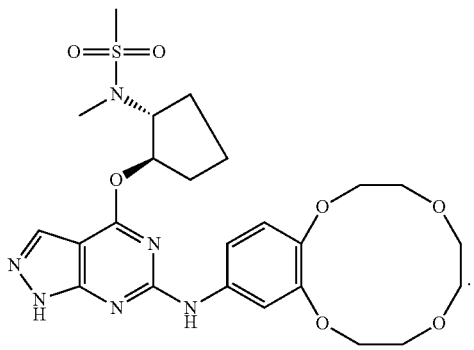

19

In certain embodiments of the pharmaceutical composition, the compound has the structural formula of:

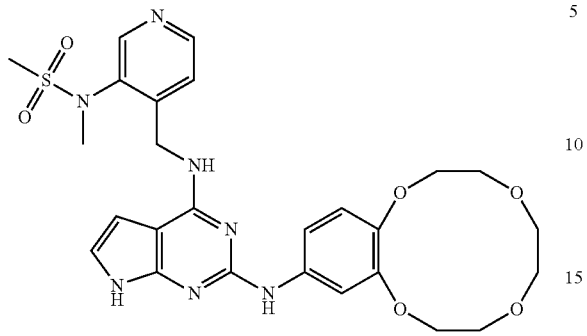

In certain embodiments of the pharmaceutical composition, the compound has structural formula of:

Compound-26

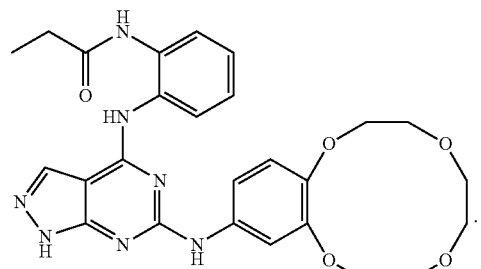

In certain embodiments of the pharmaceutical composition, the compound has the structural formula of:

22

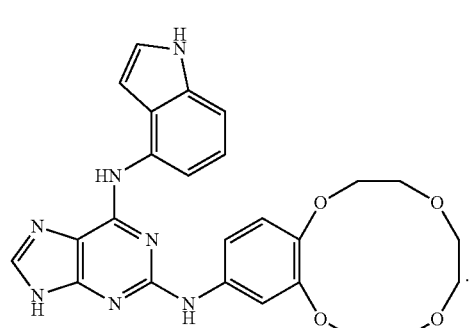

In certain embodiments of the pharmaceutical composition, the compound has structural formula of:

Compound-27

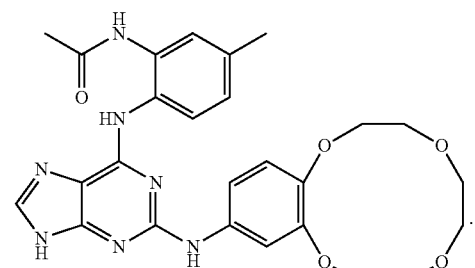

In certain embodiments of the pharmaceutical composition, the compound has the structural formula of:

24

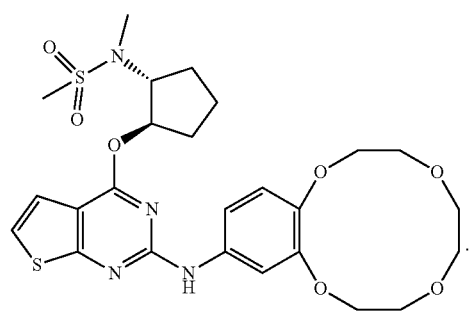

In certain embodiments of the pharmaceutical composition, the compound has structural formula of:

Compound-28

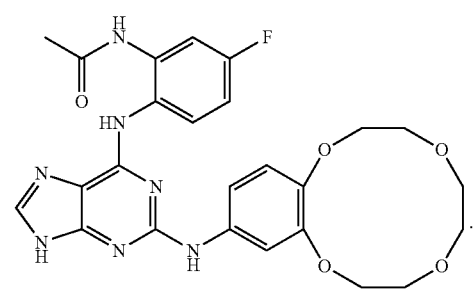

In certain embodiments of the pharmaceutical composition, the compound has structural formula of:

Compound-29

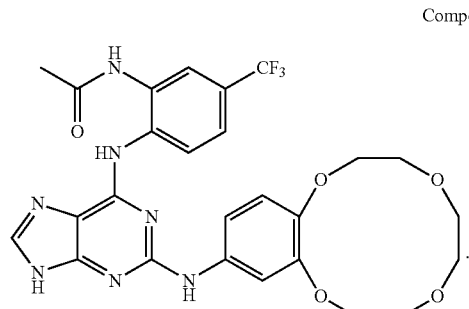

In certain embodiments of the pharmaceutical composition, the compound has structural formula of:

Compound-30

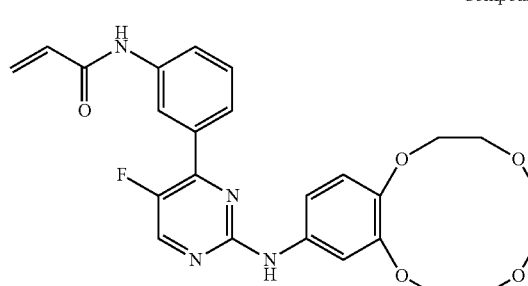

In certain embodiments of the pharmaceutical composition, the compound has structural formula of:

Compound-31

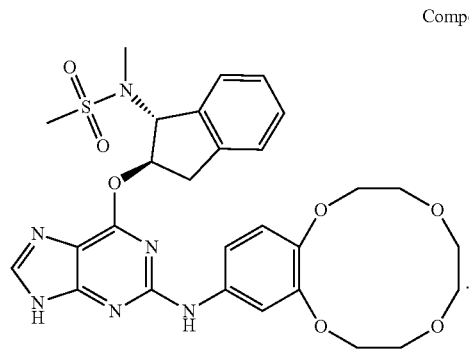

In certain embodiments of the pharmaceutical composition, the compound has structural formula of:

Compound-32

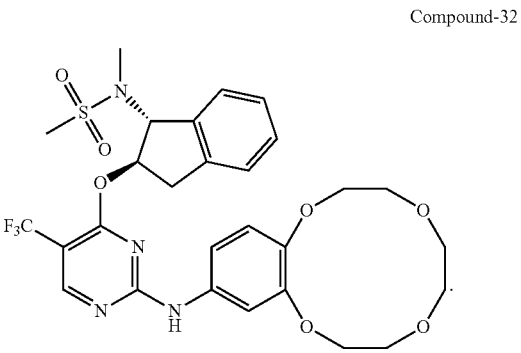 [SMILES: CN([C@@H]1c2ccccc2C[C@H]1Oc1nc(Nc2ccc3c(c2)OCCOCCOCCO3)ncc1C(F)(F)F)S(C)(=O)=O]

In yet another aspect, the invention generally relates to a unit dosage form comprising a pharmaceutical composition disclosed herein.

In yet another aspect, the invention generally relates to a method for treating, reducing, or preventing a disease or disorder, comprising administering to a subject in need thereof a pharmaceutical composition comprising a compound having the structural formula of (I):

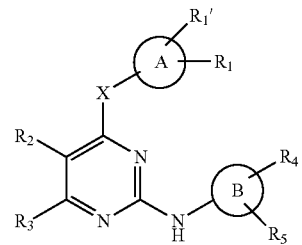

(I)

wherein,
X is $NH(CH_2)_n$, O or S, wherein n is 0 or 1;
A is a 5- to 7-membered, aliphatic or aromatic, cyclic or heterocyclic moiety;
B is a 5- to 7-membered, aliphatic or aromatic, cyclic or heterocyclic moiety;
$R_{1'}$ may be absent and each of $R_1$ and $R_{1'}$ (if present) is independently selected from halogen, $C_1$-$C_6$ alkyl, $C_1$-$C_6$ alkoxy, CN, OH, amino, carboxylic amide, sulfonamide and $R_{1x}$, wherein $R_{1x}$ is selected from:

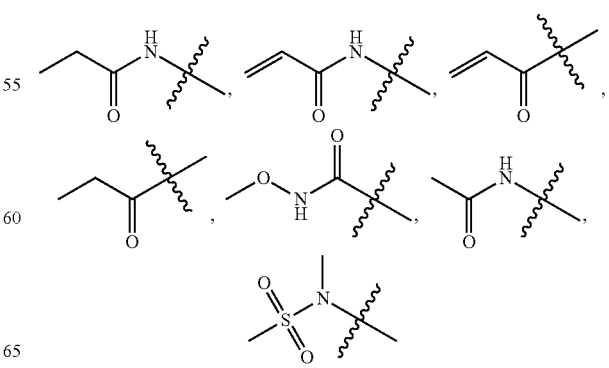

optionally with at least one of $R_1$ and $R_{1'}$ a group comprising an electrophilic moiety, optionally with $R_1$ and $R_{1'}$ jointly form a 4- to 6-membered aliphatic or aromatic cyclic or heterocyclic moiety;

each of $R_2$ and $R_3$ is independently selected from the group consisting of: H, halogen, $C_1$-$C_6$ alkyl, $C_1$-$C_6$ alkoxy, or $R_2$ and $R_3$ jointly form a 5- to 7-membered, aliphatic or aromatic, cyclic or heterocyclic moiety;

each of $R_4$ and $R_5$ is independently selected from H, halogen, $C_1$-$C_6$ alkyl, $C_1$-$C_6$ alkoxy, CN, OH, amino, substituted carboxylic amide, substituted sulfonamide, or $R_4$ and $R_5$ jointly form a 6- to 15-membered aliphatic cyclic or heterocyclic moiety, or a pharmaceutically acceptable form thereof, effective to treat, prevent, or reduce one or more of cancer, inflammatory disease, fibrosis, autoimmune disease, or immunologically mediated disease, or a related disease or disorder thereof, in a mammal, including a human, and a pharmaceutically acceptable excipient, carrier, or diluent.

In certain embodiments, the method is effective to treat, prevent, or reduce cancer, or a related disease or disorder.

In certain embodiments, the method is effective to treat, prevent, or reduce an inflammatory disease, or a related disease or disorder.

In certain embodiments, the method is effective to treat, prevent, or reduce fibrosis, or a related disease or disorder.

In certain embodiments, the method is effective to treat, prevent, or reduce an autoimmune disease, or a related disease or disorder.

In certain embodiments, the method is effective to treat, prevent, or reduce an immunologically mediated disease, or a related disease or disorder.

In yet another aspect, the invention generally relates to a method for treating, reducing, or preventing a disease or disorder. The method includes administering to a subject in need thereof a pharmaceutical composition disclosed herein, wherein the disease or disorder is selected from the group consisting of cancer, inflammatory disease, fibrosis, autoimmune disease, or immunologically mediated disease, or a related disease or disorder.

In yet another aspect, the invention generally relates to a method for treating, reducing, or preventing a disease or disorder. The method includes administering to a subject in need thereof a pharmaceutical composition comprising a compound having inhibitory activity to Bruton's tyrosine kinase (BTK) and/or focal adhesion kinase (FAK).

In certain embodiments of the method, the compound is an inhibitor of BTK.

In certain embodiments of the method, the compound is an inhibitor of bone marrow tyrosine kinase (BMX).

In certain embodiments of the method, the compound is an inhibitor of both BTK and BMX.

In certain embodiments of the method, the compound is an inhibitor of interleukin-2 inducing T-cell kinase (ITK).

In certain embodiments of the method, the compound is an inhibitor of FAK.

In certain embodiments of the method, the compound is an inhibitor of BTK and of FAK.

In certain embodiments of the method, the compound is an inhibitor of BTK (C481S) mutant.

In certain embodiments of the method, the compound is an inhibitor of ERK.

In certain embodiments of the method, the compound is an inhibitor of BTK, BTK (C481S) mutant, and FAK.

In certain embodiments of the method, the compound is an inhibitor of BTK, BTK (C481S) mutant, FAK and ERK.

In certain embodiments of the method, the compound has the structural formula of (I):

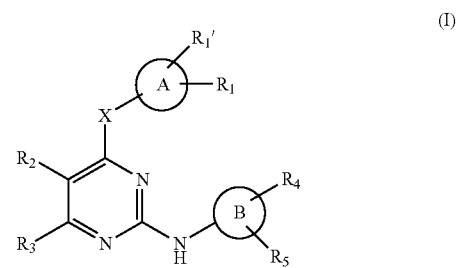

wherein,

X is $NH(CH_2)_n$, O or S, wherein n is 0 or 1;

A is a 5- to 7-membered, aliphatic or aromatic, cyclic or heterocyclic moiety;

B is a 5- to 7-membered, aliphatic or aromatic, cyclic or heterocyclic moiety;

$R_{1'}$ may be absent and each of $R_1$ and $R_{1'}$ (if present) is independently selected from halogen, $C_1$-$C_6$ alkyl, $C_1$-$C_6$ alkoxy, CN, OH, amino, carboxylic amide, sulfonamide and $R_{1x}$, wherein $R_{1x}$ is selected from:

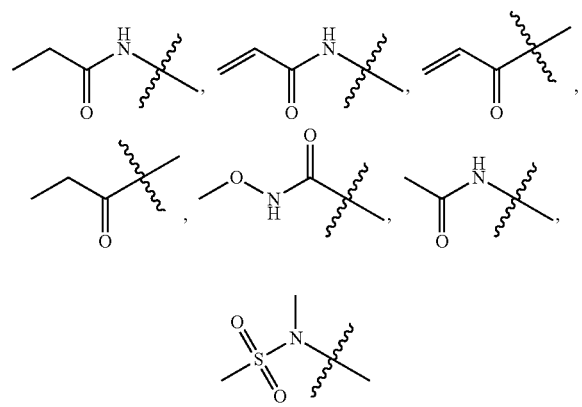

optionally with at least one of $R_1$ and $R_{1'}$ a group comprising an electrophilic moiety, optionally with $R_1$ and $R_{1'}$ jointly form a 4- to 6-membered aliphatic or aromatic cyclic or heterocyclic moiety;

each of $R_2$ and $R_3$ is independently selected from the group consisting of: H, halogen, $C_1$-$C_6$ alkyl, $C_1$-$C_6$ alkoxy, or $R_2$ and $R_3$ jointly form a 5- to 7-membered, aliphatic or aromatic, cyclic or heterocyclic moiety;

each of $R_4$ and $R_5$ is independently selected from H, halogen, $C_1$-$C_6$ alkyl, $C_1$-$C_6$ alkoxy, CN, OH, amino, substituted carboxylic amide, substituted sulfonamide, or $R_4$ and $R_5$ jointly form a 6- to 15-membered aliphatic cyclic or heterocyclic moiety, or a pharmaceutically acceptable form thereof.

In yet another aspect, the invention generally relates to a method for treating, reducing, or preventing a disease or disorder, comprising administering to a subject in need thereof a pharmaceutical composition comprising a compound having the structural formula of:

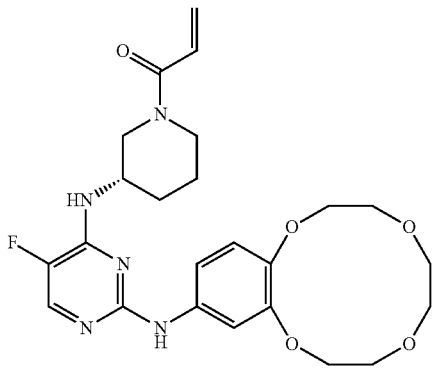

2 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

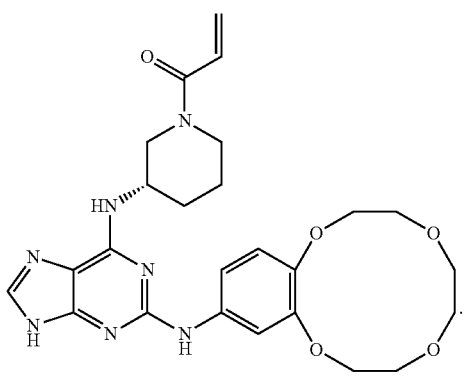

3 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

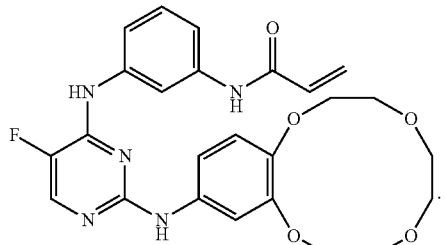

6 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

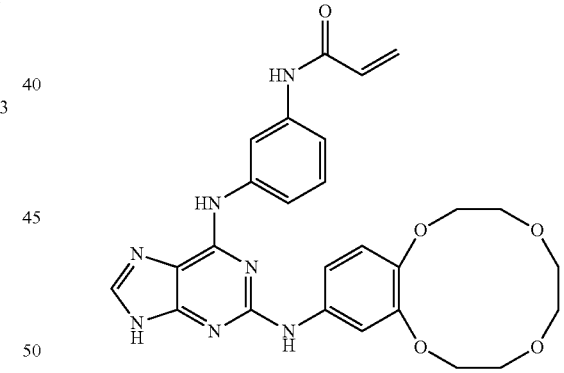

7 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

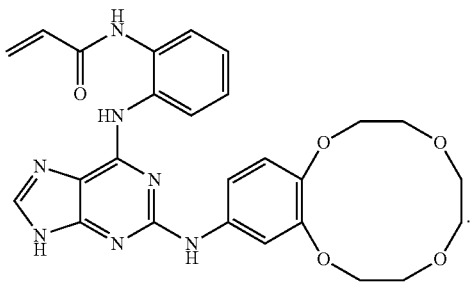

11 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

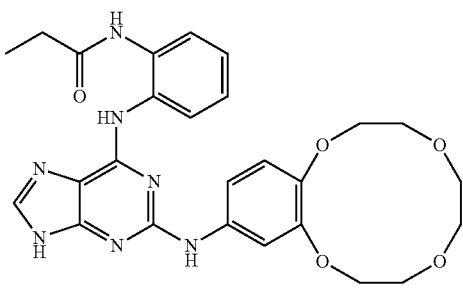

12 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

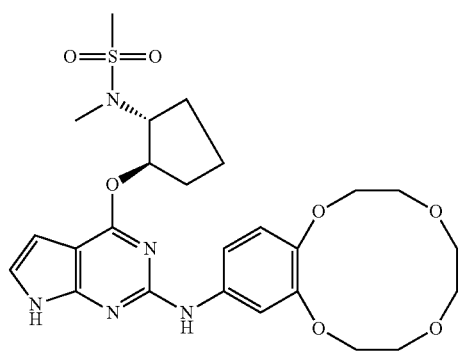

18 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

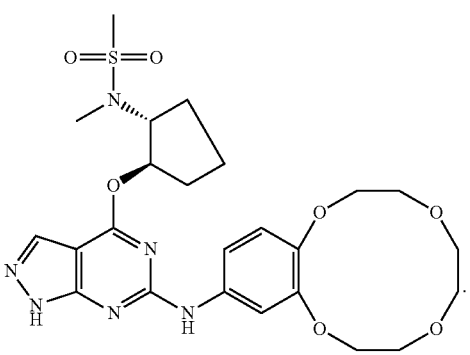

19 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

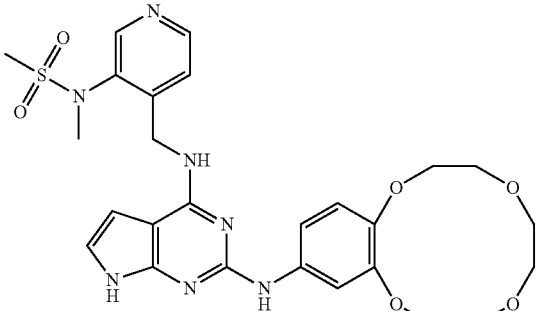

20 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

22

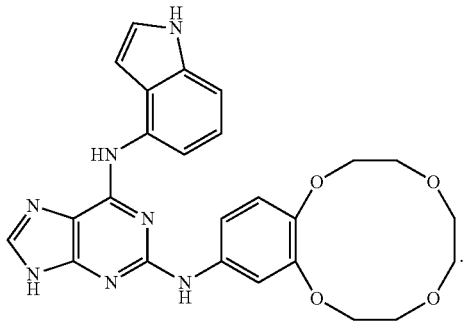

or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

24

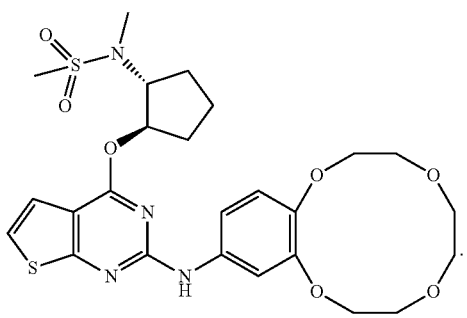

or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

Compound-26

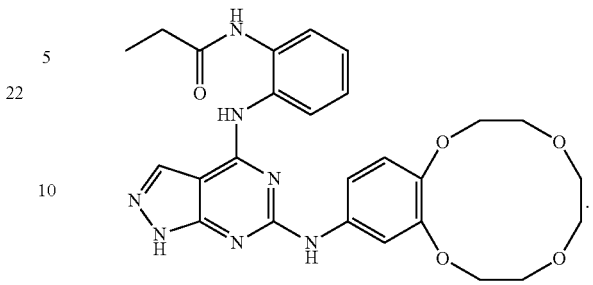

or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

Compound-27

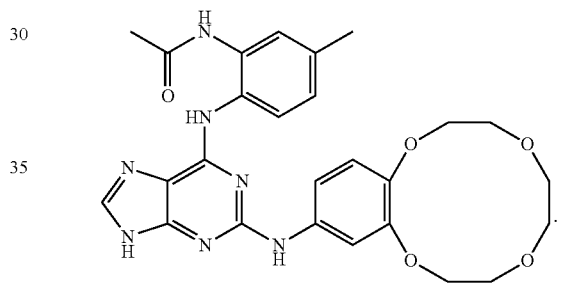

or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

Compound-28

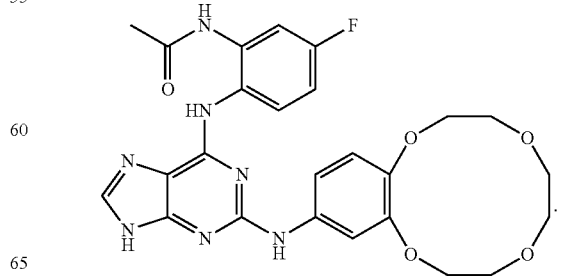

or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

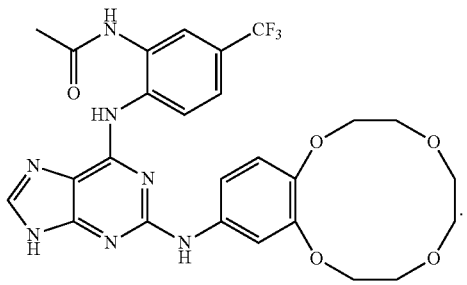

Compound-29 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

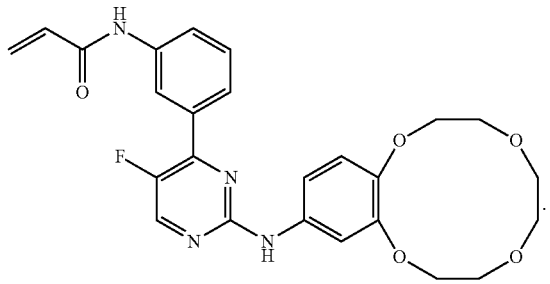

Compound-30 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

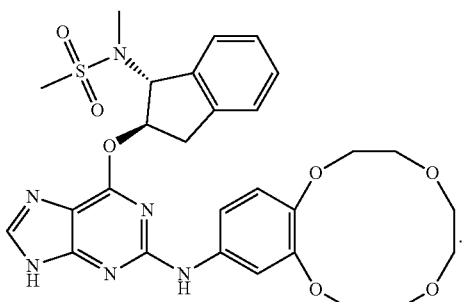

Compound-31 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to a method for treating, reducing, or preventing a disease or disorder, comprising administering to a subject in need thereof a pharmaceutical composition comprising a compound having the structural formula of:

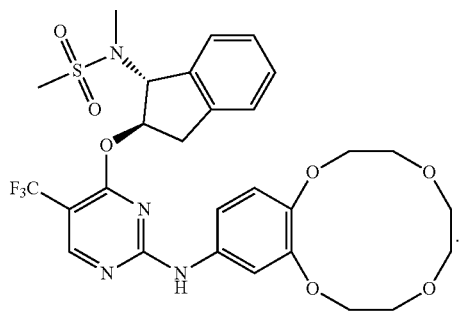

Compound-32 or a pharmaceutically acceptable form thereof, effective to treat, prevent, or reduce one or more of cancer, inflammatory disease, fibrosis, autoimmune disease, diabetes, or immunologically mediated disease, or a related disease or disorder thereof, in a mammal, including a human, and a pharmaceutically acceptable excipient, carrier, or diluent.

In yet another aspect, the invention generally relates to use of a compound disclosed herein and a pharmaceutically acceptable excipient, carrier, or diluent, in preparation of a medicament for treating a disease or disorder.

In certain embodiments of the use, the disease or disorder is cancer, or a related disease or disorder.

In certain embodiments of the use, the disease or disorder is an inflammatory disease, or a related disease or disorder.

In certain embodiments of the use, the disease or disorder is fibrosis, or a related disease or disorder.

In certain embodiments of the use, the disease or disorder is an autoimmune disease, or a related disease or disorder.

In certain embodiments of the use, the disease or disorder is an immunologically mediated disease, or a related disease or disorder.

The compounds, pharmaceutical compositions and methods of the invention can be used for the treatment of proliferative diseases that can be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell, ALL in particular.

The compounds, pharmaceutical compositions and methods of the invention can be used for the treatment of autoimmune and inflammatory diseases such as rheumatic diseases (e.g., rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), autoimmune hematologic disorders (e.g., hemolytic anemia, aplasic anemia, idiopathic thrombocytopenia, and neutropenia), autoimmune gastritis, and autoimmune inflammatory bowel diseases (e.g., ulcerative colitis and Crohn's disease), host versus graft disease, allograft rejection, chronic thyroiditis, Graves' disease, schleroderma, diabetes (type I and type II), active hepatitis (acute and chronic), pancreatitis, primary billiary cirrhosis, myasthenia gravis, multiple sclerosis, systemic lupus erythematosis, psoriasis, atopic dermatitis, contact dermatitis, eczema, skin sunburns, vasculitis (e.g., Behcet's disease), chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g., chronic obstructive pulmonary disease) and other inflammatory or obstructive disease on airways.

The compounds, pharmaceutical compositions and methods of the invention can provide enhanced anti-inflammatory effects when the subject is also can provide enhanced therapeutic effects when it is administered in combination with another therapeutic agent for treating inflammatory diseases, autoimmune diseases, or immunologically mediated diseases.

Examples of the therapeutic agent for treating the inflammatory diseases, autoimmune diseases, or immunologically mediated diseases may include, but are not limited to, steroid drugs (e.g., prednisone, prednisolone, methyl prednisolone, cortisone, hydroxycortisone, betametasone, dexametasone and the like), methotrexates, leflunomides, anti-TNFa agents (e.g., etanercept, infliximab, adalimunab and the like), calcineurin inhibitors (e.g., tacrolimus, pimecrolimus and the like) and antihistaminic drugs (e.g., diphenhydramine, hydroxyzine, loratadine, ebastine, ketotifen, cetirizine, levocetirizine, fexofenadine and the like), and at least one therapeutic agent selected therefrom may be included in the inventive pharmaceutical composition.

The compounds, pharmaceutical compositions and methods of the invention can be used for the treatment of allergies, e.g., allergies to foods, food additives, insect poisons, dust mites, pollen, animal materials and contact allergens, type I hypersensitivity allergic asthma, allergic rhinitis, allergic conjunctivitis.

The compounds, pharmaceutical compositions and methods of the invention can be used for the treatment of infectious diseases, e.g., sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

The compounds, pharmaceutical compositions and methods of the invention can be used for the treatment of bone resorption disorders, e.g., osteoporosis, osteoarthritis, traumatic arthritis, gouty arthritis and bone disorders related with multiple myeloma.

The compounds, pharmaceutical compositions and methods of the invention can be used for the treatment of cancer induced by BTK and/or FAK tyrosine kinase or a mutant thereof.

The compounds, pharmaceutical compositions and methods of the invention can be used for the treatment of cancer induced by BTK or a mutant thereof.

The compounds, pharmaceutical compositions and methods of the invention can be used for the treatment of cancer induced by BTK and/or BMX tyrosine kinase or a mutant thereof.

The compounds, pharmaceutical compositions and methods of the invention can be used for the treatment of cancer induced by BMX tyrosine kinase.

The compounds, pharmaceutical compositions and methods of the invention can be used for the treatment of cancer induced by ERK kinase.

Examples of the cancers or tumors may include, but are not limited to, liver cancer, hepatocellular carcinoma, thyroid cancer, colorectal cancer, testicular cancer, bone cancer, oral cancer, basal cell carcinoma, ovarian cancer, brain tumor, gallbladder carcinoma, biliary tract cancer, head and neck cancer, colorectal cancer, vesical carcinoma, tongue cancer, esophageal cancer, glioma, glioblastoma, renal cancer, malignant melanoma, gastric cancer, breast cancer, sarcoma, pharynx carcinoma, uterine cancer, cervical cancer, prostate cancer, rectal cancer, pancreatic cancer, lung cancer, skin cancer, and other solid cancer.

The compounds, pharmaceutical compositions and methods of the invention can provide enhanced anticancer effects when the subject is also administered another anticancer agent(s).

Examples of the anticancer agents may include, but are not limited to, immunotherapies (e.g. CTLA4 antagonist, cell signal transduction inhibitors (e.g., imatinib, gefitinib, bortezomib, erlotinib, sorafenib, sunitinib, dasatinib, vorinostat, lapatinib, temsirolimus, nilotinib, everolimus, pazopanib, trastuzumab, bevacizumab, cetuximab, ranibizumab, pegaptanib, panitumumab and the like), mitosis inhibitors (e.g., paclitaxel, vincristine, vinblastine and the like), alkylating agents (e.g., cisplatin, cyclophosphamide, chromabucil, carmustine and the like), anti-metabolites (e.g., methotrexate, 5-FU and the like), intercalating anticancer agents, (e.g., actinomycin, anthracycline, bleomycin, mitomycin-C and the like), topoisomerase inhibitors (e.g., irinotecan, topotecan, teniposide and the like), immunotherapic agents (e.g., interleukin, interferon and the like) and antihormonal agents (e.g., tamoxifen, raloxifene and the like), and at least one anticancer agent selected therefrom may be included in the inventive pharmaceutical composition.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^{3}H$) and carbon-14 ($^{14}C$) labeled compounds are particularly preferred for their ease of preparation and detectability. Further, substitution with heavier isotopes such as deuterium ($^{2}H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen (1H) with heavier isotopes such as deuterium can afford certain therapeutic advantages, e.g., resulting from improved absorption, distribution, metabolism and/or excretion (ADIE) properties, creating drugs with improved efficacy, safety, and/or tolerability. Benefits may also be obtained from replacement of normally abundant $^{12}C$ with $^{13}C$. (See, WO 2007/005643, WO 2007/005644, WO 2007/016361, and WO 2007/016431.)

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure. Solvates and polymorphs of the compounds of the invention are also contemplated herein. Solvates of the compounds of the present invention include, for example, hydrates.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

The following examples are meant to be illustrative of the practice of the invention, and not limiting in any way.

EXAMPLES

Compound Synthesis

4-[3-[(5-ethyl-2,2-dimethyl-1,3-dioxan-5-yl)oxy]propoxy]aniline (I-1)

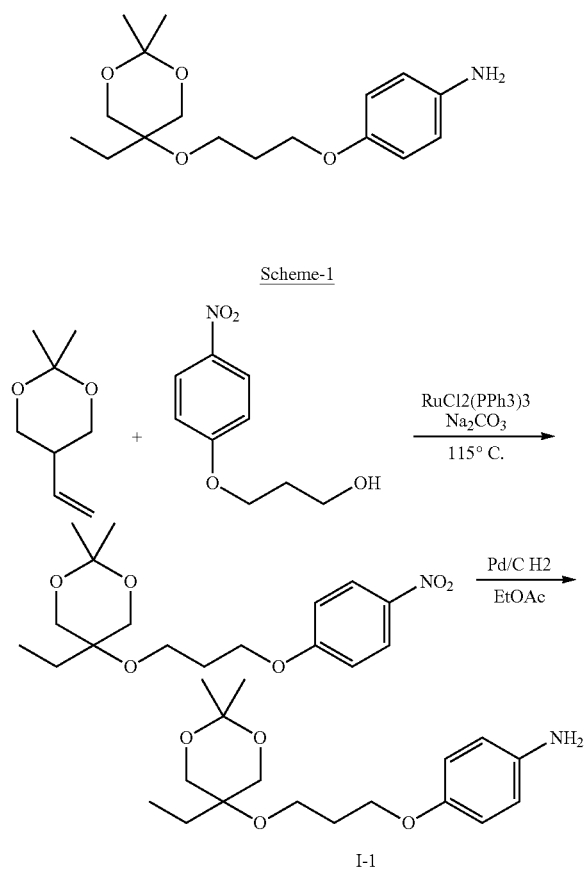

In a round-bottom flask, 2,2-dimethyl-5-vinyl-1,3-dioxane (2.9 g, 20.4 mmol, 2.0 eq.), 3-(4-nitrophenoxy)propan-1-ol (2.0 g, 10.2 mmol, 1.0 eq.), sodium carbonate (206 mg, 2.0 mmol, 0.2 eq.), $RuCl_2(PPh_3)_3$ (192 mg, 0.2 mmol, 2.0% mol) were heated at 115° C. under nitrogen for 3 hr. TLC showed complete reaction (PE/EA=15:1), giving crude 5-ethyl-2,2-dimethyl-5-[3-(4-nitrophenoxy)propoxy]-1,3-dioxane (2.78 g, 80% yield).

To the intermediate obtained above (2.78 g, 8.2 mmol) in 60 mL of ethyl acetate, Palladium on carbon (200 mg, 7% Wt) was added. The reaction flask was vacuumed/refilled with hydrogen several times. The mixture was stirred at r.t. for 16 hr. under hydrogen. After filtration and concentration, the residue was purified by column chromatography on silica gel with petroleum ether/ethyl acetate (v/v ratio=5:1→3:1), giving the desired 4-[3-[(5-ethyl-2,2-dimethyl-1,3-dioxan-5-yl)oxy]-propoxy]aniline (I-1) (2.4 g, 95% yield).

LC-MS: 168.1 [ESI, M+1 for 3-(4-aminophenoxy)propan-1-ol)]

6,7,9,10,12,13-Hexahydro-5,8,11,14-tetraoxa-benzocyclododecen-2-ylamine (I-2)

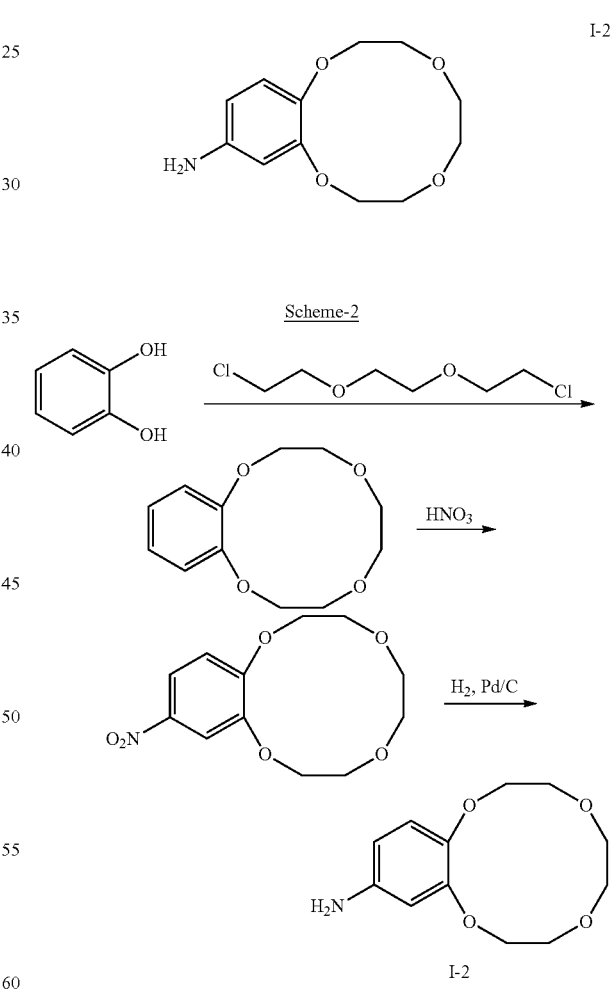

Step-1. Under nitrogen, to the mixture of (22.02 g, 199.98 mmol) in 220 mL of n-butanol, was added 46 mL of aqueous solution of LiOH H₂O (18.46 g, 439.94 mmol). The mixture was heated to 95° C., followed by addition of 1-chloro-2-[2-(2-chloro-ethoxy)-ethoxy]-ethane (37.43 g, 200.09 mmol) in 240 mL of n-butanol. The reaction was heated overnight, then filtrated. 1 M of aqueous hydrochloric acid was added to adjust pH to 8. After removal of most n-butanol under reduced pressure, the residue was extracted with dichloromethane 250 mL×2. The combined organic layer was washed with brine and dried over anhydrous MgSO$_4$. The crude product was purified by column chromatography on silica gel, giving 6.5 g of 6,7,9,10,12,13-Hexahydro-5,8,11,14-tetraoxa-benzocyclododecene as yellow oil, 14.4% yield.

Step-2. To a refluxing solution of 6,7,9,10,12,13-Hexahydro-5,8,11,14-tetraoxa-benzo-cyclododecene (6.50 g, 28.98 mmol) in 65 mL of acetonitrile, was added nitric acid (56%, 5.4 mL) dropwise. When TLC showed the completion of reaction, 160 mL of water was added. The resulting solution was kept at 2° C. overnight. The precipitate was collected and washed until to neutral pH, giving desired 2-Nitro-6,7,9,10,12,13-hexahydro-5,8,11,14-tetraoxa-benzocyclododecene as yellow solid (4.61 g, 59% yield).

Step-3. To the nitro compound (4.61 g, 17.12 mmol) suspended in 90 mL of MeOH was added 0.46 g of 10% Pd/C. After hydrogen exchange, the mixture was stirred under H$_2$ overnight. TLC showed complete reduction of nitro material. Hydrogen was removed and the reaction flask was refilled with nitrogen several times. The reaction mixture was filtered, concentrated, and purified by column chromatography on silica gel, giving 3.76 g of the desired aniline (I-2), (91.7% yield).

LC/MS: 240.2 (ES+, M+1)

$^1$HNMR (CDCl$_3$, 400 MHz) δ 6.83 (d, 1H, J=8 Hz), 6.33 (dd, 1H, J=4 Hz), 6.26 (dd, 1H, J=4, 8 Hz), (4.11, m 4H), 3.89 (m, 2H), 3.80 (m, 6H), 1.75 (br s, 2H).

1-[(3R)-3-[[2-[4-[3-[(2-ethyl-5,5-dimethyl-1,3-dioxan-2-yl)oxy]propoxy]anilino]-5-fluoro-pyrimidin-4-yl]amino]-1-piperidyl]prop-2-en-1-one (Compound-1)

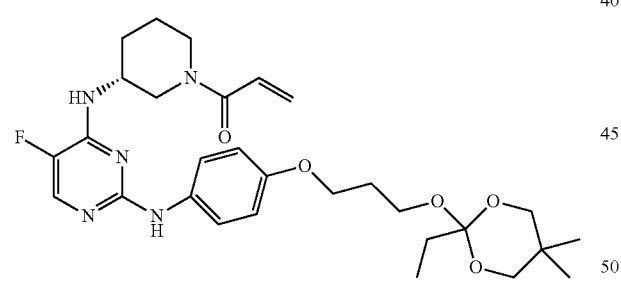

Compound-1

Scheme-3

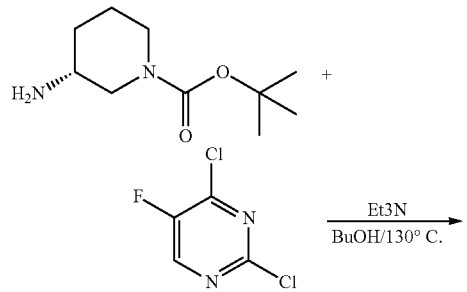

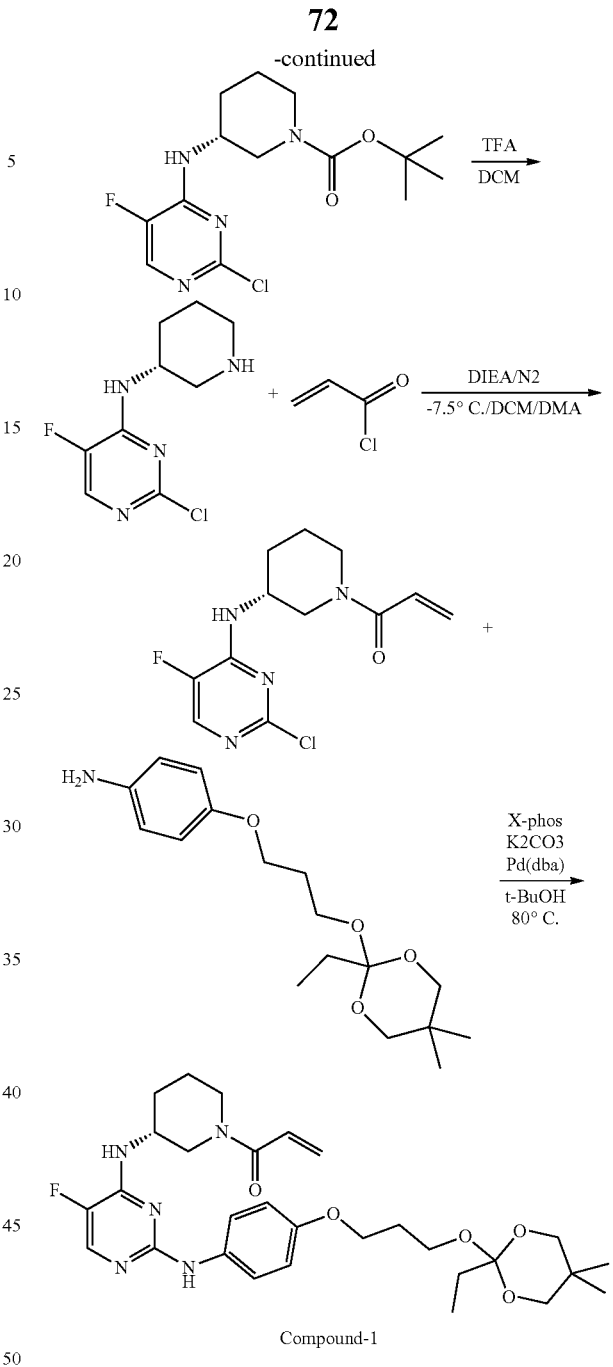

Step-1 (Cl-displacement). tert-butyl (3R)-3-aminopiperidine-1-carboxylate (3.8 g, 19.2 mmol), 2,4-dichloro-5-F-pyrimidine (3.2 g, 19.2 mmol) and trimethylamine (4.56 mL, 32 mmol) were mixed in 25 mL of n-butanol. The reaction mixture was heat at 130° C. overnight. LC-MS showed completion of the reaction. After concentration, the residue was subject to regular aqueous work up, and extracted by ethyl acetate. The organic layer was washed with water, brine, and dried over anhydrous MgSO$_4$. After filtration and concentration, the crude product was purified by column chromatography on silica gel (petroleum ether/ethyl acetate v/v 4/1), giving tert-butyl (3R)-3-[(2-chloro-5-fluoro-pyrimidin-4-yl)amino]piperidine-1-carboxylate (4.8 g, 73%) as a white solid.

Step-2 (De-Boc). DeBoc reaction was done using Boc-Intermediate above (3.3 g, 10 mmol) with 6 mL of trifluoroacetic acid in 15 mL of dichloromethane for 4 hr. The solvent was removed under reduced pressure, the residue was suspended between ethyl acetate (200 mL) and saturated sodium bicarbonate. The organic layer was separated and dried with anhydrous MgSO₄. After filtration and concentration, de-Boc product was obtained (1.4 g, 61% yield).

Step-3 (Acryloylation). To a mixture of de-Boc intermediate (0.8 g, 3.5 mmol) and DIPEA (0.91 g, 7 mmol) in 20 mL of DCM/DMA (v/v 3:1) at −7.5° C., was added acryloyl chloride (0.4 mL, 5.0 mmol) in 5 mL of DCM. The reaction mixture was stirred overnight. After concentration and regular aqueous workup with ethyl acetate, the final product was purified by column chromatography on silica gel, with petroleum ether/ethyl acetate=3/1, giving acrylalmide 0.62 g, 62% yield.

Step-4 (Pd-mediated Aryl amination). To a mixture of acrylamide (0.31 g, 1.09 mmol), and key intermediate I-1 (0.4 g, 1.3 mmol) in 6 mL of t-butanol, was added potassium carbanate (1.4 g, 9.2 mmol), X-phos (0.22 g, 0.24 mmol), and Pd₂(dba)₃ (0.06 g, 0.12 mmol). After nitrogen exchange, the mixture was heated at 80° C. overnight. The product was extracted with ethyl acetate, and was purified by column chromatography on silica gel, with petroleum ether/ethyl acetate=3/1 to 2/1, desired final product 1-[(3R)-3-[[2-[4-[3-[(2-ethyl-5,5-dimethyl-1,3-dioxan-2-yl)oxy]propoxy]anilino]-5-fluoro-pyrimidin-4-yl]amino]-1-piperidyl]prop-2-en-1-one (0.15 g, 25%).

LC-MS: m/z (ES+, M-142 2,5,5-trimethyl-1,3-dioxane)

Synthesis of 1-[(3R)-3-[[5-fluoro-2-(2,5,8,11-tetraoxabicyclo[10.4.0]hexadeca-1(12),13,15-trien-14-ylamino)pyrimidin-4-yl]amino]-1-piperidyl]prop-2-en-1-one (Compound-2)

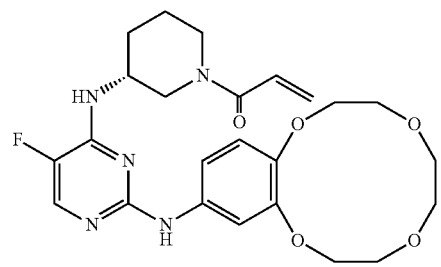

Compound-2

Scheme 4

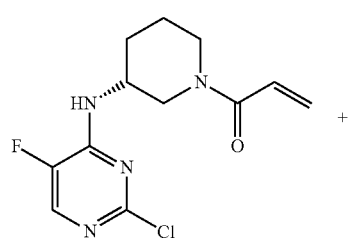

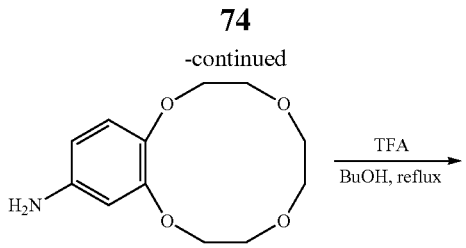

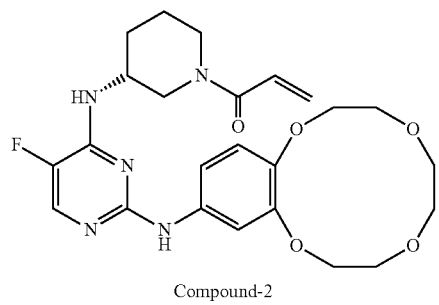

Compound-2

To the mixture of acrylamide (61 mg, 0.21 mmol, 1.07 eq.) and key intermediate I-2 (48 mg, 0.2 mmol, 1 eq.) in 4 mL of n-buthanol, was added 2 drops of trifluoroacetic acid. The resulting mixture was refluxed overnight. The reaction mixture was concentrated, and the residue was neutralized with sodium bicarbonate, extracted with ethyl acetate. The crude product was purified by column chromatography on silica gel, with DCM/MeOH v/v=30/1, giving white solid 46 mg (26%) as desired 1-[3-[[5-fluoro-2-(2,5,8,11-tetraoxabicyclo[10.4.0]hexadeca-1(12), 13,15-trien-14-ylamino)pyrimidin-4-yl]amino]-1-piperidyl]prop-2-en-1-one.

LC-MS: m/z 488.2 (ES+, M+1).

1-[(3R)-3-[[2-(2,5,8,11-tetraoxabicyclo[10.4.0]hexadeca-1(12),13,15-trien-14-ylamino)-9H-purin-6-yl]amino]-1-piperidyl]prop-2-en-1-one (Compound-3)

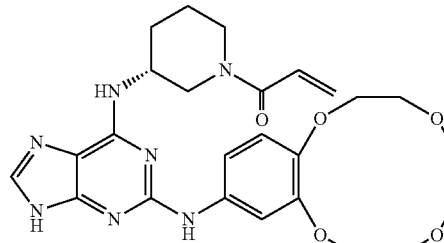

Compound-3

Scheme 5
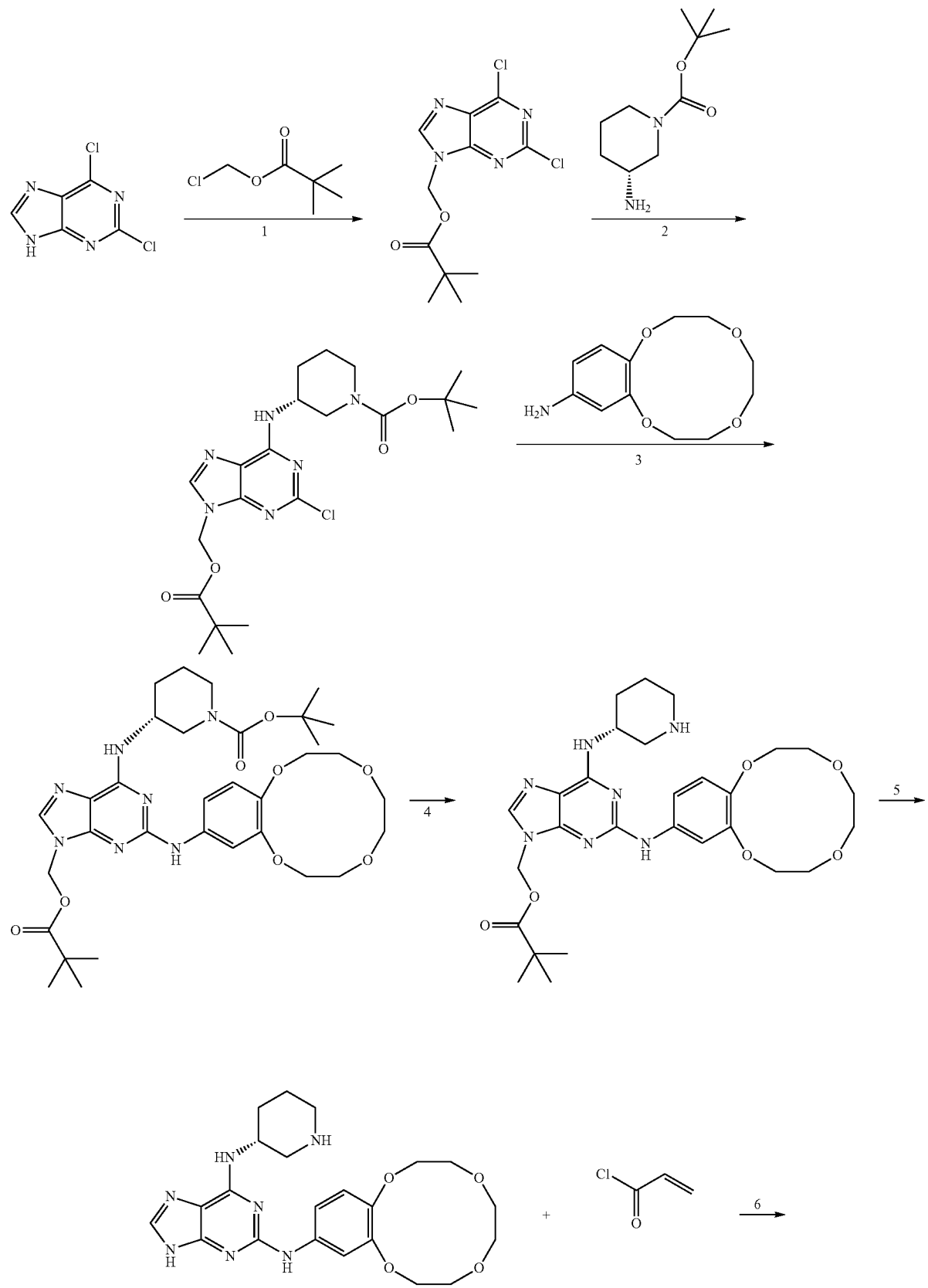

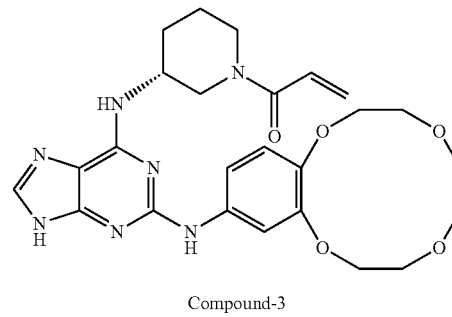

Compound-3

Step-1 (N-protection). To the mixture of 2,6-dichloro-9H-purine (11 g, 60 mmol), and cesium carbonate (29 g, 90 mmol) in 20 mL of DMSO, was added dropwise chloromethyl 2,2-dimethylpropanoate (13.5 g, 90 mmol). After stirring at r.t. for 48 hr., the mixture was poured into the ice. The product was extracted with ethyl acetate, and purified by column chromatography on silica gel with petroleum ether/ethyl acetate 7/1 to 5/1, giving 5 g of (2,6-dichloropurin-9-yl)methyl 2,2-dimethylpropanoate (270%).

Step-2 (Cl-displacement). This step was carried out in the same way as described in the Step-1 of Scheme 3 using (2,6-dichloropurin-9-yl)methyl 2,2-dimethylpropanoate (2.1 g, 6.93 mmol) and 2,4-dichloro-5-F-pyrimidine (1.66 g, 8.32 mmol), giving tert-butyl (3R)-3-[[2-chloro-9-(2,2-dimethylpropanoyloxymethyl)purin-6-yl]amino] piperidine-1-carboxylate as white foamy solid (2.3 g, 71%).

Step-3 (Pd-mediated Aryl amination). This step was carried out in the same way as described in the Step-4 of Scheme 3 using the product from last step (1.4 g, 3.0 mmol) with 2,5,8,11-tetraoxabicyclo[10.4.0]hexadeca-1(12),13,15-trien-14-amine (0.86 g, 3.6 mmol, X-phos (0.15 g, 0.3 mmol), $Pd_2$ (dba)$_3$ (0.2 g, 0.2 mmol), giving tert-butyl (3R)-3-[[9-(2,2-dimethylpropanoyloxymethyl)-2-(2,5,8,11-tetraoxabicyclo[10.4.0]hexadeca-1(12),13,15-trien-14-ylamino)purin-6-yl]amino]piperidine-1-carboxylate (0.6 g, 30%).

Step-4 (deprotection). To diaminopurine from last step (0.6 g, 0.9 mol) in 10 mL of THF and 5 mL of MeOH mixture at 0° C., was added 0.96 mL of 3 M aqueous NaOH. The mixture was stirred at r.t. for 5 hr., followed by 0.4 mL of ammonium hydroxide (25~28%). The stirring was continued overnight, and the product was extracted with ethyl acetate. After concentration, a crude product (0.35 g) was obtained and used directly in the following step.

Step-5 (de-Boc). Boc deprotection was done using the crude product obtained above with 2 mL of TFA in 4 mL of DCM. The reaction mixture was poured into water, sonicated and filtered, giving 0.4 g solid.

Step-6 (acryloylation). The acryloylation was carried out using deprotected intermediate (0.15 g, 0.33 mol) in 12 mL of THF/water/DMF10/1/1 mixed solvent with acryloyl chloride (32 µL, 1.1 eq.) and trimethylamine (0.1 g, 1 mmol). After stirring overnight, the mixture was poured into water. The solid was collected, giving 29 mg of yellow solid, purity 96.7% (17% yield).

LC-MS: 510.2 (ES+, M+1).

1-[(3R)-3-[[2-(2,5,8,11-tetraoxabicyclo[10.4.0]hexadeca-1(12),13,15-trien-14-ylamino)-9H-purin-6-yl]amino]-1-piperidyl]propan-1-one (Compound-4)

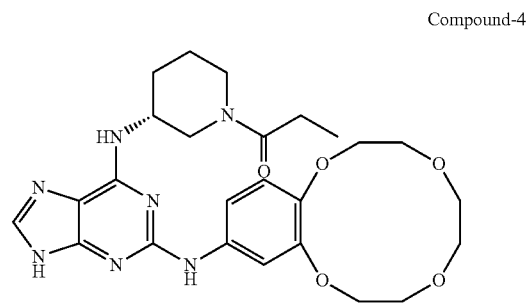 [SMILES: CCC(=O)N1CCC[C@@H](Nc2nc(Nc3ccc4c(c3)OCCOCCOCCO4)nc3[nH]cnc23)C1]

Compound-4

Compound-4 was made by hydrogenation of Compound-3 over Pd/C in Methanol.

LC-MS: 512.2 (ES+, M+1).

N-[3-[[2-[4-[3-[(2-ethyl-5,5-dimethyl-1,3-dioxan-2-yl)oxy]propoxy]anilino]-5-fluoro-pyrimidin-4-yl]amino]phenyl]prop-2-enamide (Compound-5)

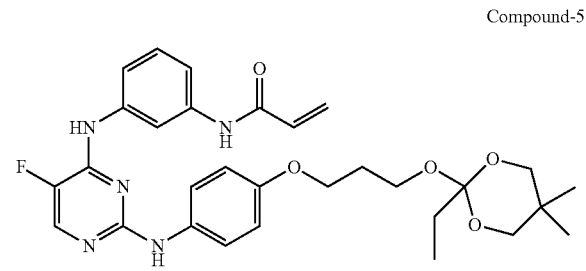 [SMILES: C=CC(=O)Nc1cccc(Nc2nc(Nc3ccc(OCCCOC4(CC)OCC(C)(C)CO4)cc3)ncc2F)c1]

Compound-5

The synthesis of Compound-5 was carried out in the same ways as for Compound-1 using meta-N-Boc aniline as starting material in place of 3-amino-N-Boc-piperidine.

LC-MS: m/z=425.1 (ES+, M+H-142).

N-[3-[[5-fluoro-2-(2,5,8,11-tetraoxabicyclo[10.4.0]hexadeca-1(12),13,15-trien-]4-ylamino)pyrimidin-4-yl]amino]phenyl]prop-2-enamide (Compound-6)

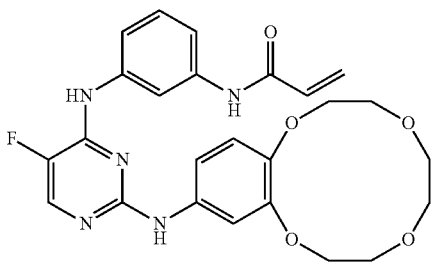

Compound-6

The synthesis of Compound-6 was carried out in the same ways as for Compound-2 using meta-N-Boc aniline as starting material in place of 3-amino-N-Boc-piperidine.

LC-MS: m/z=496.3 (ES+, M+H).

¹HNMR (DMSO-d₆, 400 MHz) δ 10.15 (s, 1H), 9.41 (s, 1H), 9.04 (s, 1H), 8.08 (s, 1H), 7.93 (s, 1H), 7.48 (m, 2H), 7.37 (d, 1H, J=4 Hz), 7.27 (dd, 1H, J=4, 8 Hz), 7.21 (dd, 1H, J=4, 8 Hz), 6.83 (d, 1H, J=8 Hz), 6.47 (dd, 1H, J=8, 16 Hz), 6.24 (dd, 1H, J=4, 16 Hz), 5.74 (dd, 1H, J=4, 8 Hz), 4.00 (br s, 2H), 3.88 (br s, 2H), 3.67 (br s, 4H), 3.43 (br s, 4H).

N-[3-[[2-(2,5,8,11-tetraoxabicyclo[10.4.0]hexadeca-1(12),13,15-trien-14-ylamino)-9H-purin-6-yl]amino]phenyl]prop-2-enamide (Compound-7)

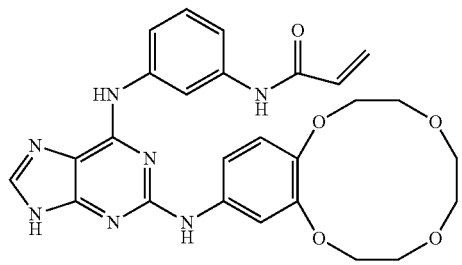

Compound-7

The synthesis of Compound-7 was carried out in the same ways as for Compound-3 using meta-N-Boc aniline as starting material in place of 3-amino-N-Boc-piperidine.

LC-MS: m/z=518.3 (ES+, M+H).

¹HNMR (DMSO-d₆, 400 MHz) δ 10.27 (s, 1H), 9.07 (s, 1H), 8.10 (s, 1H), 7.72 (d, 1H, J=8 Hz), 7.51~7.46 (m, 3H), 6.92 (d, 1H, J=12 Hz), 6.50 (dd, 1H, J=12, 20 Hz), 6.27 (d, 1H, J=20 Hz), 5.27 (d, 1H, J=12 Hz), 4.00 (m, 4H), 3.68 (m, 8H).

N-[3-[[2-(2,5,8,11-tetraoxabicyclo[10.4.0]hexadeca-1(12),13,15-trien-14-ylamino)-9H-purin-6-yl]amino]phenyl]propanamide (Compound-8)

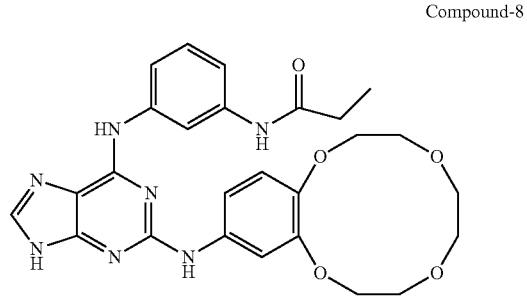 [SMILES: CCC(=O)Nc1cccc(Nc2nc(Nc3ccc4c(c3)OCCOCCOCCO4)nc3[nH]cnc23)c1]

Compound-8

Compound-8 was made by hydrogenation of Compound-7 over Pd/C in Methanol.

LC-MS: m/z=520.3 (ES+, M+H).

N-[2-[[2-[4-[3-[(2-ethyl-5,5-dimethyl-1,3-dioxan-2-yl)oxy]propoxy]anilino]-5-fluoro-pyrimidin-4-yl]amino]phenyl]prop-2-enamide (Compound-9)

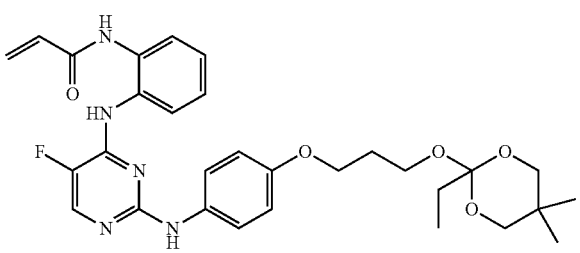

Compound-9

Compound-9 was made in the same way as described for making Compound-1 in Scheme-3, starting from tert-butyl N-(2-aminophenyl)carbamate instead of tert-butyl (3R)-3-aminopiperidine-1-carboxylate.

LC-MS: m/z=425.3 (ES+, M+H-142 fragmentation).

¹HNMR (CDCl₃, 400 MHz) δ 7.93 (d, 1H, J=3 Hz), 7.63 (br s, 1H), 7.53 (br s, 1H), 7.47 (br s, 1H), 7.29 (d, 2H, J=8 Hz), 6.75 (d, 2H, J=8 Hz), 6.40 (d, 1H, J=20 Hz), 6.15 (dd, 1H, J=12, 20 Hz), 5.73 (d, 1H, J=12 Hz), 4.05 (t, 2H, J=4 hz), 3.79 (d, 2H, J=12 Hz), 3.60 (t, 2H, J=8 Hz), 2.10 (m, 2H), 1.75 (q, 2H, J=8 Hz), 1.13 (s, 3H), 0.97 (t, 3H, J=8 Hz), 0.51 (s, 3H).

N-[2-[[5-fluoro-2-(2,5,8,11-tetraoxabicyclo[10.4.0]hexadeca-1(12),13,15-trien-14-ylamino)pyrimidin-4-yl]amino]phenyl]prop-2-enamide (Compound-10)

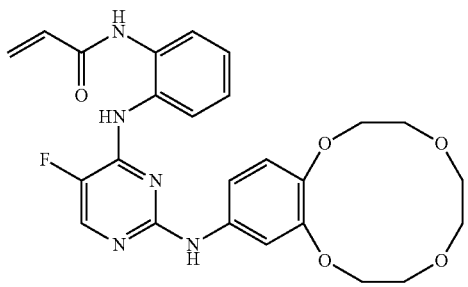

Compound-10

Compound-10 was made in the same way as described for making Compound-2 in Scheme-4, starting from tert-butyl N-(2-aminophenyl)carbamate instead of tert-butyl (3R)-3-aminopiperidine-1-carboxylate.

LC-MS: m/z=496.2 (ES+, M+H).

$^1$HNMR (CD$_3$OD, 400 MHz) δ 7.96 (s, 1H), 7.71 (d, 1H, J=8 Hz), 7.56 (br d, 1H, J=8 Hz), 7.34 (s, 1H), 7.29 (br t, 2H, J=8 Hz), 6.92 (d, 1H, J=12 Hz), 6.86 (d, 1H, J=8 Hz), 6.33~6.39 (m, 2H), 5.77 (d, 1H, J=12 Hz), 4.10 (br t, 2H, J=4 Hz), 3.87 (br t, 2H, J=4 Hz), 3.78 (s, 4H), 3.75 (s, 4H).

N-[2-[[2-(2,5,8,11-tetraoxabicyclo[10.4.0]hexadeca-1(12),13,15-trien-14-ylamino)-9H-purin-6-yl]amino]phenyl]prop-2-enamide (Compound-11)

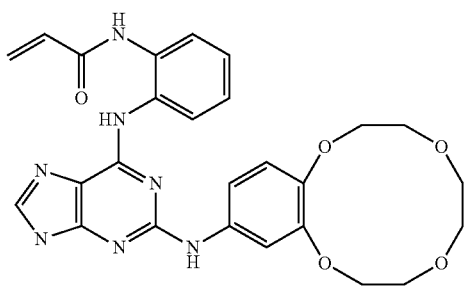

Compound-11

Compound-11 was made in the same way as described for making Compound-3 in Scheme-5, starting from tert-butyl N-(2-aminophenyl)carbamate instead of tert-butyl (3R)-3-aminopiperidine-1-carboxylate.

LC-MS: m/z=518.2 (ES+, M+H).

$^1$HNMR (DMSO-d$_6$, 400 MHz) δ 12.6 (s, 1H), 10.11 (s, 1H), 8.81 (s, 1H), 8.76 (s, 1H), 7.92 (d, 1H, J=8 Hz), 7.50 (d, 1H, J=8 Hz), 7.25 (m, 2H), 6.86 (d, 1H, J=12 Hz), 6.56 (s, 1H), 6.41 (dd, 1H, J=12, 20 Hz), 6.25 (d, 1H, J=20 Hz), 5.80 (dd, 1H, J=4, 12 Hz), 4.00 (br s, 2H), 3.89 (br s, 2H), 3.68 (m, 8H).

N-[2-[[2-(2,5,8,11-tetraoxabicyclo[10.4.0]hexadeca-1(12),13,15-trien-14-ylamino)-9H-purin-6-yl]amino]phenyl]propanamide (Compound-12)

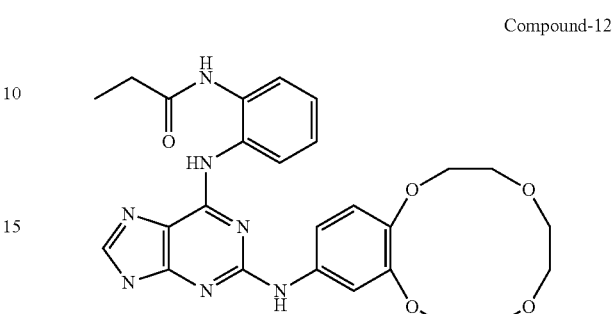

Compound-12

Compound-12 was made by hydrogenation of Compound-11 over 10% Pd/C in MeOH. Compound-12 can also be made in the same way as described for making Compound-11 by carrying out propanation instead of acryloylation.

LC-MS: m/z=520.2 (ES+, M+H).

2-amino-N-methoxy-benzamide (I-3)

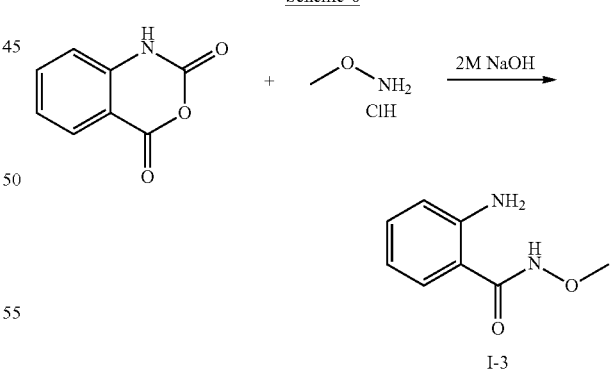

Scheme-6

At 0 C, 10 mL of 2 M NaOH aqueous solution was added into 25% O-methylhydroxylamine (1640 mg, 19.6 mmol, 3.2 eq.) aqueous solution. After stirring for 30 min, 1H-3,1-benzoxazine-2,4-dione (994 mg, 6.1 mmol, 1 eq.) was added in several portions. The reaction was then stirred at r.t. for 3 hr. The desired product was extracted by ethyl acetate, and titurated with ethyl ether, giving browny solid (600 mg, 60%).

4,6-dichloro-1-tetrahydropyran-2-yl-pyrazolo[3,4-d]pyrimidine (I-4)

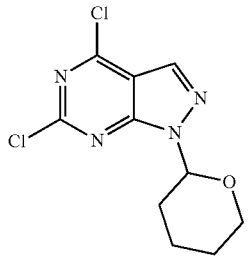

Scheme-7

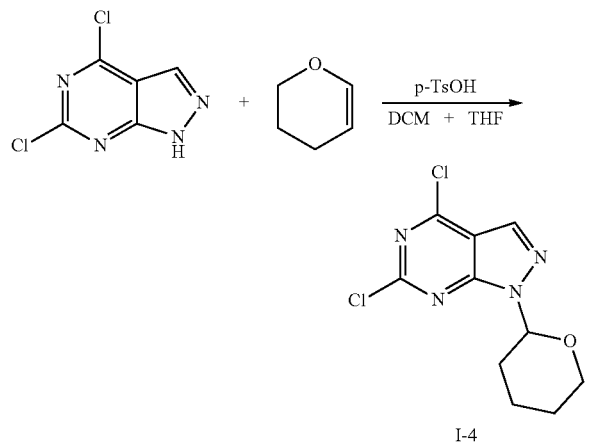

To a mixture of 4,6-dichloro-1H-pyrazolo[3,4-d]pyrimidine (200 mg, 1.06 mmol, 1.0 eq) and p-tosyl acid (20.1 mg, 0.106 mmol, 0.1 eq) in 3 mL of THF and 3 mL of DCM, was added 3,4-dihydro-2H-pyran (134 mg, 1.6 mmol, 1.5 eq). The mixture was stirred at r.t. for 1 hr., until TLC showed the complete reaction. The reaction mixture was concentrated, then re-dissolved in 10 mL of DCM, washed with saturated NaHCO$_3$, water, and brine. The organic layer was dried and concentrated, giving desire intermediate I-4 as white solid (287 mg, 100%).

N-[3-(aminomethyl)-2-pyridyl]-N-methyl-methanesulfonamide (I-5)

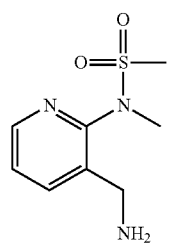

Scheme-8

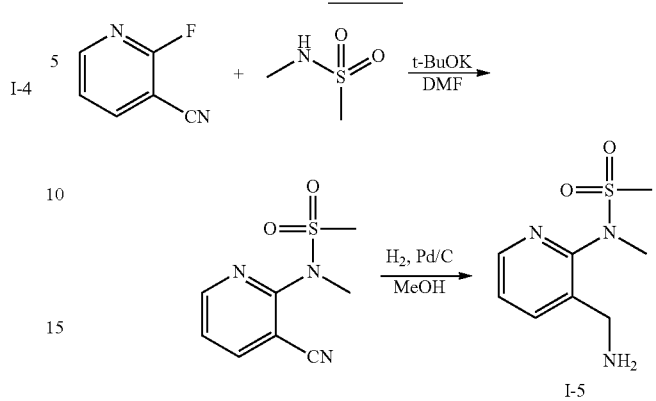

To N-methylmethanesulfonamide (2.18 g, 20 mmol, 1.0 eq) in 20 mL of DMF, was added t-BuOK (2.24 g, 20 mmol, 1.0 eq.). After stirring at r.t. for 30 min., 2-fluoro-3-cyanopyridine (2.44 g, 20 mmol, 1.0 eq) was added in one portion, and the resulting mixture was heated to 80° C. for 2 hr. (TLC showed the complete reaction). The reaction mixture was poured on ice and extracted with ethyl acetate. The dried organic layer was concentrated, and purified by column chromatography on silica gel with petroleum ether/ethyl acetate (v/v 1/1) as eluent, giving N-(3-cyano-2-pyridyl)-N-methyl-methanesulfonamide (4.0 g, 93%).

4.0 g of nitrile was hydrogenated in methanol over 10% Pd/C overnight. TLC showed two products with m/z=216 and 413. The products were purified by column chromatography on silica gel using DCM/MeOH=10/1 as eluent, giving desired I-5 (3.0 g, 73%).

N-[(1R,2R)-2-hydroxycyclohexyl]-N-methyl-methanesulfonamide (I-6)

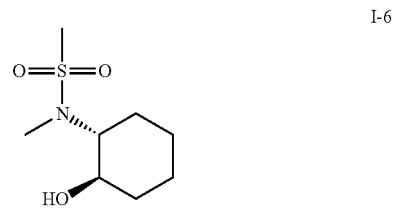

Scheme-9

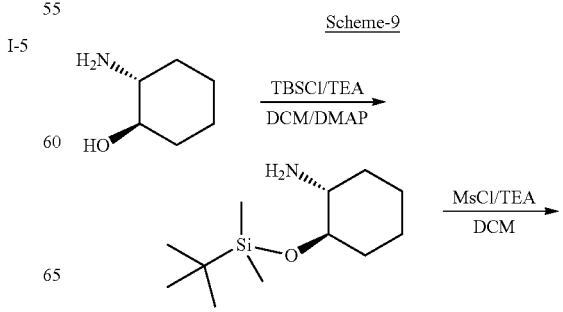

-continued

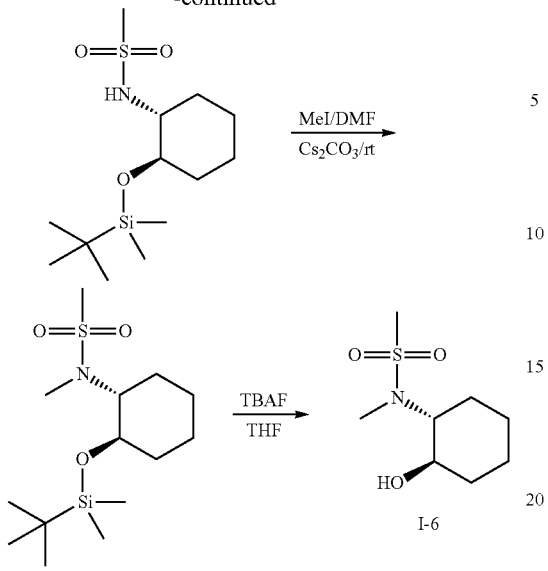

I-6

To the mixture of (1R,2R)-2-aminocyclohexanol (3.02 g, 20 mmol), TEA (8.5 ml, 60 mmol) and DMAP (0.75 g, 6.0 mmol), in 30 mL of DCM, was added TBSCl (4.5 g, 30 mmol). The reaction mixture was stirred overnight. After washing with water, the organic layer was dried over $MgSO_4$. After filtration and concentration, the residue was used directly in the following step.

With ice-bath, to the TBS-ether obtained above, was added triethylamine (4.6 mL, 34.2 mmol) in 20 mL of DCM, followed by MsCl (1.0 ml, 13.7 mmol). The reaction mixture was stirred at r.t. overnight. After regular aqueous workup, the concentrated crude product was purified by column chromatography on silica gel with p giving etroleum ether/ ethyl acetate (v/v 8/1)N-[(1R,2R)-2-[tert-butyl(dimethyl)silyl]oxycyclohexyl]methanesulfonamide (3.0 g, 2-step overall 49% yield).

To the mixture of sulfonamide obtained above (1.5 g, 4.9 mmol) and cesium carbonate (3.19 g, 9.8 mmol) in 10 mL of DMF, was added iodomethane (0.37 mL, 5.88 mmol). The reaction mixture was stirred at r.t. overnight. The reaction mixture was poured into water, and the product was extracted with ethyl acetate. After drying and concentration, the product was purified by column chromatography on silica gel (DCM/MeOH 50/1→30/1) giving N-Me-sulfonamide 1.56 g (97%).

Final deprotection of TBS group was done by reacting the N-M-sulfonamide with TBAF (1.5 equiv), giving desired alcohol I-6 (660 mg, 66%).

N-[(1R,2R)-2-hydroxycyclopentyl]-N-methyl-methanesulfonamide (I-7)

I-7

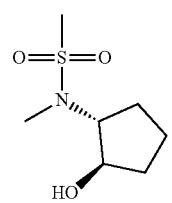

Intermediate I-7 was prepared in the same way as for I-6 shown in Scheme 8, except by using (1R,2R)-2-aminocyclopentanol hydrochloride as starting material instead of (1R,2R)-2-aminocyclohexanol.

N-[2-[[2-(2,5,8,11-tetraoxabicyclo[10.4.0]hexadeca-1(12),13,15-trien-14-ylamino)-7H-pyrrolo[2,3-d]pyrimidin-4-yl]amino]phenyl]propanamide (Compound-13)

Compound-13

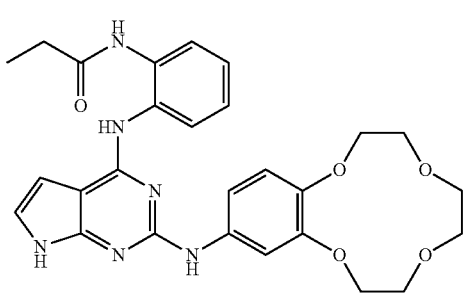

Scheme-1

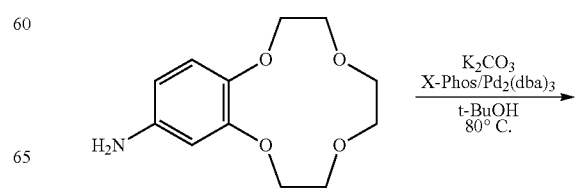

87
-continued

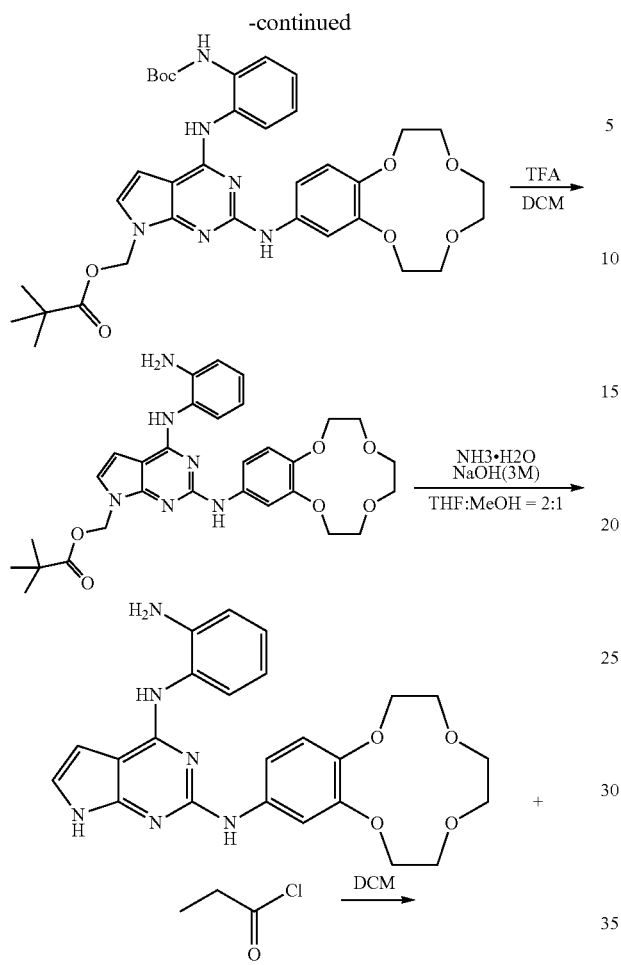

88

N-[2-[[6-(2,5,8,11-tetraoxabicyclo[10.4.0]hexadeca-1(12),13,15-trien-14-ylamino)-1H-pyrazolo[3,4-d]pyrimidin-4-yl]amino]phenyl]propanamide (Compound-14)

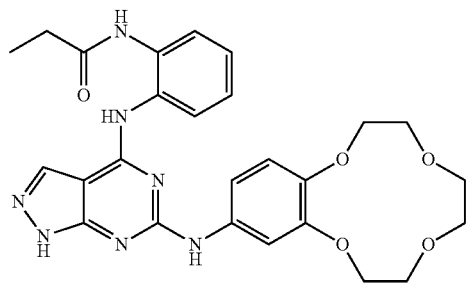

Compound-14

Scheme-11

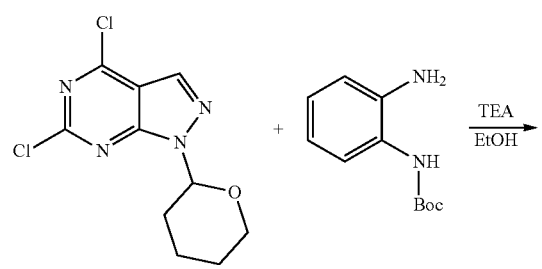

Compound-13

The synthetic schedule for Compound-13 is shown in Scheme 10, which is similar to the synthesis of Compound-3 in Scheme 5 except by using 2,4-dichloropyrrolo[2,3-d]pyrimidin-7-yl)methyl 2,2-dimethylpropanoate as starting material instead of 2,6-dichloro-9H-purine and the final step is propanoylation, rather than acryloylation.

LC-MS: m/z=518.9 (ES+, M+H).

$^1$HNMR (DMSO-d$_6$, 400 MHz) δ 10.17 (s, 1H), 9.74 (s, 1H), 8.64 (s, 1H), 7.72 (s, 1H), 7.56 (s, 2H), 7.18 (m, t, J=9~12 Hz), 6.30 (s, 1H), 4.01 (br s, 2H), 3.92 (br s, 2H), 3.68 (m, 8H), 2.30 (q, 2H, J=6 Hz), 1.03 (t, 3H, J=6 Hz).

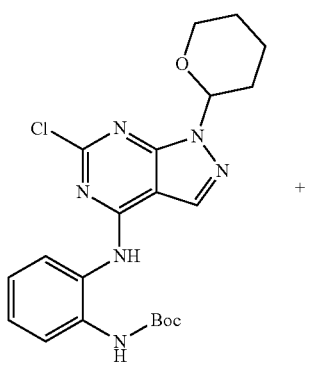

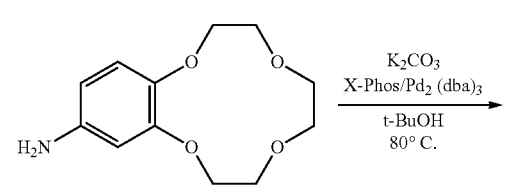

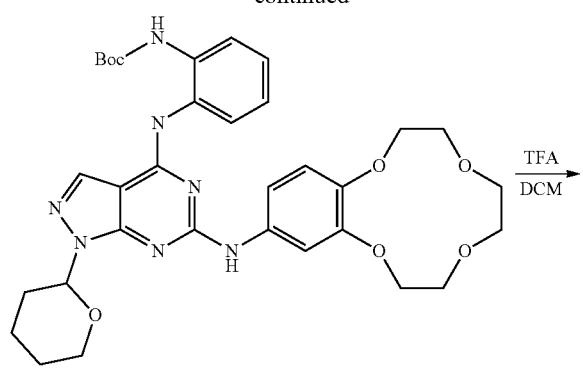

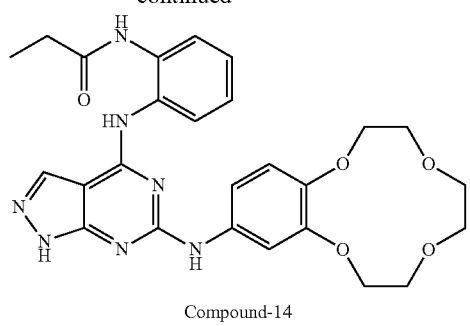

Compound-14

The synthetic schedule for Compound-14 is shown in Scheme 11, which is similar to the synthesis of Compound-13 in Scheme 10 except by using 4,6-dichloro-1-tetrahydropyran-2-yl-pyrazolo[3,4-d]pyrimidine (I-4) as starting material instead of 2,4-dichloropyrrolo[2,3-d] pyrimidin-7-yl) methyl 2,2-dimethylpropanoate.

LC-MS: m/z=519.9 (ES+, M+H).

$^1$HNMR (DMSO-$d_6$, 400 MHz) δ 12.9 (s, 1H), 9.58 (s, 1H), 9.18 (s, 1H), 7.71-7.64 (m, 3H), 7.63 (s, 1H), 7.26 (m, 3H), 6.87 (s, 1H), 4.03 (br s, 2H), 3.96 (br s, 2H), 3.64~3.72 (m, 8H), 2.30 (q, 2H, J=6 Hz), 1.03 (t, 3H, J=6 Hz).

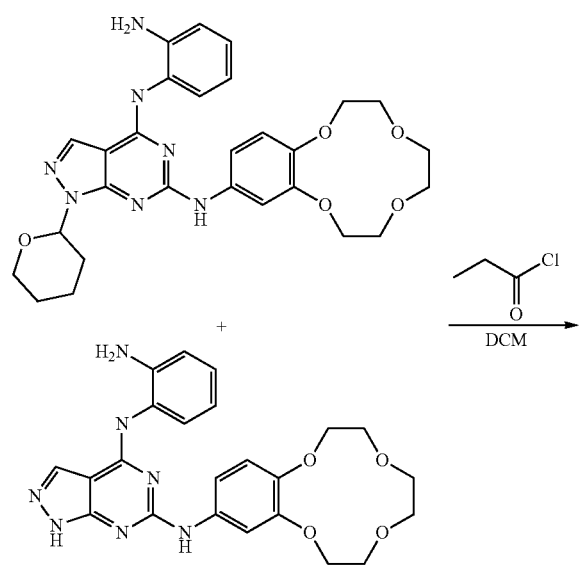

N-methoxy-2-[[6-(2,5,8,11-tetraoxabicyclo[10.4.0] hexadeca-1(16),12,14-trien-14-ylamino)-1H-pyrazolo[3,4-d]pyrimidin-4-yl]amino]benzamide (Compound-15)

Compound-15

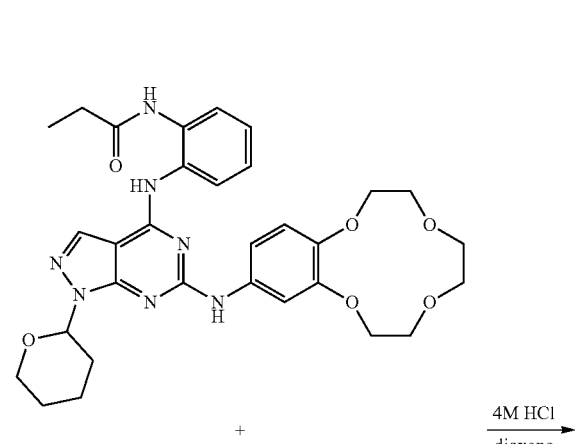

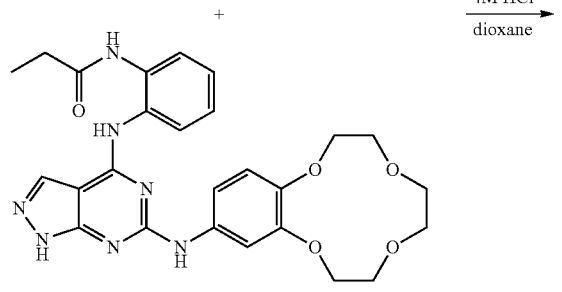

Compound-15 was made in the same way as described for Compound-14 in Scheme 11, starting from intermediates I-3 and I-4.

LC-MS: m/z=521.9 (ES+, M+H).

$^1$HNMR (DMSO-$d_6$, 400 MHz) δ 13.91 (s, 1H), 11.23 (s, 1H), 10.91 (s, 1H), 8.91 (br s, 1H), 8.78 (br s, 1H), 8.05 (d, 1H, J=6.0 Hz), 7.73 (t, 1H, J=6 Hz), 7.44 (t, 1H, J=5.6 Hz), 7.14 (dd, 1H, J=1.6, 6.8 Hz), 7.05 (d, 1H, J=1.6 Hz), 4.081 (br s, 2H), 4.03 (br s, 2H), 4.01 (s, 3H), 3.70 (s, 2H), 3.61 (br s, 4H), 3.59 (s, 2H).

N-methyl-N-[(1R,2R)-2-[[2-(2,5,8,11-tetraoxabicyclo[10.4.0]hexadeca-1(16),12,14-trien-14-ylamino)-7H-pyrrolo[2,3-d]pyrimidin-4-yl]oxy]cyclohexyl]methanesulfonamide (Compound-16)

N-methyl-N-[2-[[2-(2,5,8,11-tetraoxabicyclo[10.4.0]hexadeca-1(16),12,14-trien-14-ylamino)-7H-pyrrolo[2,3-d]pyrimidin-4-yl]oxy]cyclopentyl]methanesulfonamide (Compound-18)

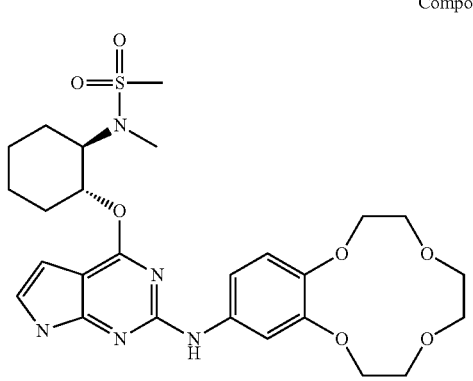

Compound-16

Compound-16 was made in the same way as described for Compound-13 in Scheme 10, starting from intermediate I-6 instead of tert-butyl N-(2-aminophenyl)carbamate.

LC-MS: m/z=561.9 (ES+, M+H).

$^1$HNMR (DMSO-d$_6$, 400 MHz) δ 11.41 (s, 1H), 8.93 (s, 1H), 7.57 (s, 1H), 7.32 (d, 1H, J=6.0 Hz), 6.95 (d, 2H, J=5.6 Hz), 6.25 (s, 1H), 5.37 (br s, 1H), 4.10 (br s, 2H), 4.01 (br s, 2H), 3.93 (br s, 2H), 3.91 (br s, 2H), 3.78 (m, 6H), 2.84 (s, 3H), 2.51 (s, 3H), 2.29 (br s, 1H), 1.75 (m 5H), 1.07-1.40 (m, 5H).

The title compound (Compound-18) was made in the same way as described for Compound-16 starting from intermediate I-7 instead of I-6.

LC-MS: m/z=547.9 (ES+, M+H).

$^1$HNMR (DMSO-d$_6$, 400 MHz) δ 11.51 (s, 1H), 8.90 (s, 1H), 7.58 (d, 1H, =3.2 Hz), 7.32 (d, 1H, J=6.0 Hz), 6.95 (m, 2H), 6.21 (br s, 1H), 5.37 (br s, 1H), 4.07 (br s, 2H), 4.01 (br s, 2H), 3.55~3.75 (m, 6H), 2.84 (s, 3H), 2.75 (s, 3H), 2.29 (br s, 1H), 1.96 (m, 1H), 1.72 (m, 4H).

N-methyl-N-[(1R,2R)-2-[[6-(2,5,8,11-tetraoxabicyclo[10.4.0]hexadeca-1(16),12,14-trien-14-ylamino)-1H-pyrazolo[3,4-d]pyrimidin-4-yl]oxy]cyclohexyl]methanesulfonamide (Compound-17)

N-methyl-N-[(1R,2R)-2-[[6-(2,5,8,11-tetraoxabicyclo[10.4.0]hexadeca-1(16),12,14-trien-14-ylamino)-1H-pyrazolo[3,4-d]pyrimidin-4-yl]oxy]cyclopentyl]methanesulfonamide (Compound-19)

Compound-17

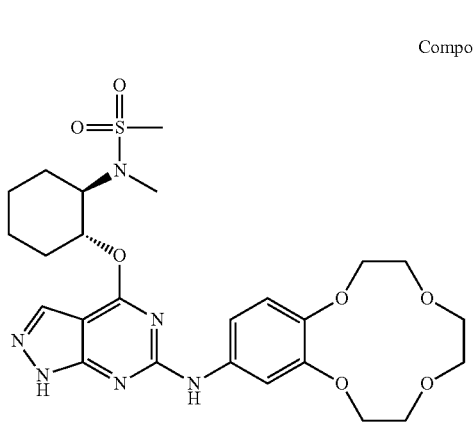

Compound-19

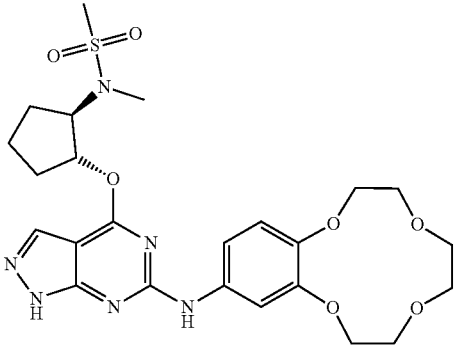

Compound-17 was made in the same way as described for Compound-15 in Scheme 11, starting from intermediate I-6 instead of tert-butyl N-(2-aminophenyl)carbamate.

LC-MS: m/z=562.9 (ES+, M+H).

$^1$HNMR (DMSO-d$_6$, 400 MHz) δ 13.20 (s, 1H), 9.36 (s, 1H), 7.82 (s, 1H), 7.55 (s, 1H), 7.35 (d, 1H, J=5.6 Hz), 6.98 (d, 1H, J=6.8 Hz), 5.41 (m, 1H), 4.16 (br s, 2H), 4.07 (br s, 2H), 3.90 (m, 1H), 3.77 (s, 2H), 3.71 (br s, 2H), 3.65 (s, 4H), 2.86 (s, 3H), 2.68 (s, 3H), 2.28 (m, 1H), 1.78 (m, 3H), 1.25~1.75 (m, 4H).

Compound-19 was made in the same way as described for Compound-16 starting from intermediate I-7 instead of I-6.

LC-MS: m/z=548.9 (ES+, M+H).

$^1$HNMR (DMSO-d$_6$, 400 MHz) δ 9.31 (s, 1H), 7.82 (s, 1H), 7.52 (s, 1H), 7.28 (d, 1H, =8.8 Hz), 5.54 (t, 1H, J=3.6 Hz), 4.36 (m, 1H), 4.06 (br s, 2H), 4.02 (br s, 2H), 3.71 (br s, 2H), 3.65 (br s, 2H), 3.60 (s, 4H), 2.84 (s, 3H), 2.73 (s, 3H), 2.29 (m, 1H), 1.96 (m, 1H), 1.72 (m, 4H).

N-methyl-N-[4-[[[2-(2,5,8,11-tetraoxabicyclo[10.4.0]hexadeca-1(16),12,14-trien-14-ylamino)-7H-pyrrolo[2,3-d]pyrimidin-4-yl]amino]methyl]-3-pyridyl]methanesulfonamide (Compound-20)

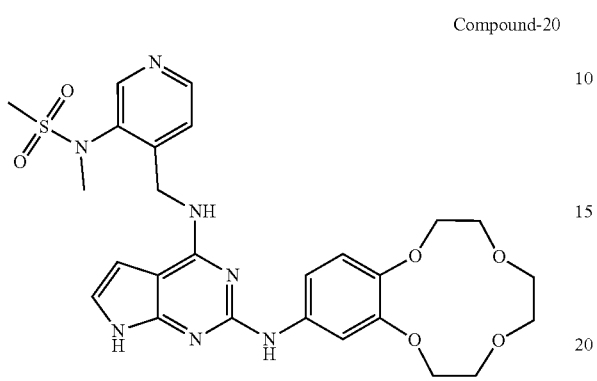

Compound-20

Compound-20 was made in the same way as described for Compound-16 starting from intermediate I-5 instead of I-6.

LC-MS: m/z=569.9 (ES+, M+H).

$^1$HNMR (DMSO-d$_6$, 400 MHz) δ 11.0 (s, 1H), 8.45 (s, 1H), 8.43 (s, 1H), 7.82 (d, 1H, =3.2 Hz), 7.75 (br t, 1H), 7.50 (s, 1H), 7.45 (d, 1H, J=6.0 Hz), 7.23 (d, 1H, J=6.0 Hz), 6.80 (s, 1H), 6.75 (s, 1H), 6.45 (s, 1H), 4.78 (s, 2H) 4.00 (br s, 2H), 3.95 (br s, 2H), 3.60~3.70 (m, 8H), 3.23 (s, 3H), 3.15 (s, 3H).

Synthesis of N-methyl-N-[4-[[[6-(2,5,8,11-tetraoxabicyclo[10.4.0]hexadeca-1(16),12,14-trien-14-ylamino)-1H-pyrazolo[3,4-d]pyrimidin-4-yl]amino]methyl]-3-pyridyl]methanesulfonamide (Compound-21)

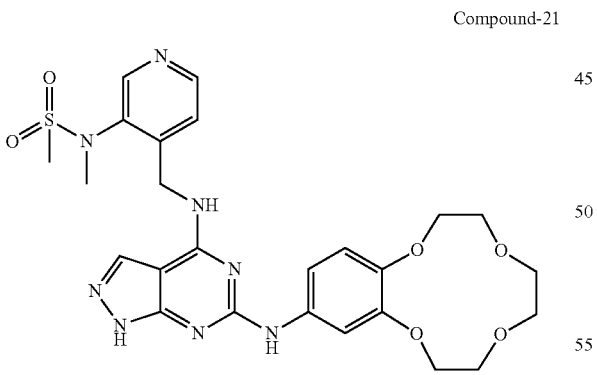

Compound-21

Compound-21 was made in the same way as described for Compound-15 in Scheme 11, starting from intermediate I-5 instead of tert-butyl N-(2-aminophenyl)carbamate.

LC-MS: m/z=570.9 (ES+, M+H).

$^1$HNMR (DMSO-d$_6$, 400 MHz) δ 10.02 (br s, 1H), 8.49 (d, 1H, =8 Hz), 7.86 (d, 1H, J=8 Hz), 7.43 (dd, 1H, J=8, 10 Hz), 7.25 (s, 1H), 6.97 (m, 2H), 4.86 (d, 2H, J=6 Hz), 4.05 (br s, 2H), 3.93 (br s, 2H), 3.60~3.70 (m, 8H), 3.17 (s, 3H), 3.13 (s, 3H).

Synthesis of N6-(1H-indol-4-yl)-N2-(2,5,8,11-tetraoxabicyclo[10.4.0]hexadeca-1(12),13,15-trien-14-yl)-9H-purine-2,6-diamine (Compound-22)

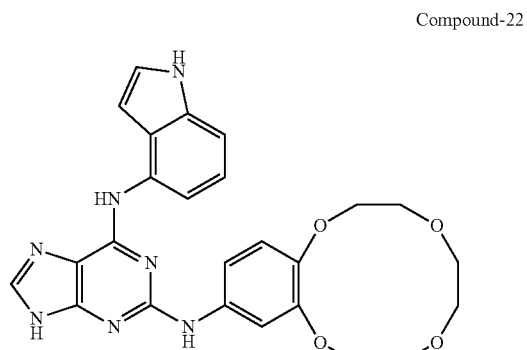

Compound-22

Compound-22 was made in the same way as described in Scheme 5 starting from 1H-indol-4-amine.

LC-MS: m/z=487.9 (ES+, M+H).

$^1$HNMR (DMSO-d$_6$, 400 MHz) δ 12.60 (s, 1H), 11.14 (s, 1H), 8.87 (s, 1H), 8.77 (s, 1H), 7.98 (d, 1H, =4 Hz), 7.69 (s, 1H), 7.52 (s, 1H), 7.29 (s, 1H), 7.24 (d, 1H, J=8 Hz), 7.20 (d, 1H, J=8 Hz), 6.82 (d, 1H, J=8 Hz), 6.54 (s, 1H), 6.42 (m, 1H), 4.00 (br s, 2H), 3.81 (br s, 2H), 3.62~3.67 (br d, 8H).

Synthesis of N6-(1H-indol-7-yl)-N2-(2,5,8,11-tetraoxabicyclo[10.4.0]hexadeca-1(12),13,15-trien-14-yl)-9H-purine-2,6-diamine (Compound-23)

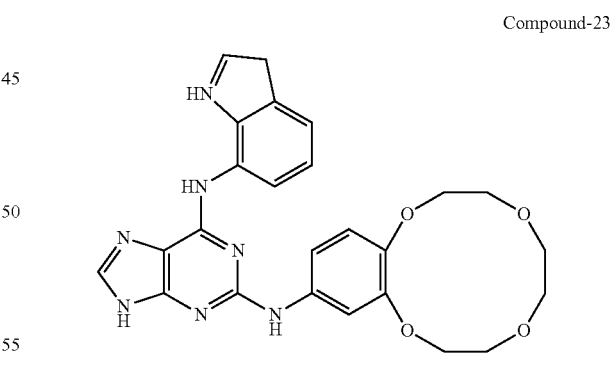

Compound-23

Compound-23 was made in the same way as described in Scheme-5 starting from 1H-indol-7-amine.

LC-MS: m/z=487.9 (ES+, M+H).

$^1$HNMR (DMSO-d$_6$, 400 MHz) δ 11.20 (s, 1H), 9.23 (s, 1H), 8.68 (s, 1H), 7.94 (s, 1H), 7.70 (t, 1H, =4 Hz), 7.46 (s, 1H), 7.32 (d, 1H, J=8 Hz), 7.28 (d, 1H, J=4 Hz), 6.99 (d, 1H, J=8 Hz), 6.76 (d, 1H, J=8 Hz), 6.45 (s, 1H), 4.00 (br s, 2H), 3.82 (br s, 2H), 3.62~3.67 (m, 8H).

Synthesis of N-methyl-N-[(1R,2R)-2-[2-(2,5,8,11-tetraoxabicyclo[10.4.0]hexadeca-1(12),13,15-trien-14-ylamino)thieno[2,3-d]pyrimidin-4-yl]oxycyclopentyl]methanesulfonamide (Compound-24)

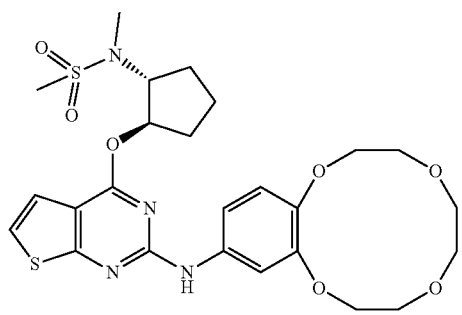

Compound-24

The title compound (Compound-24) was made in the same way as described for Compound-18 starting from 2,4-dichlorothieno[2,3-d]pyrimidine and key intermediates I-5.

LC-MS: m/z=564.9 (ES+, M+H).

$^1$HNMR (CDCl$_3$, 400 MHz) δ 7.44 (s, 1H), 7.15 (d, 1H, =4 Hz), 7.11 (d, 1H, J=8 Hz), 6.96 (m, 3H), 5.51 (m, 1H), 4.56 (q, 1H, J=8 Hz), 4.22 (br s, 2H), 4.18 (br s, 2H), 3.90 (br s, 2H), 3.85 (br s, 2H), 3.81 (s, 4H), 2.85 (s, 3H), 2.79 (s, 3H), 2.31 (m, 1H), 2.02 (m, 1H), 1.80 (m, 4H).

N-[5-methyl-2-[[6-(2,5,8,11-tetraoxabicyclo[10.4.0]hexadeca-1(12),13,15-trien-14-ylamino)-1H-pyrazolo[3,4-d]pyrimidin-4-yl]amino]phenyl]prop-2-enamide (Compound-26)

The title compound was prepared in the same way as described in Scheme 11 by using N-(2-aminophenyl)propanamide in the Cl-displacement step reacting with 4,6-dichloro-1-tetrahydropyran-2-yl-pyrazolo[3,4-d]pyrimidine, followed by Pd-mediated aryl amination with 2,5,8,11-tetraoxabicyclo[10.4.0]hexadeca-1(16),12,14-trien-14-amine.

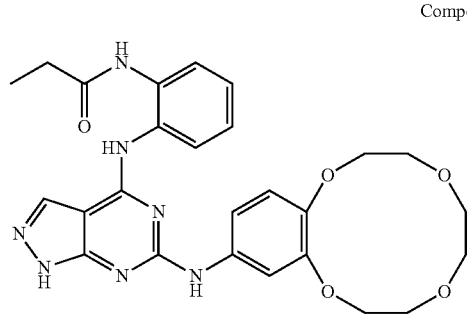

Compound-26

The title compound was prepared in the same way as described in Scheme 11 by using tert-butyl N-(2-amino-5-methyl-phenyl)carbamate in the Cl-displacement step reacting with 4,6-dichloro-1-tetrahydropyran-2-yl-pyrazolo[3,4-d]pyrimidine, followed by Pd-mediated aryl amination with 2-[2-(4-amino-2-methoxy-phenoxy)ethoxy]ethanol, and final acryloylation after Boc-deprotection.

LC-MS: m/z 532.2 (ES+, M+H).

HNMR (DMSO-d6, 300 MHz) δ 9.86 (s, 1H), 9.72 (s, 1H), 9.21 (s, 1H), 8.87 (s, 1H), 7.59 (s, 1H), 7.50 (s, 1H), 7.44 (d, 1H, J=6 Hz), 7.21 (br s, 1H), 7.02 (t, 1H, J=6 Hz), 6.82 (d, 1H, J=6 Hz), 6.44 (dd, 1H, J=6, 12 Hz), 6.18 (d, 1H, J=12 Hz), 5.68 (m, 1H), 3.99 (d, 2H, J=6 Hz), 3.90 (br s, 1H), 3.67 (s, 2H), 3.64 (s, 2H), 3.59 (s, 4H), 2.31 (s, 3H).

N-[5-methyl-2-[[2-(2,5,8,11-tetraoxabicyclo[10.4.0]hexadeca-1(12),13,15-trien-14-ylamino)-9H-purin-6-yl]amino]phenyl]acetamide (Compound-27)

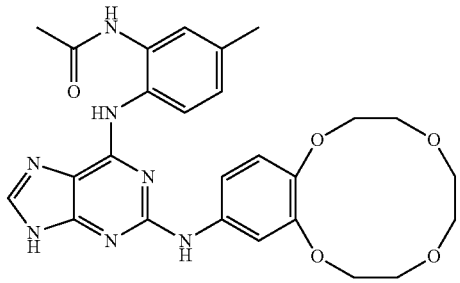

Compound-27

The title compound was prepared in the same way as describes in Scheme 11 by using N-(2-amino-5-methyl-phenyl)acetamid in the Cl-displacement step reacting with (2,6-dichloropurin-9-yl)methyl 2,2-dimethylpropanoate, followed by Pd-mediated aryl amination with 2,5,8,11-tetraoxabicyclo[10.4.0]hexadeca-1(16),12,14-trien-14-amine.

LC-MS: m/z 520.4 (ES+, M+H).

HNMR (DMSO-d6, 300 MHz) δ 9.82 (s, 1H), 8.72 (s, 1H), 8.56 (s, 1H), 7.86 (s, 1H), 7.71 (d, 1H, J=6 Hz), 7.48 (d, 1H, J=6 Hz), 7.19 (m, 2H), 7.00 (d, 1H, J=6 Hz), 6.82 (d, 1H, J=6 Hz), 3.98 (d, 2H, J=6 Hz), 3.90 (br s, 1H), 3.67 (s, 2H), 3.64 (s, 2H), 3.59 (s, 4H), 2.27 (s, 3H), 2.01 (s, 3H).

N-[5-fluoro-2-[[2-(2,5,8,11-tetraoxabicyclo[10.4.0]hexadeca-1(12),13,15-trien-14-ylamino)-9H-purin-6-yl]amino]phenyl]acetamide (Compound-28)

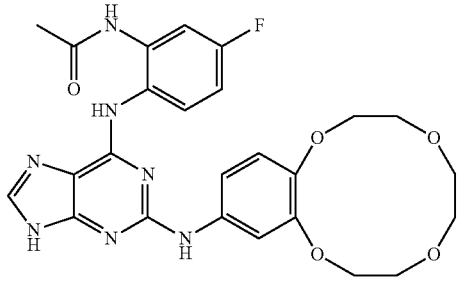

Compound-28

The title compound was prepared in the same way as describe in Scheme 11 by using N-(2-amino-5-fluoro-phenyl)acetamide in the Cl-displacement step reacting with (2,6-dichloropurin-9-yl)methyl 2,2-dimethylpropanoate, followed by Pd-mediated aryl amination with 2,5,8,11-tetraoxabicyclo[10.4.0]hexadeca-1(16),12,14-trien-14-amine.

LC-MS: m/z 524.4 (ES+, M+H).

HNMR (DMSO-d6, 300 MHz) δ 9.85 (s, 1H), 8.91 (s, 1H), 8.60 (s, 1H), 7.99 (d, 1H, J=6 Hz), 7.91 (s, 1H), 7.44 (d, 1H, J=3 Hz), 7.31 (m, 2H), 6.92 (m, 1H), 6.85 (d, 1H, J=6 Hz), 3.98 (d, 2H, J=6 Hz), 3.90 (br s, 1H), 3.67 (s, 2H), 3.64 (s, 2H), 3.59 (s, 4H), 2.05 (s, 3H).

N-[2-[[2-(2,5,8,11-tetraoxabicyclo[10.4.0]hexadeca-1(12),13,15-trien-14-ylamino)-9H-purin-6-yl]amino]-5-(trifluoromethyl)phenyl]acetamide (Compound 29)

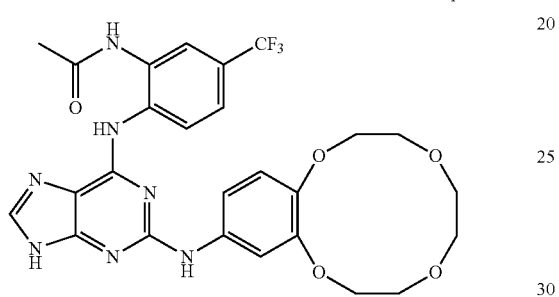

Compound-29

The title compound was prepared in the same way as described in Scheme 11 by using N-[2-amino-5-(trifluoromethyl)phenyl]acetamide in the Cl-displacement step reacting with (2,6-dichloropurin-9-yl)methyl 2,2-dimethylpropanoate, followed by Pd-mediated aryl amination with 2,5,8,11-tetraoxabicyclo[10.4.0]hexadeca-1(16),12,14-trien-14-amine.

LC-MS: m/z 574.4 (ES+, M+H).

HNMR (DMSO-d6, 300 MHz) δ 9.85 (s, 1H), 8.91 (s, 1H), 8.60 (s, 1H), 7.99 (d, 1H, J=6 Hz), 7.91 (s, 1H), 7.44 (d, 1H, J=3 Hz), 7.31 (m, 2H), 6.92 (m, 1H), 6.85 (d, 1H, J=6 Hz), 3.98 (d, 2H, J=6 Hz), 3.90 (br s, 1H), 3.67 (s, 2H), 3.64 (s, 2H), 3.59 (s, 4H), 2.05 (s, 3H).

N-[3-[5-fluoro-2-(2,5,8,11-tetraoxabicyclo[10.4.0]hexadeca-1(12),13,15-trien-14-ylamino)pyrimidin-4-yl]phenyl]prop-2-enamide (Compound-30)

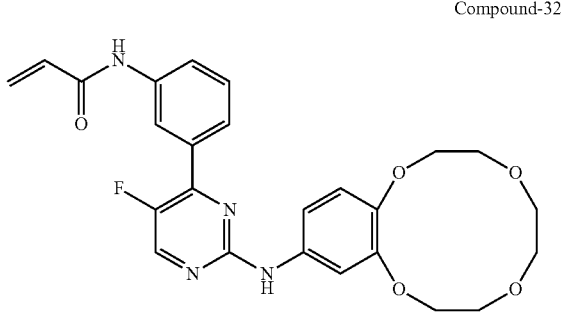 [SMILES: C=CC(=O)Nc1cccc(-c2nc(Nc3ccc4c(c3)OCCOCCOCCO4)ncc2F)c1]

Compound-32

The title compound was made through Suzuki reaction of (3-aminophenyl)boronic acid with 2,4-dichloro-5-F-pyrimidine, followed by acryloylation and Pd-mediated aryl amination with 2,5,8,11-tetraoxabicyclo[10.4.0]hexadeca-1(16),12,14-trien-14-amine.

LC-MS: m/z 481.2 (ES+, M+H).

HNMR (DMSO-d6, 300 MHz) δ 10.30 (s, 1H), 9.60 (s, 1H), 8.58 (s, 1H), 8.39 (s, 1H), 7.79 (d, 1H, J=6 Hz), 7.71 (d, 1H, J=6 Hz), 7.58 (s, 1H), 7.51 (t, 1H, J=6 Hz), 7.24 (d, 1H, J=6 Hz), 6.94 (d, 1H, J=6 Hz), 6.44 (dd, 1H, J=6, 12 Hz), 6.24 (d, 1H, J=12 Hz), 5.75 (m, 1H), 3.99 (d, 2H, J=6 Hz), 3.90 (br s, 1H), 3.67 (s, 2H), 3.64 (s, 2H), 3.59 (s, 4H).

N-methyl-N-[(1R,2R)-2-[[2-(2,5,8,11-tetraoxabicyclo[10.4.0]hexadeca-1(12),13,15-trien-14-ylamino)-9H-purin-6-yl]oxy]indan-1-yl]methanesulfonamide (Compound-31)

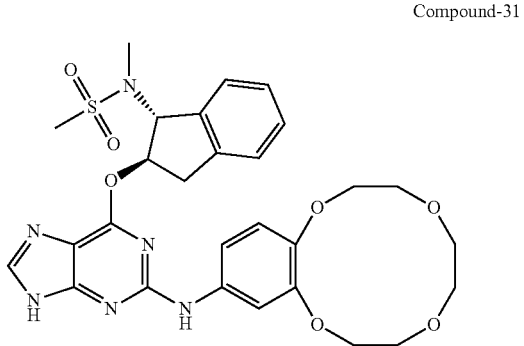 [SMILES: CN([C@@H]1c2ccccc2C[C@H]1Oc1nc(Nc2ccc3c(c2)OCCOCCOCCO3)nc2[nH]cnc12)S(C)(=O)=O]

Compound-31

The title compound was prepared in the same way as described in Scheme 5 by using N-[(1R,2R)-2-hydroxyindan-1-yl]-N-methyl-methanesulfonamide in the Cl-displacement step reacting with (2,6-dichloropurin-9-yl)methyl 2,2-dimethylpropanoate in the presence of cesium carbonate in dioxane, followed by Pd-mediated aryl amination with 2,5,8,11-tetraoxabicyclo[10.4.0]hexadeca-1(16),12,14-trien-14-amine.

LC-MS: m/z 597.2 (ES+, M+H).

HNMR (DMSO-d6, 300 MHz) δ 12.72 (s, 1H), 9.19 (s, 1H), 7.96 (s, 1H), 7.57 (s, 1H), 7.32 (m, 3H), 7.17 (m, 2H), 6.90 (d, 1H, J=6 Hz), 5.83 (m, 1H), 5.61 (d, 1H, J=6 Hz), 3.98 (d, 2H, J=6 Hz), 3.90 (br s, 1H), 3.67 (s, 2H), 3.64 (s, 2H), 3.59 (s, 4H), 3.03 (s, 3H), 2.62 (s, 3H).

N-methyl-N-[(1R,2R)-2-[[2-(2,5,8,11-tetraoxabicyclo[10.4.0]hexadeca-1(12),13,15-trien-14-ylamino)-5-(trifluoromethyl)-4-pyridyl]oxy]indan-1-yl]methanesulfonamide (Compound-32)

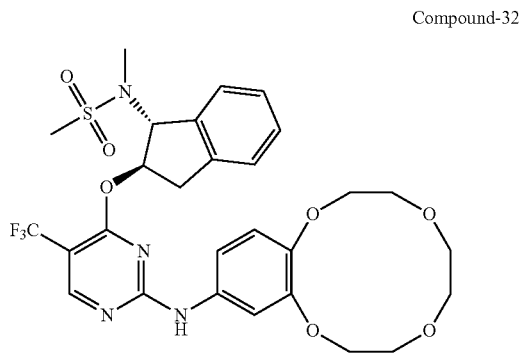 [SMILES: CN([C@@H]1c2ccccc2C[C@H]1Oc1nc(Nc2ccc3c(c2)OCCOCCOCCO3)ncc1C(F)(F)F)S(C)(=O)=O]

Compound-32

The title compound was made through iodo-displacement of 2-chloro-4-iodo-5-(trifluoromethyl) pyridine by N-[(1R,2R)-2-hydroxyindan-1-yl]-N-methyl-methanesulfonamide in the presence of sodium hydride in dioxane, followed by Pd-mediated aryl amination with 2,5,8,11-tetraoxabicyclo[10.4.0]hexadeca-1(16),12,14-trien-14-amine.

LC-MS: m/z 624.4 (ES+, M+H).

HNMR (DMSO-d6, 300 MHz) δ 9.25 (s, 1H), 8.22 (s, 1H), 7.32 (m, 4H), 7.23 (m, 1H), 7.09 (m, 1H), 6.95 (d, 1H, J=6 Hz), 6.57 (s, 1H), 5.53 (d, 1H, J=6 Hz), 5.30 (m, 1H), 3.98 (d, 2H, J=6 Hz), 3.90 (br s, 1H), 3.67 (s, 2H), 3.64 (s, 2H), 3.59 (s, 4H), 2.97 (s, 3H), 2.59 (s, 3H).

Example 1. Inhibitive Activities Against BTK Wt, BTK(C481S), BMX, FAK, ITK, EGFR Wt Kinases The inhibiting activities of each of Compound-1 to Compound-24 against BTK wt, BTK(C481S), BMX, FAK, ITK, and EGFR wt kinases were determined using $^{33}$P ATP "HotSpot" kinase assay platform. (See, e.g., Ma, et al, 2008 Expert Opin Drug Discov. 3(6): 607-621.)

Each of Compound-1 to Compound-24 were prepared as 10 mM DMSO solution, and then 1:3 serially diluted to a concentration of 1 M to 0.05 nM. Then, Kinase assays were performed using the "HotSpot" assay platform.

Briefly, specific kinase/substrate pairs along with required cofactors were prepared in reaction buffer; 20 mM Hepes pH 7.5, 10 mM $MgCl_2$, 1 mM EGTA, 0.02% Brij35, 0.02 mg/ml BSA, 0.1 mM $Na_3VO_4$, 2 mM DTT, 1% DMSO. Compounds were delivered into the reaction, followed about 20 minutes later by addition of a mixture of ATP (Sigma, St. Louis MO) and $^{33}$P ATP (Perkin Elmer, Waltham MA) to a final concentration of 10 μM.

Reactions were carried out at room temperature for 120 min, followed by spotting of the reactions onto P81 ion exchange filter paper (Whatman Inc., Piscataway, NJ). Unbound phosphate was removed by extensive washing of filters in 0.75% phosphoric acid. After subtraction of background derived from control reactions containing inactive enzyme, kinase activity data was expressed as the percent remaining kinase activity in test samples compared to vehicle (dimethyl sulfoxide) reactions. $IC_{50}$ values and curve fits were obtained using Prism (GraphPad Software).

The results are shown in Table 2.

TABLE 2

Inhibitory Activities $IC_{50}$ (nm) of Exemplary Compounds

| Compound No. | BMX | BTK | BTK (C481S) | EGFR | FAK | ITK |
| --- | --- | --- | --- | --- | --- | --- |
| 1 | <100 nM | 100.00 | | >100 nM | >100 nM | >100 nM |
| 2 | 8.46 | 73.37 | | >>1000 | >>1000 | >>1000 |
| 3 | 1.69 | 3.17 | >1000 | 345.20 | 1236.00 | 39.56 |
| 4 | 19.55 | 143.90 | | >>1000 | 1150.00 | 1450.00 |
| 5 | <100 nM | <100 nM | | >100 nM | >100 nM | <100 nM |
| 6 | <100 nM | <100 nM | >1000 | 732.00 | >1000 | <100 nM |
| 7 | 0.41 | 0.65 | 323.5; 675.0 | 207.60 | 274.30 | 1.35 |
| 8 | 46.37 | 88.79 | | >>1000 | 1130.00 | 1290.00 |
| 9 | >100 nM | >100 nM | | >100 nM | >100 nM | >100 nM |
| 10 | >100 nM | <100 nM | | >100 nM | >100 nM | >100 nM |
| 11 | 1.21 | 2.33 | 9.88; 4.46 | 1904.00 | 17.40 | 270.30 |
| 12 | 2.70 | 4.36 | 14.1 | >>1000 | 24.58 | 447.40 |
| 13 | | | >1000 | | 57.53 | |
| 14 | | | 108.70 | | 192.40 | |
| 15 | | | 378.90 | | 381.70 | |
| 16 | | >1000 | >1000 | >1000 | 34.92 | |
| 17 | | | 219.70 | | 77.64 | |
| 18 | | >1000 | >1000 | >1000 | 12.69 | |
| 19 | | 68.19 | 118.80 | >1000 | 13.45 | |
| 20 | | >1000 | >>1000 | >1000 | 29.35 | |
| 21 | | | 130.10 | | 156.40 | |
| 22 | | 21.35 | 128.20 | >1000 | 42.35 | |
| 23 | | 62.77 | 341.50 | >1000 | 257.40 | |
| 26 | | 33.31 | 88.59 | | 845 | |
| 27 | | 16.77 | 86.69 | | 98.81 | |
| 28 | | 9.37 | 31.50 | | 83.40 | |
| 29 | | 67.10 | 155.00 | | 211.00 | |
| 30 | | 613.40 | >1000 | | >1000 | |
| 31 | | 198.00 | 345.00 | | 377.30 | |
| 32 | | >10000 | >1000 | | 4.96 | |

Example 2. Inhibitive Activities Against BTK Wt, BTK(C481S), EGFR Wt Kinases

TABLE 3

Inhibitory Activities against BTK wt, BTK(C481S), EGFR

| Compound No. | BTK | BTK(C481S) | EGFR |
|---|---|---|---|
| | $IC_{50}$ (nM) | | |
| 1 | 100.00 | | >100 |
| 2 | 73.37 | | >>1000 |
| 3 | 3.17 | >1000 | 345.20 |
| 4 | 143.90 | | >>1000 |
| 5 | <100 | | >100 |
| 6 | <100 | >1000 | 732.00 |
| 7 | 0.65 | 675.00 | 207.60 |
| 8 | 88.79 | | >>1000 |
| 10 | <100 | | >100 |
| 11 | 2.33 | 9.88 | >>1000 |
| 12 | 4.36 | 14.1 | >>1000 |
| 14 | | 108.70 | |
| 15 | | 378.90 | |
| 17 | | 219.70 | |
| 19 | 68.19 | 118.80 | >1000 |
| 21 | | 130.10 | |
| 22 | 21.35 | 128.20 | >1000 |
| 23 | 62.77 | 341.50 | >1000 |
| 26 | 33.31 | 88.59 | |
| 27 | 16.77 | 86.69 | |
| 28 | 9.37 | 31.50 | |
| 29 | 67.10 | 155.00 | |
| 30 | 613.40 | >1000 | |
| 31 | 198.00 | 345.00 | |
| 32 | >10000 | >1000 | |

As shown in Table 3, many compounds showed an excellent inhibition activity against BTK and BTK(C481S) mutant having a resistance to the commercially marketable BTK inhibitor Ibrutinib ($IC_{50}$=A, <50 nM), while it showed a relatively low inhibition activity against EGFR WT related with the adverse effects ($IC_{50}$=C or D). Like the results from Example 1, such inhibitory mechanisms of the compounds are very different from those of the commercially marketable BTK tyrosine kinase inhibitor Ibrutinib. Therefore, the compounds are potentially effective and safe drug for cancer patients by showing an effectively excellent inhibition activity against BTK and BTK mutant (C481S) with no inhibition activity against EGFR WT expressed in normal cells.

Example 3. Inhibitive Activities Against FAK Kinase

The inhibiting activities of certain compounds of Compound-1 to Compound-32 against FAK kinase were determined, respectively. The procedure of kinase assay was the same as described above, except that FAK kinase were used. The results are shown in Table 4.

TABLE 4

Inhibitory Activities against FAK

| Compound No. | $IC_{50}$(nM) - FAK |
|---|---|
| 7 | 274.30 |
| 11 | 17.40 |
| 12 | 24.58 |
| 13 | 57.53 |
| 14 | 192.40 |
| 15 | 381.70 |
| 16 | 34.92 |

TABLE 4-continued

Inhibitory Activities against FAK

| Compound No. | $IC_{50}$(nM) - FAK |
|---|---|
| 17 | 77.64 |
| 18 | 12.69 |
| 19 | 13.45 |
| 20 | 29.35 |
| 21 | 156.40 |
| 22 | 42.35 |
| 23 | 257.40 |
| 24 | 1127.00 |
| 26 | 845 |
| 27 | 98.81 |
| 28 | 83.40 |
| 29 | 211.00 |
| 30 | >1000 |
| 31 | 377.30 |
| 32 | 4.96 |

As shown in Table 4 and FIG. 6, the compounds showed inhibitory activity against FAK kinase.

Example 4. Inhibitive Activities Against BTK, BTK(C481S) and FAK Kinases

Certain compounds of Compound-1 to Compound-32 were measured for its inhibitory activity on BTK, BTK(C481S) and FAK. The measurement was carried out in the same process as described above, BTK, BTK(C481S) and FAK enzymes were used. The results are shown in Table 5.

TABLE 5

Inhibitory Activities against BTK, BTK(C481S), FAK

| Compound No. | BTK | BTK(C481S) | FAK | EGFR |
|---|---|---|---|---|
| | $IC_{50}$ (nM) | | | |
| 7 | 0.65 | 675.00 | 274.30 | 207.60 |
| 11 | 2.33 | 9.88 | 17.40 | 1904.00 |
| 12 | 4.36 | 14.1 | 24.58 | >1000 |
| 13 | | >1000 | 57.53 | |
| 14 | | 108.70 | 192.40 | |
| 15 | | 378.90 | 381.70 | |
| 16 | >1000 | >1000 | 34.92 | >1000 |
| 17 | | 219.70 | 77.64 | |
| 18 | >1000 | >1000 | 12.69 | >1000 |
| 19 | 68.19 | 118.80 | 13.45 | >1000 |
| 20 | >1000 | >1000 | 29.35 | >1000 |
| 21 | | 130.10 | 156.40 | |
| 22 | 21.35 | 128.20 | 42.35 | >1000 |
| 23 | 62.77 | 341.50 | 257.40 | >1000 |
| 26 | 33.31 | 88.59 | 845 | |
| 27 | 16.77 | 86.69 | 98.81 | |
| 28 | 9.37 | 31.50 | 83.40 | |
| 29 | 67.10 | 155.00 | 211.00 | |
| 30 | 613.40 | >1000 | >1000 | |
| 31 | 198.00 | 345.00 | 377.30 | |
| 32 | >10000 | >1000 | 4.96 | |

As shown in Table 5, certain compounds of Compound-1 to Compound-24 effectively inhibited BTK, BTK(C481S), FAK kinases, but not EGFR wt. As shown in FIGS. 2, 3 and 6, certain compounds of Compound-1 to Compound-24 effectively inhibited BTK(FIG. 2), BTK(C481S) (FIG. 3), FAK (FIG. 6) kinases.

Example 5. Inhibitory Activities Against BMX and ITK Kinases

Each of Compound-1 to Compound-24 was measured for its inhibitory activity on TEC family kinases, BMX and ITK.

The measurement was carried out in the same process as described above, BMX, ITK enzymes were used. The results are shown in Table 6.

TABLE 6

Inhibitory Activities against BMX and ITK

| Compound No. | IC$_{50}$ (nM) | |
| --- | --- | --- |
| | BMX | ITK |
| 1 | <100 | >100 |
| 2 | 8.46 | >1000 |
| 3 | 1.69 | 39.56 |
| 4 | 19.55 | 1450.00 |
| 5 | <100 | <100 |
| 6 | <100 | <100 |
| 7 | 0.41 | 1.35 |
| 8 | 46.37 | 1290.00 |
| 11 | 1.21 | 270.30 |
| 12 | 2.70 | 447.40 |

As shown in Table 6, certain compounds of Compound-1 to Compound-24 according to the present invention effectively inhibited TEC family kinases such as BMX and ITK kinases. As shown in FIGS. 4 and 5, Certain compounds of Compound-1 to Compound-24 effectively inhibited TEC family kinases such as BMX (FIG. 4) and ITK (FIG. 5) kinases.

Example 6. Inhibitory Activities Against ERK Kinase

Certain compounds of Compound-1 to Compound-24 were measured for its inhibitory activity on ERK1 kinase. The measurement was carried out in the same process as described above, ERK enzyme was used. The results are shown in Table 7.

TABLE 7

Inhibitory Activities against ERK

| Compound No. | IC$_{50}$ (nM) - ERK1 |
| --- | --- |
| 11 | 6.23 |
| 12 | 713.7 |

As shown in Table 7 and FIG. 7, certain compounds of Compound-1 to Compound-24 according to the present invention effectively inhibited ERK1 kinase.

Example 7. Inhibitory Activities Against BTK in Cells

Immunoblot Analysis of Phospho-BTK(Y223)

Ramos cells were cultured in RPMI-1640 medium with 10% fetal bovine serum (FBS) and 1% penicillin/streptomycin (Gibco BRL). Before the assay, Ramos cells were counted and seeded at 1×10$^6$ cells/mL, cultured overnight in RPMI-1640 medium with 10% FBS, the cells were centrifuged at 950 rpm for 10 min., then 1~2×10$^6$ cells were split into each tube in 300 µL medium. The cells were treated with certain compounds of Compound 1-24 at 0~3 µM for 1 hr. in 37° C., then the cells were stimulated with 10 µg/mL of anti-IgM (BioLegend) for 5 min., followed by 3 min. spin at 2000 rpm. After aspirating the supernatant, 60 µL of RIPA lysis buffer (50 mM Tris-HCl, 1 mM EDTA, 1% NP-40, 0.5% sodium deoxycholate, and 0.1% SDS, pH 7.4, 150 mM NaCl, 1 mM Na$_3$VO$_4$) was added to the cell pellet to lyse the cells on ice for 30 min. After spin at 10,000 rpm for 5 min., 60 µL of the cell lysate was transferred to a fresh tube, and 20 µL of 4×LDS buffer was added to the tube. The samples were boiled on a 100° C. heat block for 10 min. 25 µL lysate was loaded on to SDS-PAGE gel (NuPAGE™ Novex™ 4-12% Bis-Tris Midi Protein Gels, cat. no. WG1402BOX, ThermoFisher) for western blotting analysis per the manufacturer's instructions. Antibodies used for immunoblot analysis include Btk and p-Btk(Y223) (cat. no. 3553 and 5082; Cell Signaling Technology, Beverly, MA). p-Btk (Y223) (cat. no. GTX61791; GeneTex, Inc., Irvine, CA). Membranes were detected using infrared fluorescence dye (IRDye® 800CW Donkey anti-Rabbit IgG (H+L), cat. no. P/N 925-32213; IRDye® 680RD Donkey anti-Mouse IgG (H+L), cat. no. P/N 925-68072 and scanned on a LiCor Odyssey scanner (LiCor Biosciences, Lincoln, NB).

EC$_{50}$, the concentration at which 50% inhibition occurs, was evaluated based on the phospho-BTK(Y223) signal difference in the cell lysates between the cells treated with the test compound and not-treated which was regarded as 100%. EC$_{50}$ results are shown in Table 8, wherein A means that EC$_{50}$<100 nM, B means that EC$_{50}$ is 100-1,000 nM.

TABLE 8

Inhibitory Activity against BTK

| Compound No. | EC$_{50}$ (nM) |
| --- | --- |
| 1 | B |
| 2 | B |
| 3 | A |
| 5 | A |
| 6 | A |
| 7 | A |
| 8 | B |
| 4 | B |
| 10 | B |
| 11 | B |
| 12 | B |

As shown in Table 8, many compounds showed inhibitory activity against BTK phosphorylation at tyrosine 223 in Ramos cancer cells.

As shown in FIG. 1, many compounds showed inhibitory activity against BTK phosphorylation at tyrosine 223 in Ramos cancer cells.

Example 8. Inhibitory Activity Against FAK in Cells

Cell-Based FAK(Y397) Phosphorylation Assay

PC3 cells were cultured in RPMI-1640 medium with 10% fetal bovine serum (FBS) and 1% penicillin/streptomycin (Gibco BRL). Before the assay, PC3 cells were counted and seeded at 1~3×10$^6$ cells/well in a 6-well plate, cultured overnight in RPMI-1640 medium with 10% FBS. The cells were treated with certain compounds of Compounds 1-24 at 0~3 µM for 1 hr. in 37° C., then the cells were scraped off, followed by 5 min. spin at 2000 rpm. After aspirating the supernatant, 100 µL of RIPA lysis buffer (50 mM Tris-HCl, 1 mM EDTA, 1% NP-40, 0.5% sodium deoxycholate, and 0.1% SDS, pH 7.4, 150 mM NaCl, 1 mM Na$_3$VO$_4$) was added to the cell pellet to lyse the cells on ice for 30 min. After spin at 12,000 rpm for 5 min., 90 µL of the cell lysate was transferred to a fresh tube.

For an enzyme-linked immunosorbent assay (ELISA) assay, 10 µL of the lysate was used for p-FAK(Y397) elisa assay. ELISA was done using the FAK [pY397] Phospho- ELISA Kit (ThermoFisher Scientific, KH00441) according to the manufacturer's instructions. Briefly, a monoclonal capture antibody specific for FAK has been coated onto the wells of the 96-well plate provided. During the first incubation, 50 μL standards of known p-FAK (Y397) content and compound treated samples (10 μL lysate) plus 40 μL diluent buffer were pipetted into the wells and let the p-FAK antigen standards and samples bind to the immobilized (capture) antibody on the plate, a rabbit antibody specific for p-FAK (Y397) 50 μL/well was added to the wells, this antibody serves as a detection antibody by binding to the p-FAK protein during a 3 hr. incubation at room temperature. After washing 4 times, a horseradish peroxidase labeled anti-rabbit IgG was added. This binds to the detection antibody. After a 30 min. incubation and washing to remove all the unbound enzyme, a substrate solution (TMB) was added, which was acted upon by the bound enzyme to produce color. The intensity of this colored product was directly proportional to the concentration of p-FAK(Y397) present in the samples and the optical density can be read on a standard microplate reader at 450 nM.

$EC_{50}$, the concentration at which 50% inhibition occurs, was evaluated based on the phospho-FAK(Y397) signal difference between the cells in a well treated with the test compound and not-treated which was regarded as 100%. The calculation of $EC_{50}$ and the result analysis were carried out using Microsoft Excel, and the results are shown in Table 9, wherein A means that $EC_{50}$<100 nM, B means that $EC_{50}$ is 100-1,000 nM, C means that $EC_{50}$ is 1,000-3,000 nM, and D means that $EC_{50}$>3,000 nM.

TABLE 9

Inhibitory Activity against FAK in Cells

| Compound No. | $EC_{50}$ (nM) |
|---|---|
| 11 | A |
| 18 | A |
| 19 | B |
| 20 | B |

As shown in Table 9, many compounds showed inhibitory activity against FAK phosphorylation at tyrosine 397 in PC3 cancer cells.

For western blotting analysis, to the 90 lysate, 30 μL of 4×LDS buffer was added. The samples were boiled on a 100° C. heat block for 10 min. 25 μL lysate was loaded on to SDS-PAGE gel (NuPAGE™ Novex™ 4-12% Bis-Tris Midi Protein Gels, cat. no. WG1402BOX, ThermoFisher) for western blotting analysis. Antibodies used for immunoblot analysis include FAK and Phospho-FAK(Y397) (cat. no. 3285 and 8556; Cell Signaling Technology, Beverly, MA). p-FAK(Y397) (clone 141-9) (cat. no. 44-625G, rabbit anti-FAKY397 ThermoFisher). Membranes were detected using infrared fluorescence dye (IRDye® 800CW Donkey anti-Rabbit IgG (H+L), cat. no. P/N 925-32213; IRDye® 680RD Donkey anti-Mouse IgG (H+L), cat. no. P/N 925-68072 and scanned on a LiCor Odyssey scanner (LiCor Biosciences, Lincoln, NB).

Example 9. Inhibitory Activity Against ERK in Cells

Cell-Based ERK1/2 (T202/Y204) Phosphorylation Assay

EOL-1 cells were cultured in RPMI-1640 medium with 10% fetal bovine serum (FBS) and 1% penicillin/streptomycin (Gibco BRL). Before the assay, EOL-1 cells were counted and seeded at 1×10⁶ cells/well in a 6-well plate, cultured overnight in RPMI-1640 medium with 10% FBS. The cells were treated with certain compounds of Compounds 1-24 at 0~3 μM for 3 hr. or 15 hr. at 37° C., then the cells were harvested, followed by 5 min. spin at 2000 rpm. After aspirating the supernatant, the cells were washed with cold PBS, span again, then 100 μL of RIPA lysis buffer (50 mM Tris-HCl, 1 mM EDTA, 1% NP-40, 0.5% sodium deoxycholate, and 0.1% SDS, pH 7.4, 150 mM NaCl, 1 mM $Na_3VO_4$) was added to the cell pellet to lyse the cells on ice for 30 min. After spin at 12,000 rpm for 5 min., 90 μL of the cell lysate was transferred to a fresh tube.

For an enzyme-linked immunosorbent assay (ELISA) assay, 10 μL of the lysate was used for p-ERK1/2 (T202/Y204) elisa assay. ELISA was done using the ERK 1/2 (pT202/Y204+Total) ELISA Kit (Abcam, ab176660) according to the manufacturer's instructions. Specifically, add 50 μL of all samples or standards to appropriate wells. Add 50 μL of the Antibody Cocktail to each well. Seal the plate and incubate for 1 hr. at r.t. on a plate shaker set to 400 rpm. Wash each well with 3×350 μL 1× Wash Buffer PT. Wash by aspirating or decanting from wells then dispensing 350 μL 1× Wash Buffer PT into each well. Complete removal of liquid at each step is essential for good performance. After the last wash invert the plate and blot it against clean with paper towels to remove excess liquid. Add 100 μL of TMB Substrate to each well and incubate for 15 min. in the dark on a plate shaker set to 400 rpm. Add 100 μL of Stop Solution to each well. Shake plate on a plate shaker for 1 min. to mix. Record the OD at 450 nm. This is an endpoint reading.

$EC_{50}$, the concentration at which 50% inhibition occurs, was evaluated based on the phospho-ERK1/2 (T202/Y204) signal or phospho-ERK1/2 (T202/Y204)/total-ERK signal ratio difference between the cells in a well treated with the test compound and not-treated which was regarded as 100%. The calculation of $EC_{50}$ and the result analysis were carried out using Microsoft Excel, and the results are shown in Table 10, wherein A means that $EC_{50}$<100 nM, C means that $EC_{50}$ is 1,000-3,000 nM.

TABLE 10

Inhibitory Activity against p-ERK in Cells

| Compound No. | $EC_{50}$ (nM) |
|---|---|
| 11 | A |
| 12 | C |

As shown in Table 10, many compounds showed inhibitory activity against ERK phosphorylation at T202/Y204 in EOL-1 cancer cells.

Example 10. Cancer Cell Growth Inhibition

In order to test certain compounds of Compounds 1 to 24 for cancer cell growth inhibition, a leukemia cancer cell line EOL-1, and triple negative breast cancer cell line MDA-MB-231 was used.

EOL-1 and MDA-MB-231 cells were cultured in a RPMI-1640 cell culture medium supplemented with 10% fetal bovine serum (FBS) and 1% penicillin/streptomycin (Gibco BRL).

The cancer cell lines stored in a liquid nitrogen tank were each quickly thawed at 37° C. water bath, and centrifuged to remove the DMSO in the freezing medium. The resulting cell pellet was mixed with a culture medium, incubated in a culture flask at 37° C. under 5% $CO_2$ for 2 to 3 days. The EOL-1 cells were sub-cultured by 1:5~10 dilution in fresh culture medium. For MD-MB-231 cells, the culture medium was removed and the remaining cells were washed with PBS (Phosphate Buffered Saline) and trypsinized by trypsin-EDTA. The detached cells were sub-cultured by 1:5~10 dilution in fresh culture medium.

For the cell growth inhibition assay, the cells were seeded in 96-well cell culture plates at $5 \times 10^4$ cells/well for EOL-1 and $5 \times 10^3$ cells/well for MDA-MB-231 cells in 50 μL and incubated at 37° C. under 5% $CO_2$ for 3 to 6 hr. before the compounds were added.

Certain compounds of Compounds 1-24 were dissolved in dimethylsulfoxide (DMSO) to a concentration of 10 mM. The DMSO solution containing test compound was diluted with a culture medium to a final concentration of 600 μM, and then diluted 100 times to 6 μM as top dose followed by 1:3 serial dilutions, and then add 50 μL diluted compounds to the 50 μL cells, with a final top dose at 3 μM and the plate was incubated at 37° C. under 5% $CO_2$ for 72 hr. The cell viability was determined by Cell Meter™ Fluorimetric Cell Cytotoxicity Assay Kit (AAT Bioquest) according to the manufacturer's instructions. Briefly, thaw and warm up the Assay Solution (Component A) to 37° C., and mix it thoroughly. Add 20 μL/well (96-well plate) of Assay Solution (Component A). Mix the reagents by shaking the plate gently for 30 seconds. Incubate the cells in a 37° C., 5% CO2 incubator for 1-24 hr., protected from light. Monitor the fluorescence intensity (bottom read) at Ex/Em=540/590 nm. Alternatively, read the O.D. at 570 nm (the reference wavelength should be 600 nm) to determine the cell viability in each well.

$IC_{50}$, the concentration at which 50% inhibition occurs, was evaluated based on the difference between the final density of the test cells and the initial density of the cells incubated in a well not-treated with the test compound which was regarded as 100%. The calculation of $GI_{50}$ and the result analysis were carried out using Microsoft Excel, and the results are shown in Table 11.

TABLE 11

$IC_{50}$ of Exemplary Compounds

| Compound No. | EOL1 $IC_{50}$ (μM) | MDA-MB-231 $IC_{50}$ (μM) |
|---|---|---|
| 1 | >3 | >3 |
| 2 | 2 | >3 |
| 3 | >3 | >3 |
| 5 | 1.9 | 3 |
| 7 | 2.5 | >3 |
| 11 | 0.025 | 0.3 |
| 12 | 2.4 | >3 |
| 16 | 2 | 3 |
| 18 | 0.75 | 1.5 |
| 19 | 0.35 | 2.5 |
| 20 | 2.25 | >3 |
| 22 | 1.2 | >3 |

As shown in Table 11, many compounds showed anticancer activity by inhibiting the growth of EOL-1 and MDA-MB-231 cells.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:
1. A method for treating or reducing a disease or disorder, comprising administering to a subject in need thereof a pharmaceutical composition comprising a compound having the structural formula of (VIII):

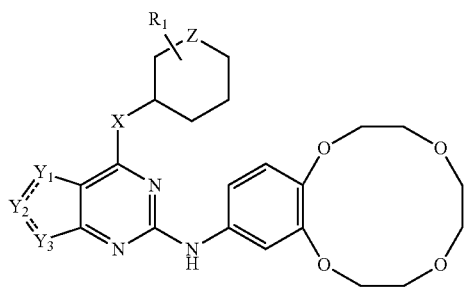

(VIII)

wherein,
X is NH;
Z is CH or N;
Y$_1$ is selected from CH, CH$_2$, N or NH;
Y$_2$ is selected from CH, CH$_2$, N or NH;
Y$_3$ is selected from CH, CH$_2$, N or NH;
the bond between Y$_1$ and Y$_2$ may be a double or single bond; the bond between Y$_2$ and Y$_3$ may be double or single bond; provided that
at least one Y$_1$, Y$_2$ and Y$_3$ is CH or CH$_2$; and
at least one of the bond between Y$_1$ and Y$_2$ and the bond between Y$_2$ and Y$_3$ is a single bond;
R$_1$ is selected from halogen, C$_1$-C$_6$ alkyl, C$_1$-C$_6$ alkoxy, CN, OH, amino, carboxylic amide, sulfonamide and R$_{1x}$, wherein R$_{1x}$ is selected from:

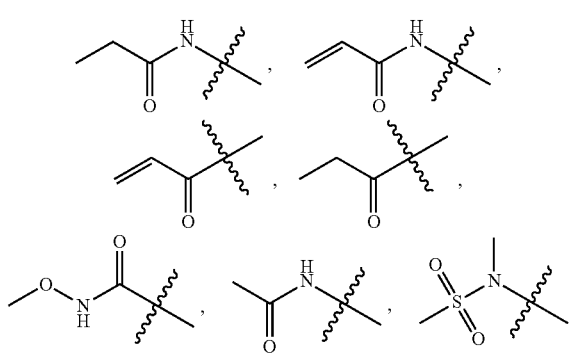

or a pharmaceutically acceptable form thereof, wherein the disease or disorder is cancer, inflammatory disease, fibrosis, autoimmune disease, or immunologically mediated disease.

2. The method of claim 1, effective to treat or reduce cancer.

3. The method of claim 1, effective to treat or reduce an inflammatory disease.

4. The method of claim 1, effective to treat or reduce fibrosis.

5. The method of claim 1, effective to treat or reduce an autoimmune disease.

6. The method of claim 1, effective to treat or reduce an immunologically mediated disease.

7. The method of claim 1, wherein the compound has inhibitory activity to Bruton's tyrosine kinase (BTK) and/or focal adhesion kinase (FAK).

8. The method of claim 7, wherein the compound is an inhibitor of BTK.

9. The method of claim 7, wherein the compound is an inhibitor of bone marrow tyrosine kinase (BMX).

10. The method of claim 7, wherein the compound is an inhibitor of both BTK and BMX.

11. The method of claim 10, wherein the compound is an inhibitor of interleukin-2 inducing T-cell kinase (ITK).

12. The method of claim 7, wherein the compound is an inhibitor of FAK.

13. The method of claim 12, wherein the compound is an inhibitor of BTK and of FAK.

14. The method of claim 7, wherein the compound is an inhibitor of BTK (C481S) mutant.

15. The method of claim 7, wherein the compound is an inhibitor of extracellular signal-regulated kinase (ERK).

16. A method for treating or reducing a disease or disorder, comprising administering to a subject in need thereof a pharmaceutical composition comprising a compound selected from:

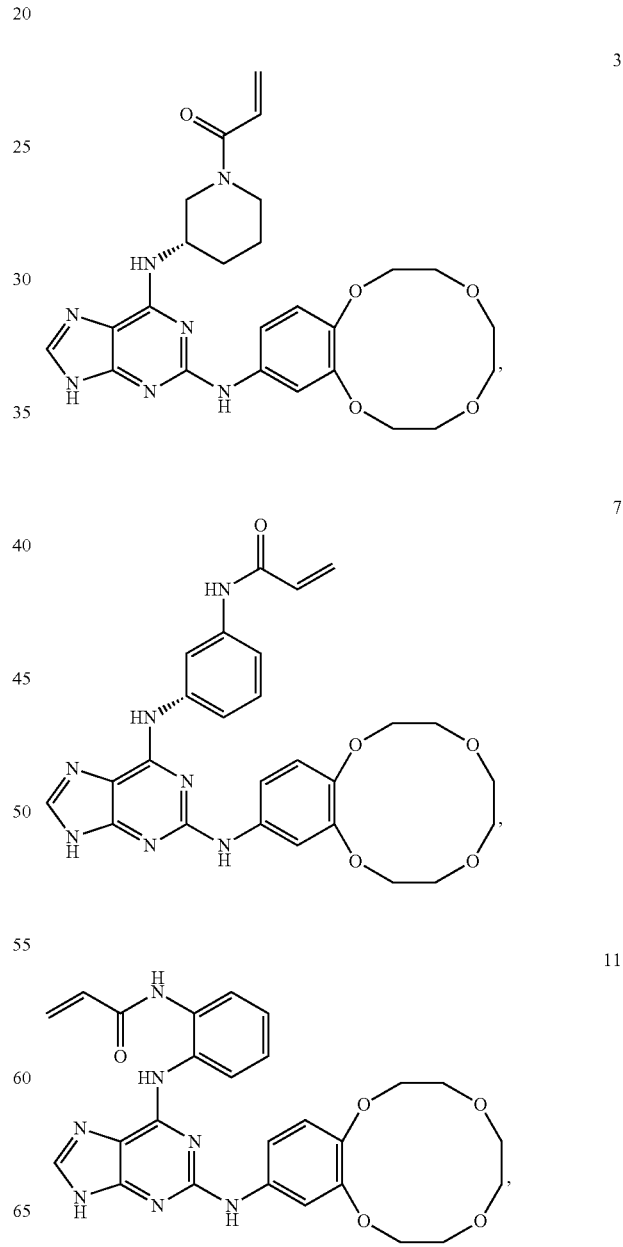

-continued
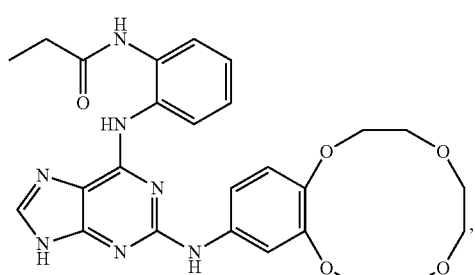
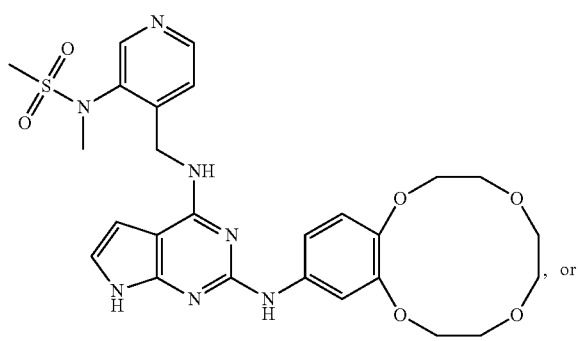
-continued
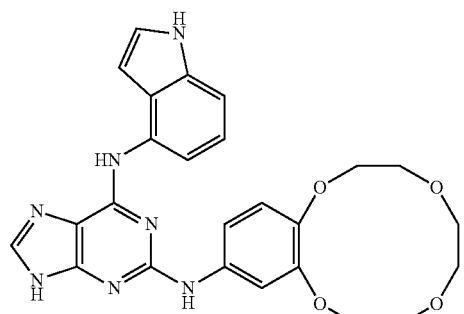
or a pharmaceutically acceptable form thereof, wherein the disease or disorder is cancer, inflammatory disease, fibrosis, autoimmune disease, or immunologically mediated disease.
* * * * *